United States Patent
Zhu et al.

(10) Patent No.: US 10,561,657 B2
(45) Date of Patent: Feb. 18, 2020

(54) PYRROLOPYRIMIDINE COMPOUND

(71) Applicants: CENTAURUS BIOPHARMA CO., LTD., Beijing (CN); CHIA TAI TIANQING PHARMACEUTICAL GROUP CO., LTD., Lianyungang (CN); LIANYUNGANG RUNZHONG PHARMACEUTICAL CO., LTD., Lianyungang (CN)

(72) Inventors: Li Zhu, Beijing (CN); Dengming Xiao, Beijing (CN); Yuandong Hu, Beijing (CN); Liguang Dai, Beijing (CN); Xiaowei Duan, Beijing (CN); Yinghui Sun, Beijing (CN); Yong Peng, Beijing (CN); Fansheng Kong, Beijing (CN); Hong Luo, Beijing (CN); Yongxin Han, Beijing (CN); Ling Yang, Lianyungang (CN); Shanchun Wang, Lianyungang (CN)

(73) Assignees: Centaurus Biophrama Co., Ltd., Beijing (CN); Chia Tai Tianqing Pharmaceutical Group Co., Ltd., Lianyungang (CN); Lianyungang Runzhong Pharmaceutical Co., Ltd., Lianyungang (CN)

( * ) Notice: Subject to any disclaimer, the term of this patent is extended or adjusted under 35 U.S.C. 154(b) by 205 days.

(21) Appl. No.: 15/536,648

(22) PCT Filed: Dec. 15, 2015

(86) PCT No.: PCT/CN2015/097411
§ 371 (c)(1),
(2) Date: Jun. 16, 2017

(87) PCT Pub. No.: WO2016/095805
PCT Pub. Date: Jun. 23, 2016

(65) Prior Publication Data
US 2019/0201403 A1 Jul. 4, 2019

(30) Foreign Application Priority Data
Dec. 16, 2014 (CN) .......................... 2014 1 0784461

(51) Int. Cl.
A61K 31/519 (2006.01)
A61K 31/5377 (2006.01)
C07D 487/04 (2006.01)
A61P 35/00 (2006.01)

(52) U.S. Cl.
CPC ............ A61K 31/519 (2013.01); A61P 35/00 (2018.01)

(58) Field of Classification Search
CPC .............. A61K 31/519; A61K 31/5377; C07D 487/04; A61P 35/00
See application file for complete search history.

(56) References Cited

U.S. PATENT DOCUMENTS

| 2009/0181959 A1 | 7/2009 | Rodgers et al. |
| 2011/0086810 A1 | 4/2011 | Rodgers et al. |
| 2012/0316186 A1 | 12/2012 | Ledeboar et al. |
| 2014/0343034 A1 | 11/2014 | Tanimoto et al. |

FOREIGN PATENT DOCUMENTS

| CN | 101448826 A | 6/2009 |
| CN | 102026999 A | 4/2011 |
| CN | 102596960 A | 7/2012 |
| JP | 2009519340 A | 5/2009 |
| JP | 2012504639 A | 2/2012 |
| WO | 2007070514 A1 | 6/2007 |
| WO | 2009114512 A2 | 9/2009 |
| WO | 2010039939 A1 | 4/2010 |
| WO | 20130173506 A2 | 11/2013 |
| WO | 2015188681 A1 | 12/2015 |

OTHER PUBLICATIONS

International Search Report issued in the prior PCT application PCT /CN2015/097411.
European search report dated Apr. 4, 2017 in the corresponding Europe application (application No. 15869312.7).
Examination Report in IN201717021226 dated Nov. 18, 2019.

Primary Examiner — Brenda L Coleman
(74) Attorney, Agent, or Firm — Kilpatrick Townsend & Stockton LLP

(57) ABSTRACT

The present application relates to the field of pharmaceutical chemistry, and in particular, to a pyrrolopyrimidine compound represented by general formula (I), a stereoisomer thereof, or a pharmaceutically acceptable salt thereof. The present invention further relates to a method for preparing the pyrrolopyrimidine compound represented by general formula (I), pharmaceutical compositions and an application of the pyrrolopyrimidine compound in treating diseases mediated by Janus Kinase.

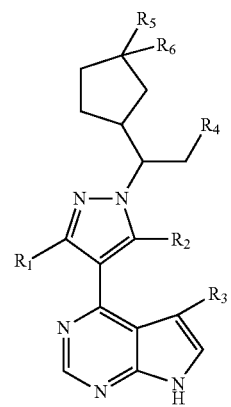

19 Claims, No Drawings

PYRROLOPYRIMIDINE COMPOUND

CROSS REFERENCE TO RELATED APPLICATION

The present application is a National Stage of International Application No. PCT/CN2015/097411, filed Dec. 15, 2015, which claims the priority and benefit of Chinese Patent Application No. 201410784461.2 filed on Dec. 16, 2014 5, the contents of which are incorporated herein by reference in their entirety.

TECHNICAL FIELD

The present application relates to the field of medicine. In particular, the present application relates to a pyrrolopyrimidine compound represented by Formula (I), a stereoisomer thereof, or a pharmaceutically acceptable salt thereof. The present application also relates to a method for preparing a pyrrolopyrimidine compound represented by Formula (I), a pharmaceutical composition comprising the compound, and a use of the compound in the treatment of a disease mediated by Janus kinase.

BACKGROUND ART

Protein kinases (PKs), also called protein phosphakinases, are a sort of enzymes that catalyze the protein phosphorylation reaction. The protein kinases exert their physiological functions, including cell growth, survival and differentiation, organ formation and morphological change, neovascularization, tissue repair and regeneration, by catalyzing the phosphorylation of a protein. In addition to normal physiological functions, many protein kinases play an important role in human diseases (such as cancer). Cancerogenic protein kinases, i.e., a subgroup of protein kinases, when dysregulated, may cause tumor formation and growth, and further cause tumor metastasis and progression. To date, the cancerogenic protein kinases are one of the most important targets for treating cancers.

The protein kinases can be classified into receptor type and non-receptor type. A subfamily of the non-receptor type of tyrosine kinases (PTKs) comprises Janus kinase (JAK). As for the non-receptor type of tyrosine kinases, reference can be made in detail to, e.g., Bolen J B., Nonreceptor tyrosine protein kinases, Oncogene, 1993, 8(8): 2025-31.

Janus kinase (JAK) is a non-receptor type of tyrosine kinases (PTKs), which resides in cells and transduces cytokine stimulation signal via JAK-STAT pathway. By JAK-STAT pathway, a chemical signal outside the cell is transduced into a gene promoter on endonuclear DNA through cell membrane, and finally affects the DNA in cell to change its transcription and activity level. JAK-STAT pathway mainly consists of three components: (1) a receptor; (2) Janus kinase (JAK) and (3) a signal transducer and activator of transcription (STAT) protein. The receptor can be activated by interferon, interleukin, growth factor or other chemical messenger, and such activation leads to the phosphorylation of JAK itself. Then, the STAT protein bonds to the phosphorylated receptor, so that STAT is phosphorylated by JAK. After that, the phosphorylated STAT protein is isolated from the receptor, then dimerized and translocated into cell nucleus, thereby bonding to specific DNA site and changing transcription (Scott, M. J., C. J. Godshall et al. (2002). "Jaks, STATs, Cytokines, and Sepsis" Clin Diagn Lab Immunol 9(6): 1153-9).

JAK family plays a role in the cytokine-dependent regulation of proliferation and function of cells involved in immune response. At present, there are four known mammalian JAK family members: JAK1, JAK2, JAK3 and TYK2 (Tyrosine kinase 2). The JAK proteins have a size ranging from 120 kDa to 140 kDa, and comprise 7 conserved JAK homology (JH) domains. One of them is a functional catalytic kinase domain, and another is a pseudokinase domain which effectively exerts a regulatory function and/or acts as a docking site for STATs (Scott, Godshall et al. 2002, supra).

At present, the inhibitors for Janus kinase or relevant kinases have been reported, for example, in WO9965909, US20040198737, WO2004099204, WO2004099205, WO200142246, WO200472063, WO9962908, WO2007070514, etc.

SUMMARY

In one aspect, the present application provides a compound represented by Formula (I), a stereoisomer thereof, or a pharmaceutically acceptable salt thereof:

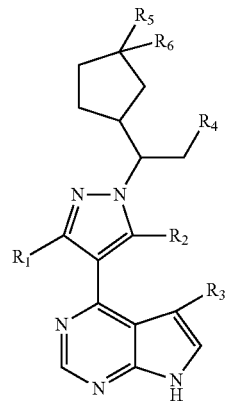

wherein, $R_1$ and $R_2$ are each independently selected from the group consisting of H, halo, cyano, $C_{1\sim8}$alkyl, —$NR_7R_8$, —NH—$C_{1\sim6}$alkylene-$NR_9R_{10}$, —NHCO—$C_{1\sim6}$alkylene-$NR_9R_{10}$, —NH—$C_{1\sim6}$alkylene-CO—$NR_9R_{10}$, —NHCO—$C_{1\sim6}$alkylene-COO—$C_{1\sim6}$alkyl, —NH—$C_{3\sim6}$cycloalkylene—CO—$NR_9R_{10}$, —NH—$C_{2\sim6}$alkenylene-CONR$_9$R$_{10}$, —NH—$C_{1\sim6}$alkylene-cyano, —NHCO—NH—$R_{11}$, —CONR$_{12}$R$_{13}$, and —CONH—$C_{1\sim6}$alkylene-NR$_{12}$R$_{13}$, wherein the $C_{1\sim8}$alkyl is optionally substituted with hydroxyl, halo, or amino, provided that $R_1$ and $R_2$ are not both H;

$R_7$ and $R_8$ are each independently selected from the group consisting of H, $C_{1\sim6}$alkyl, $C_{1\sim6}$alkylacyl, and $C_{1\sim6}$alkylsulfonyl; or $R_7$ and $R_8$ together with N atom to which they attach form a 5- or 6-membered heterocyclyl, and the 5- or 6-membered heterocyclyl is optionally substituted with oxo;

$R_9$ and $R_{10}$ are each independently selected from the group consisting of H, hydroxyl, and $C_{1\sim6}$alkyl; or $R_9$ and $R_{10}$ together with N atom to which they attach form a 5- or 6-membered heterocyclyl;

$R_{11}$ is selected from the group consisting of a 5- or 6-membered heteroaryl optionally substituted with $C_{1\sim4}$alkyl;

$R_{12}$ and $R_{13}$ are each independently selected from the group consisting of H, $C_{1\sim6}$alkyl, $C_{1\sim6}$alkylacyl, and $C_{1\sim6}$alkylsulfonyl; or $R_{12}$ and $R_{13}$ together with N atom to which they attach form a 5- or 6-membered heterocyclyl, and the 5- or 6-membered heterocyclyl is optionally substituted with oxo;

$R_3$ is selected from the group consisting of H and halo;

$R_4$ is selected from the group consisting of cyano and —$CONH_2$;

$R_5$ and $R_6$ are each independently selected from the group consisting of H, hydroxyl, and halo.

In another aspect, the present application provides a compound represented by Formula (I), a stereoisomer thereof, or a pharmaceutically acceptable salt thereof, for use in the treatment of a disease mediated by Janus kinase.

In another aspect, the present application provides a pharmaceutical composition comprising a therapeutically effective amount of a compound represented by Formula (I), a stereoisomer thereof, or a pharmaceutically acceptable salt thereof, and one or more pharmaceutically acceptable carriers or excipients.

In still another aspect, the present application provides the use of a compound represented by Formula (I), a stereoisomer thereof, or a pharmaceutically acceptable salt thereof, or a pharmaceutical composition described above, in the preparation of a medicament for treating a disease mediated by Janus kinase.

In yet another aspect, the present application provides a method for treating a disease mediated by Janus kinase, comprising administering to a patient a therapeutically effective amount of a compound represented by Formula (I), a stereoisomer thereof, or a pharmaceutically acceptable salt thereof, or a pharmaceutical composition described above.

DETAILED DESCRIPTION

In one aspect, the present application provides a compound represented by Formula (I), a stereoisomer thereof, or a pharmaceutically acceptable salt thereof:

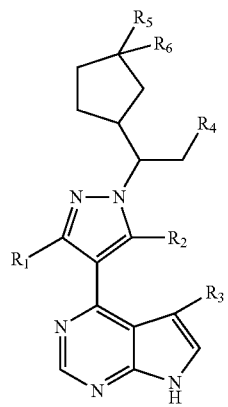

I wherein, $R_1$ and $R_2$ are each independently selected from the group consisting of H, halo, cyano, $C_{1\sim8}$alkyl, —$NR_7R_8$, —NH—$C_{1\sim6}$alkylene-$NR_9R_{10}$, —NHCO—$C_{1\sim6}$alkylene-$NR_9R_{10}$, —NH—$C_{1\sim6}$alkylene-CO—$NR_9R_{10}$, —NHCO—$C_{1\sim6}$alkylene-COO—$C_{1\sim6}$alkyl, —NH—$C_{3\sim6}$cycloalkylene—CO—$NR_9R_{10}$, —NH—$C_{2\sim6}$alkenylene-$CONR_9R_{10}$, —NH—$C_{1\sim6}$alkylene-cyano, —NHCO—NH—$R_{11}$, —$CONR_{12}R_{13}$, and —CONH—$C_{1\sim6}$alkylene-$NR_{12}R_{13}$, wherein the $C_{1\sim8}$alkyl is optionally substituted with hydroxyl, halo, or amino, provided that $R_1$ and $R_2$ are not both H;

$R_7$ and $R_8$ are each independently selected from the group consisting of H, $C_{1\sim6}$alkyl, $C_{1\sim6}$alkylacyl, and $C_{1\sim6}$alkylsulfonyl; or $R_7$ and $R_8$ together with N atom to which they attach form a 5- or 6-membered heterocyclyl, and the 5- or 6-membered heterocyclyl is optionally substituted with oxo;

$R_9$ and $R_{10}$ are each independently selected from the group consisting of H, hydroxyl, and $C_{1\sim6}$alkyl; or $R_9$ and $R_{10}$ together with N atom to which they attach form a 5- or 6-membered heterocyclyl;

$R_{11}$ is selected from the group consisting of a 5- or 6-membered heteroaryl optionally substituted with $C_{1\sim4}$alkyl;

$R_{12}$ and $R_{13}$ are each independently selected from the group consisting of H, $C_{1\sim6}$alkyl, $C_{1\sim6}$alkylacyl, and $C_{1\sim6}$alkylsulfonyl; or $R_{12}$ and $R_{13}$ together with N atom to which they attach form a 5- or 6-membered heterocyclyl, and the 5- or 6-membered heterocyclyl is optionally substituted with oxo;

$R_3$ is selected from the group consisting of H and halo;

$R_4$ is selected from the group consisting of cyano and —$CONH_2$;

$R_5$ and $R_6$ are each independently selected from the group consisting of H, hydroxyl, and halo.

In some preferable embodiments, $R_1$ and $R_2$ are each independently selected from the group consisting of H, halo, cyano, $C_{1\sim6}$alkyl, —$NR_7R_8$, —NH—$C_{1\sim4}$alkylene-$NR_9R_{10}$, —NHCO—$C_{1\sim4}$alkylene-$NR_9R_{10}$, —NH—$C_{1\sim4}$alkylene-CO—$NR_9R_{10}$, —NHCO—$C_{1\sim4}$alkylene-COO—$C_{1\sim4}$alkyl, —NH—$C_{3\sim5}$cycloalkylene-CO—$NR_9R_{10}$, —NH—$C_{2\sim4}$alkenylene-$CONR_9R_{10}$, —NH—$C_{1\sim4}$alkylene-cyano, —NHCO—NH—$R_{11}$, —$CONR_{12}R_{13}$, and —CONH—$C_{1\sim4}$alkylene-$NR_{12}R_{13}$, wherein the $C_{1\sim6}$alkyl is optionally substituted with hydroxyl, halo, or amino, provided that $R_1$ and $R_2$ are not both H.

In some preferable embodiments, $R_1$ is selected from the group consisting of H, halo, cyano, $C_{1\sim8}$alkyl, —$NR_7R_8$, —NH—$C_{1\sim6}$alkylene-$NR_9R_{10}$, —NHCO—$C_{1\sim6}$alkylene-$NR_9R_{10}$, —NH—$C_{1\sim6}$alkylene-CO—$NR_9R_{10}$, —NHCO—$C_{1\sim6}$alkylene-COO—$C_{1\sim6}$alkyl, —NH—$C_{3\sim6}$cycloalkylene—CO—$NR_9R_{10}$, —NH—$C_{2\sim6}$alkenylene-$CONR_9R_{10}$, —NH—$C_{1\sim6}$alkylene-cyano, —NHCO—NH—$R_{11}$, —$CONR_{12}R_{13}$, and —CONH—$C_{1\sim6}$alkylene-$NR_{12}R_{13}$, wherein the $C_{1\sim8}$alkyl is optionally substituted with hydroxyl, halo, or amino; and $R_2$ is selected from the group consisting of H and —$NH_2$, provided that $R_1$ and $R_2$ are not both H.

In some preferable embodiments, $R_1$ is selected from the group consisting of H, halo, cyano, $C_{1\sim6}$alkyl, —$NR_7R_8$, —NH—$C_{1\sim4}$alkylene-$NR_9R_{10}$, —NHCO—$C_{1\sim4}$alkylene-$NR_9R_{10}$, —NH—$C_{1\sim4}$alkylene-CO—$NR_9R_{10}$, —NHCO—$C_{1\sim4}$alkylene-COO—$C_{1\sim4}$alkyl, —NH—$C_{3\sim5}$cycloalkylene—CO—$NR_9R_{10}$, —NH—$C_{2\sim4}$alkenylene-$CONR_9R_{10}$, —NH—$C_{1\sim4}$alkylene-cyano, —NHCO—NH—$R_{11}$, —$CONR_{12}R_{13}$, and —CONH—$C_{1\sim4}$alkylene-$NR_{12}R_{13}$, wherein the $C_{1\sim6}$alkyl is optionally substituted with hydroxyl, halo, or amino; and $R_2$ is selected from the group consisting of H and —$NH_2$, provided that $R_1$ and $R_2$ are not both H.

In some preferable embodiments, $R_7$ and $R_8$ are each independently selected from the group consisting of H, $C_{1\sim4}$alkyl, $C_{1\sim4}$alkylacyl, and $C_{1\sim4}$alkylsulfonyl; or $R_7$ and $R_8$ together with N atom to which they attach form a heterocyclyl selected from the group consisting of:

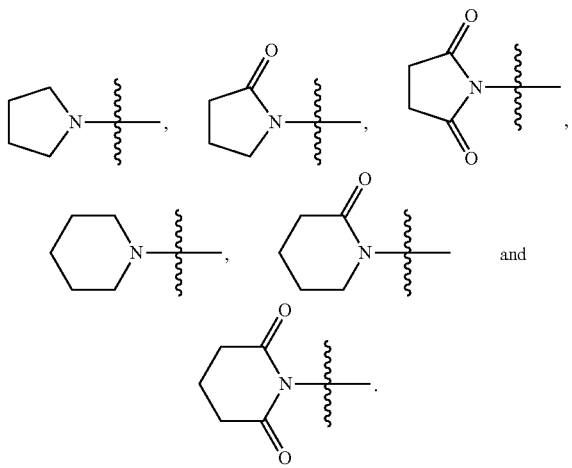

In some preferable embodiments, $R_7$ is selected from the group consisting of H, $C_{1\sim 6}$alkyl, $C_{1\sim 6}$alkylacyl, and $C_{1\sim 6}$alkylsulfonyl; $R_8$ is selected from the group consisting of H and $C_{1\sim 6}$alkyl; or $R_7$ and $R_8$ together with N atom to which they attach form a 5- or 6-membered heterocyclyl, and the 5- or 6-membered heterocyclyl is optionally substituted with oxo.

In some preferable embodiments, $R_7$ is selected from the group consisting of H, $C_{1\sim 4}$alkyl, $C_{1\sim 4}$alkylacyl, and $C_{1\sim 4}$alkylsulfonyl; $R_8$ is selected from the group consisting of H and $C_{1\sim 4}$alkyl; or $R_7$ and $R_8$ together with N atom to which they attach form a heterocyclyl selected from the group consisting of:

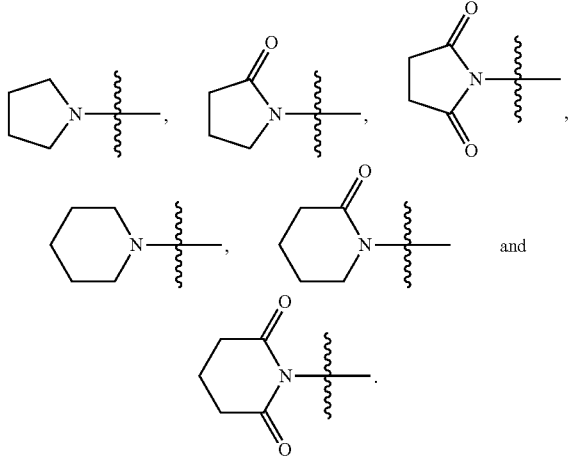

In some preferable embodiments, $R_9$ and $R_{10}$ are each independently selected from the group consisting of H, hydroxyl, and $C_{1\sim 4}$alkyl; or $R_9$ and $R_{10}$ together with N atom to which they attach form pyrrolidinyl, piperidinyl, morpholinyl, piperazinyl or oxazolidinyl.

In some preferable embodiments, $R_9$ is selected from the group consisting of H, hydroxyl, and $C_{1\sim 4}$alkyl; $R_{10}$ is selected from the group consisting of H and $C_{1\sim 4}$alkyl; or $R_9$ and $R_{10}$ together with N atom to which they attach form a 5- or 6-membered heterocyclyl.

In some preferable embodiments, $R_9$ is selected from the group consisting of H, hydroxyl, and $C_{1\sim 4}$alkyl; $R_{10}$ is selected from the group consisting of H and $C_{1\sim 4}$alkyl; or $R_9$ and $R_{10}$ together with N atom to which they attach form pyrrolidinyl, piperidinyl, morpholinyl, piperazinyl or oxazolidinyl.

In some preferable embodiments, $R_{11}$ is a heteroaryl selected from the group consisting of:

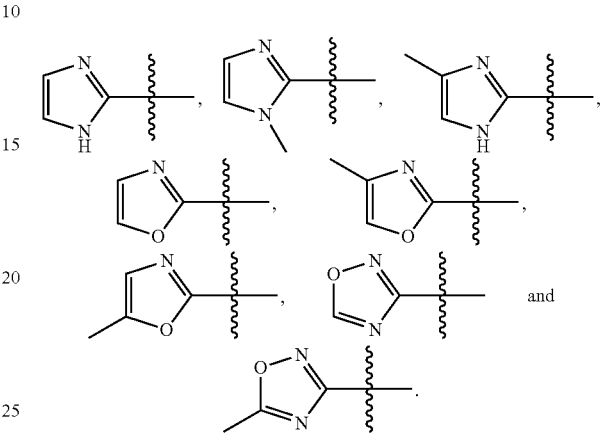

In some preferable embodiments, $R_{12}$ and $R_{13}$ are each independently selected from the group consisting of H, $C_{1\sim 4}$alkyl, $C_{1\sim 4}$alkylacyl, and $C_{1\sim 4}$alkylsulfonyl; or $R_{12}$ and $R_{13}$ together with N atom to which they attach form a heterocyclyl selected from the group consisting of:

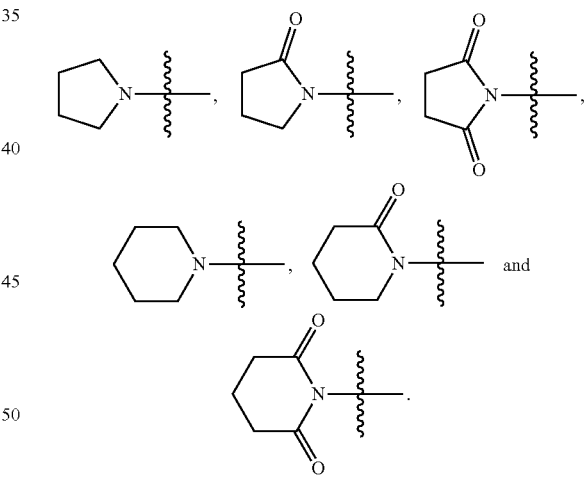

In some preferable embodiments, $R_{12}$ is selected from the group consisting of H, $C_{1\sim 6}$alkyl, $C_{1\sim 6}$alkylacyl, and $C_{1\sim 6}$alkylsulfonyl; $R_{13}$ is selected from the group consisting of H and $C_{1\sim 6}$alkyl; or $R_{12}$ and $R_{13}$ together with N atom to which they attach form a 5- or 6-membered heterocyclyl, and the 5- or 6-membered heterocyclyl is optionally substituted with oxo.

In some preferable embodiments, $R_{12}$ is selected from the group consisting of H, $C_{1\sim 4}$alkyl, $C_{1\sim 4}$alkylacyl, and $C_{1\sim 4}$alkylsulfonyl; $R_{13}$ is selected from the group consisting of H and $C_{1\sim 4}$alkyl; or $R_{12}$ and $R_{13}$ together with N atom to which they attach form a heterocyclyl selected from the group consisting of:

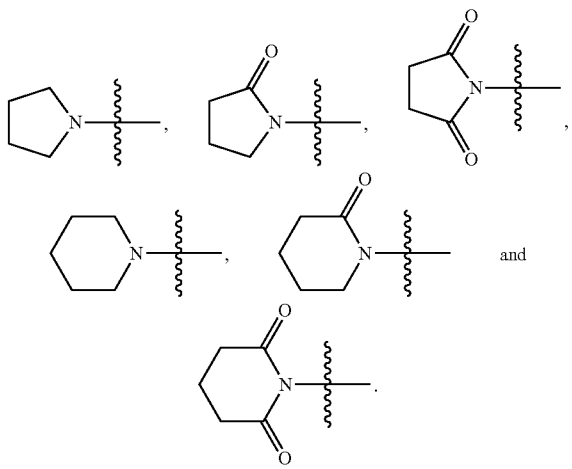

In some more preferable embodiments, $R_1$ and $R_2$ are each independently selected from the group consisting of H, F, Cl, Br, I, cyano, methyl, ethyl, propyl, butyl, —$NR_7R_8$, —NH-methylene-$NR_9R_{10}$, —NH-ethylene-$NR_9R_{10}$, —NH-propylene-$NR_9R_{10}$, —NHCO-methylene-$NR_9R_{10}$, —NHCO-ethylene-$NR_9R_{10}$, —NHCO-propylene-$NR_9R_{10}$, —NH-methylene-CO—$NR_9R_{10}$, —NH-ethylene-CO—$NR_9R_{10}$, —NH-propylene-CO—$NR_9R_{10}$, —NHCO-methylene-COO-methyl, —NHCO-methylene-COO-ethyl, —NHCO-methylene-COO-propyl, —NHCO-ethylene-COO-methyl, —NHCO-ethylene-COO-ethyl, —NHCO-ethylene-COO-propyl, —NHCO-propylene-COO-methyl, —NHCO-propylene-COO-ethyl, —NHCO-propylene-COO-propyl, —NH-cyclopropylene-CO—$NR_9R_{10}$, —NH-cyclobutylene-CO—$NR_9R_{10}$, —NH-cyclopentylene-CO—$NR_9R_{10}$, —NH-vinylene-$CONR_9R_{10}$, —NH-propenylene-$CONR_9R_{10}$, —NH-allylene-$CONR_9R_{10}$, —NH-methylene-cyano, —NH-ethylene-cyano, —NH-propylene-cyano, —NHCO—NH—$R_{11}$, —$CONR_{12}R_{13}$, —CONH-methylene-$NR_{12}R_{13}$, —CONH-ethylene-$NR_{12}R_{13}$, and —CONH-propylene-$NR_{12}R_{13}$, wherein the methyl, ethyl, propyl or butyl is optionally substituted with one or more groups selected from the group consisting of hydroxyl, F, Cl, Br, I, methylamino, ethylamino, propylamino, dimethylamino, diethylamino, dipropylamino and methylethylamino, provided that $R_1$ and $R_2$ are not both H.

In some more preferable embodiments, $R_1$ is selected from the group consisting of H, F, Cl, Br, I, cyano, methyl, ethyl, propyl, butyl, —$NR_7R_8$, —NH-methylene-$NR_9R_{10}$, —NH-ethylene-$NR_9R_{10}$, —NH-propylene-$NR_9R_{10}$, —NHCO-methylene-$NR_9R_{10}$, —NHCO-ethylene-$NR_9R_{10}$, —NHCO-propylene-$NR_9R_{10}$, —NH-methylene-CO—$NR_9R_{10}$, —NH-ethylene-CO—$NR_9R_{10}$, —NH-propylene-CO—$NR_9R_{10}$, —NHCO-methylene-COO-methyl, —NHCO-methylene-COO-ethyl, —NHCO-methylene-COO-propyl, —NHCO-ethylene-COO-methyl, —NHCO-ethylene-COO-ethyl, —NHCO-ethylene-COO-propyl, —NHCO-propylene—COO-methyl, —NHCO-propylene-COO-ethyl, —NHCO-propylene-COO-propyl, —NH-cyclopropylene-CO—$NR_9R_{10}$, —NH-cyclobutylene-CO—$NR_9R_{10}$, —NH-cyclopentylene —CO—$NR_9R_{10}$, —NH-vinylene-$CONR_9R_{10}$, —NH-propenylene-$CONR_9R_{10}$, —NH-allylene-$CONR_9R_{10}$, —NH-methylene-cyano, —NH-ethylene-cyano, —NH-propylene-cyano, —NHCO—NH—$R_{11}$, —$CONR_{12}R_{13}$, —CONH-methylene-$NR_{12}R_{13}$, —CONH-ethylene-$NR_{12}R_{13}$, and —CONH-propylene-$NR_{12}R_{13}$, wherein the methyl, ethyl, propyl or butyl is optionally substituted with one or more groups selected from the group consisting of hydroxyl, F, Cl, Br, I, methylamino, ethylamino, propylamino, dimethylamino, diethylamino, dipropylamino and methylethylamino; and $R_2$ is selected from the group consisting of H and —$NH_2$, provided that $R_1$ and $R_2$ are not both H.

In some more preferable embodiments, $R_7$ and $R_8$ are each independently selected from the group consisting of H, methyl, ethyl, propyl, formyl, acetyl, propionyl, methylsulfonyl, ethylsulfonyl, and propylsulfonyl; or $R_7$ and $R_8$ together with N atom to which they attach form a heterocyclyl selected from the group consisting of:

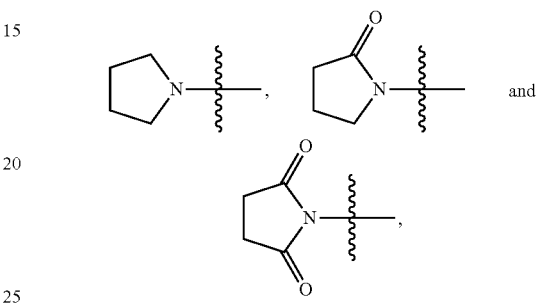

In some more preferable embodiments, $R_7$ is selected from the group consisting of H, methyl, ethyl, propyl, formyl, acetyl, propionyl, methylsulfonyl, ethylsulfonyl, and propylsulfonyl; $R_8$ is selected from the group consisting of H, methyl, ethyl, and propyl; or $R_7$ and $R_8$ together with N atom to which they attach form a heterocyclyl selected from the group consisting of:

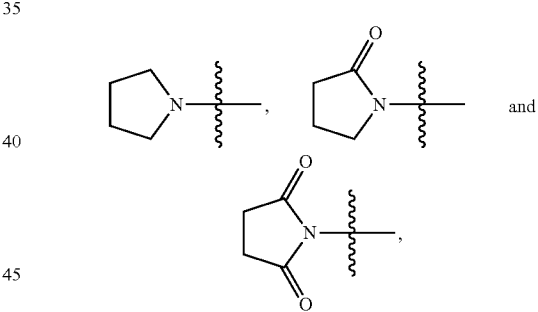

In some more preferable embodiments, $R_9$ and $R_{10}$ are each independently selected from the group consisting of H, hydroxyl, methyl, ethyl, and propyl; or $R_9$ and $R_{10}$ together with N atom to which they attach form piperidinyl, morpholinyl or piperazinyl.

In some more preferable embodiments, $R_9$ is selected from the group consisting of H, hydroxyl, methyl, ethyl, and propyl; $R_{10}$ is selected from the group consisting of H, methyl, ethyl, and propyl; or $R_9$ and $R_{10}$ together with N atom to which they attach form piperidinyl, morpholinyl or piperazinyl.

In some more preferable embodiments, $R_{11}$ is a heteroaryl selected from the group consisting of:

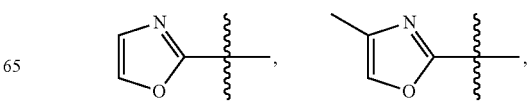

-continued

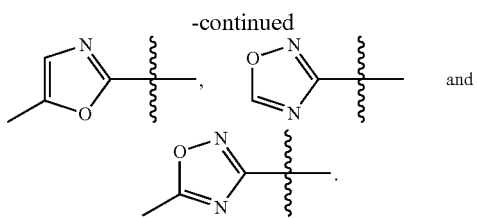

In some more preferable embodiments, $R_{12}$ and $R_{13}$ are each independently selected from the group consisting of H, methyl, ethyl, propyl, formyl, acetyl, propionyl, methylsulfonyl, ethylsulfonyl, and propylsulfonyl; or $R_{12}$ and $R_{13}$ together with N atom to which they attach form a heterocyclyl selected from the group consisting of:

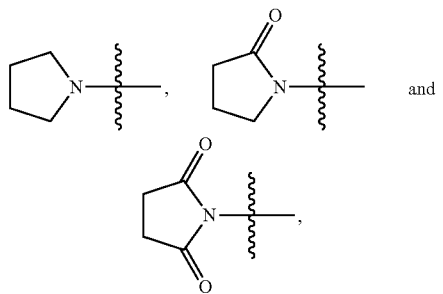

In some more preferable embodiments, $R_{12}$ is selected from the group consisting of H, methyl, ethyl, propyl, formyl, acetyl, propionyl, methylsulfonyl, ethylsulfonyl, and propylsulfonyl; $R_{13}$ is selected from the group consisting of H, methyl, ethyl, and propyl; or $R_{12}$ and $R_{13}$ together with N atom to which they attach form a heterocyclyl selected from the group consisting of:

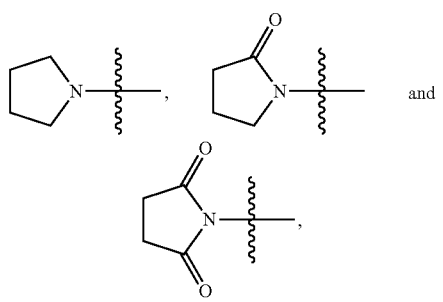

In some even more preferable embodiments, $R_1$ and $R_2$ are each independently selected from the group consisting of H, Br, cyano, methyl, —$NR_7R_8$, —NH-ethylene-$NR_9R_{10}$, —NHCO-methylene-$NR_9R_{10}$, —NH-methylene-CO—$NR_9R_{10}$, —NH-ethylene-CO—$NR_9R_{10}$, —NHCO-ethylene-COO-ethyl, —NH-cyclobutylene-CO—$NR_9R_{10}$, —NH-propenylene-$CONR_9R_{10}$, —NH-ethylene-cyano, —NHCO—NH—$R_{11}$, —$CONR_{12}R_{13}$, and —CONH-ethylene-$NR_{12}R_{13}$, wherein the methyl is optionally substituted with hydroxyl, F or methylamino, provided that $R_1$ and $R_2$ are not both H.

In some even more preferable embodiments, $R_1$ is selected from the group consisting of H, Br, cyano, methyl, —$NR_7R_8$, —NH-ethylene-$NR_9R_{10}$, —NHCO-methylene-$NR_9R_{10}$, —NH-methylene-CO—$NR_9R_{10}$, —NH-ethylene-CO—$NR_9R_{10}$, —NHCO-ethylene-COO-ethyl, —NH-cyclobutylene-CO—$NR_9R_{10}$, —NH-propenylene-$CONR_9R_{10}$, —NH-ethylene-cyano, —NHCO—NH—$R_{11}$, —$CONR_{12}R_{13}$, and —CONH-ethylene-$NR_{12}R_{13}$, wherein the methyl is optionally substituted with hydroxyl, F or methylamino; and $R_2$ is selected from the group consisting of H and —$NH_2$, provided that $R_1$ and $R_2$ are not both H.

In some even more preferable embodiments, $R_7$ and $R_8$ are each independently selected from the group consisting of H, ethyl, acetyl, and methylsulfonyl; or $R_7$ and $R_8$ together with N atom to which they attach form

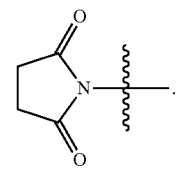 [SMILES: *N1C(=O)CCC1=O]

In some even more preferable embodiments, $R_7$ is selected from the group consisting of H, ethyl, acetyl, and methylsulfonyl; $R_8$ is selected from the group consisting of H and ethyl; or $R_7$ and $R_8$ together with N atom to which they attach form

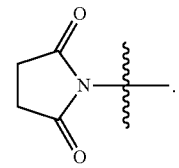 [SMILES: *N1C(=O)CCC1=O]

In some even more preferable embodiments, $R_9$ and $R_{10}$ are each independently selected from the group consisting of H and hydroxyl; or $R_9$ and $R_{10}$ together with N atom to which they attach form morpholinyl.

In some even more preferable embodiments, $R_9$ is selected from the group consisting of H and hydroxyl; $R_{10}$ is selected from H; or $R_9$ and $R_{10}$ together with N atom to which they attach form morpholinyl.

In some even more preferable embodiments, $R_{11}$ is

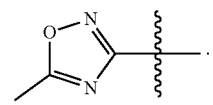 [SMILES: *c1noc(C)n1]

In some even more preferable embodiments, $R_{12}$ and $R_{13}$ are each independently selected from the group consisting of H and methyl.

In some even more preferable embodiments, $R_{12}$ is selected from the group consisting of H and methyl; and $R_{13}$ is selected from the group consisting of H and methyl.

In some particularly preferable embodiments, $R_1$ is selected from the group consisting of H, Br, cyano, methyl, —$NR_7R_8$, —NH-ethylene-$NR_9R_{10}$, —NHCO-methylene-$NR_9R_{10}$, —NH-methylene-CO—$NR_9R_{10}$, —NH-ethylene-CO—$NR_9R_{10}$, —NHCO-ethylene-COO-ethyl, —NH-cyclobutylene-CO—$NR_9R_{10}$, —NH-propenylene-$CONR_9R_{10}$, —NH-ethylene-cyano, —NHCO—NH—$R_{11}$, —$CONR_{12}R_{13}$, and —CONH-ethylene-$NR_{12}R_{13}$, wherein the methyl is optionally substituted with hydroxyl, F or methylamino; $R_7$ and $R_8$ are each independently selected from the group consisting of H, ethyl, acetyl, and methylsulfonyl; or $R_7$ and $R_8$ together with N atom to which they attach form

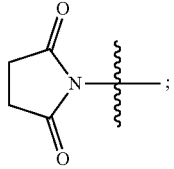 [SMILES: *N1C(=O)CCC1=O]

$R_9$ and $R_{10}$ are each independently selected from the group consisting of H and hydroxyl; or $R_9$ and $R_{10}$ together with N atom to which they attach form morpholinyl; $R_{11}$ is

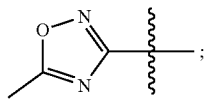

$R_{12}$ and $R_{13}$ are each independently selected from the group consisting of H and methyl; and $R_2$ is selected from the group consisting of H and —$NH_2$, provided that $R_1$ and $R_2$ are not both H.

In some particularly preferable embodiments, $R_1$ is selected from the group consisting of H, Br, —CN, —$NH_2$, —$NHC_2H_5$, —$N(C_2H_5)_2$, —NHC(=O)$CH_3$, —$NHSO_2CH_3$, —$NHCH_2CH_2$-morpholinyl, —NHC(=O)$CH_2$-morpholinyl, —$NHCH_2CH_2$C(=O)-morpholinyl, —$NHCH_2$C(=O)-morpholinyl, —NHC(=O)$CH_2CH_2$C(=O)$OC_2H_5$, succinimido, —NH-cyclobutylene-C(=O)-morpholinyl, —$NHCH_2$CH=CHC(=O)NHOH, —$NHCH_2CH_2$C(=O)NHOH, —$NHCH_2CH_2$CN, —NHC(=O)NH-(5-methyl-1,2,4-oxadiazol-3-yl), —C(=O)$NH_2$, —C(=O)$NHCH_3$, —C(=O)$NHCH_2CH_2NH_2$, —$CH_2OH$, —$CH_2F$, —$CHF_2$, and —$CH_2NHCH_3$; and $R_2$ is selected from the group consisting of H and —$NH_2$, provided that $R_1$ and $R_2$ are not both H.

In some preferable embodiments, $R_3$ is selected from the group consisting of H and Br.

In some preferable embodiments, $R_5$ and $R_6$ are each independently selected from the group consisting of H, hydroxyl, and F.

In some particularly specific preferable embodiments, the compound of Formula (I) of the present application is selected from the group consisting of:

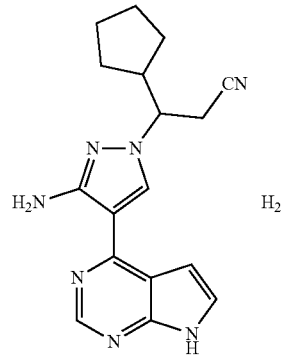

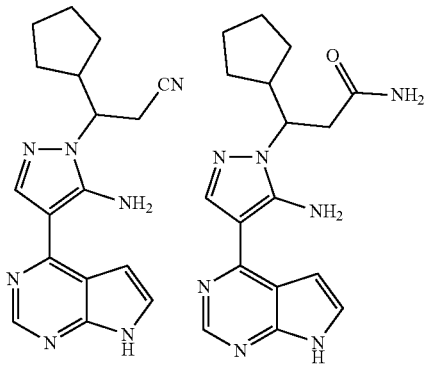

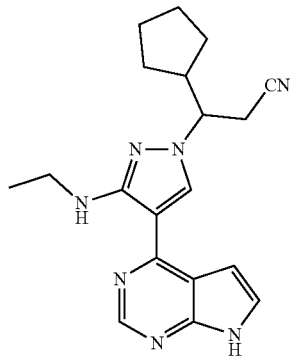

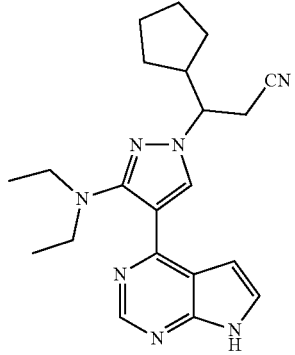

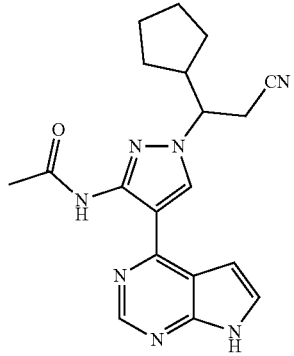

13
-continued
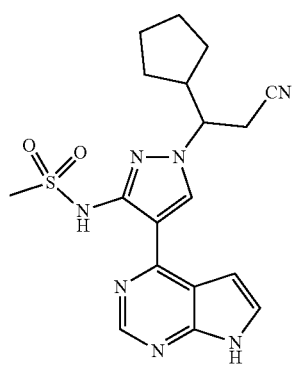
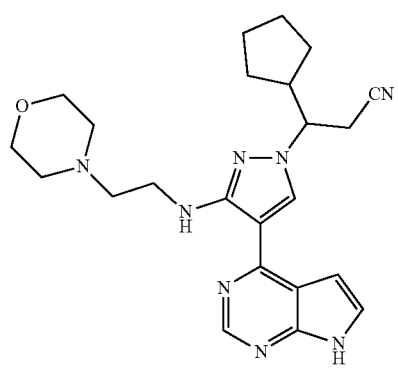
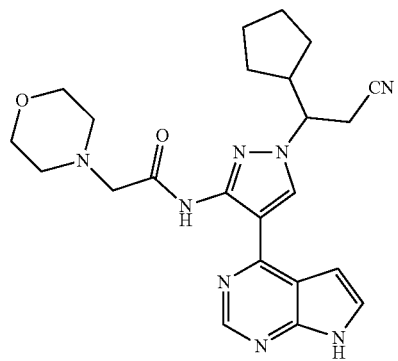
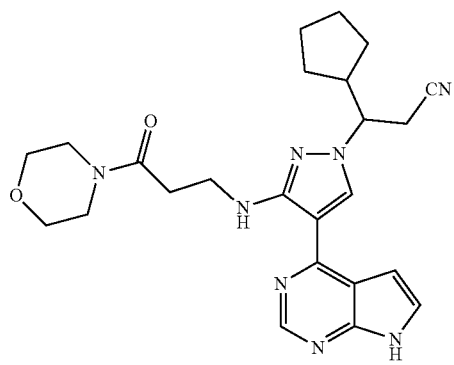
14
-continued
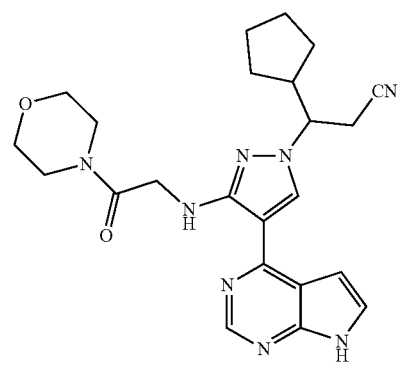
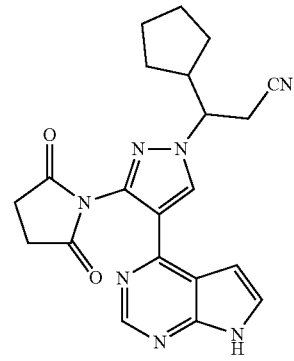
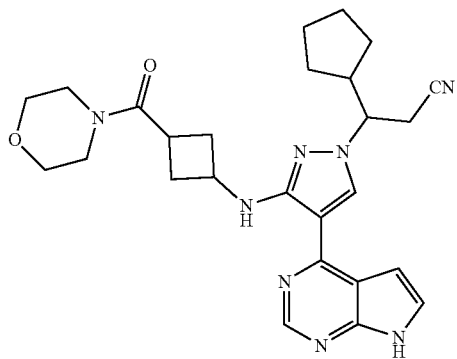 [SMILES: N#CCC(C1CCCC1)n1cc(-c2ncnc3[nH]ccc23)c(NC2CC(C(=O)N3CCOCC3)C2)n1]

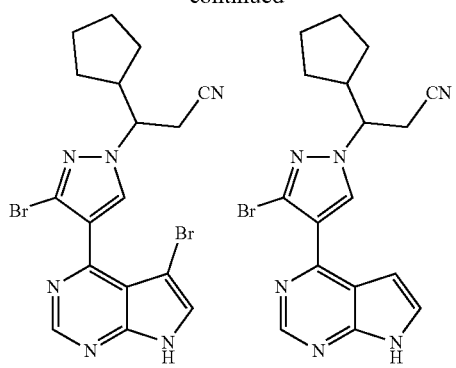
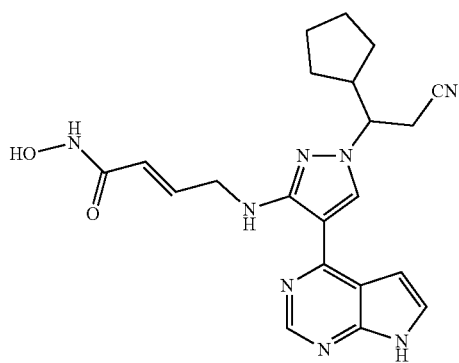
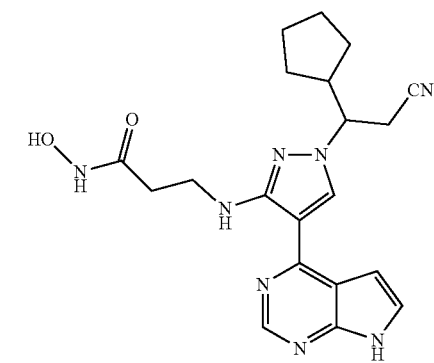
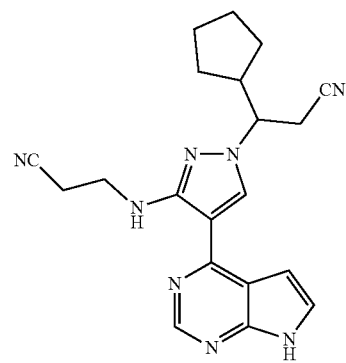
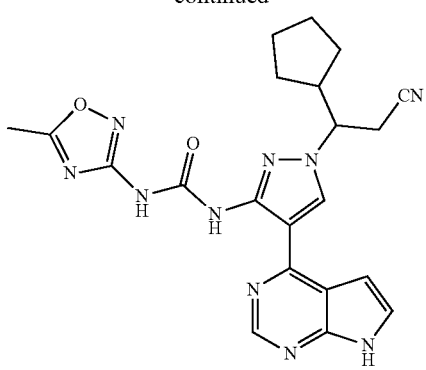
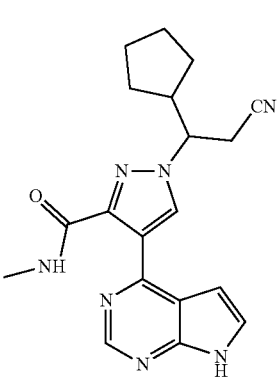
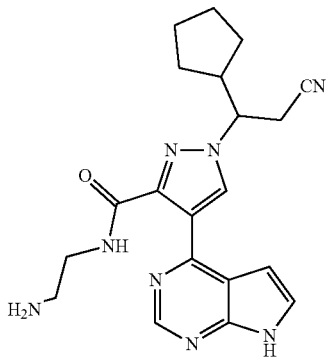
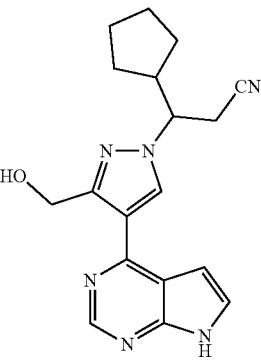

-continued
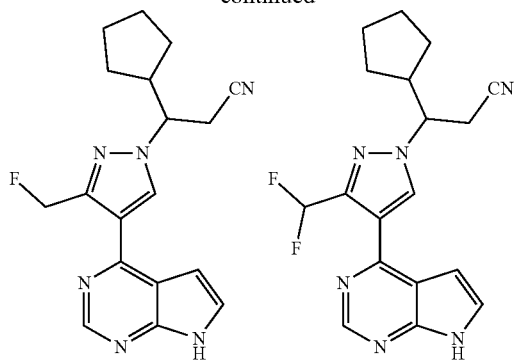
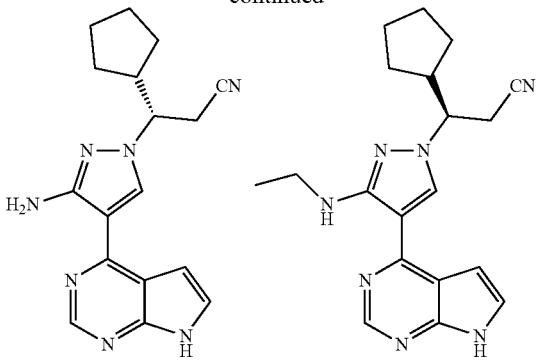
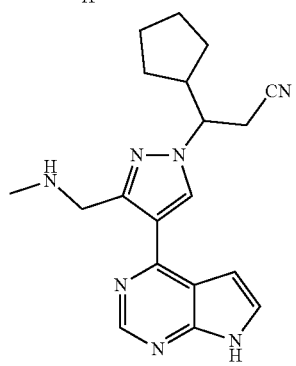
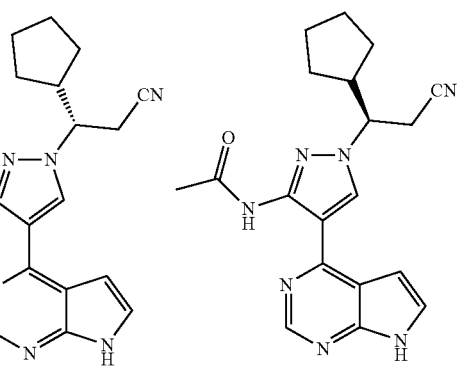
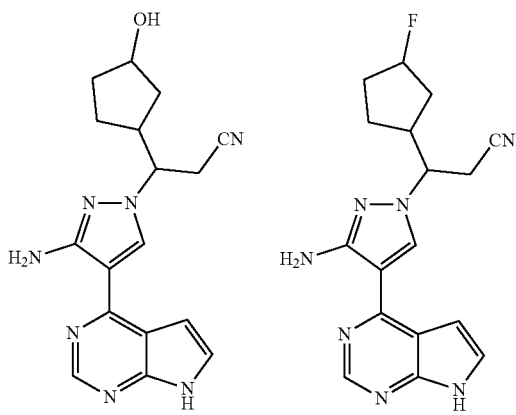
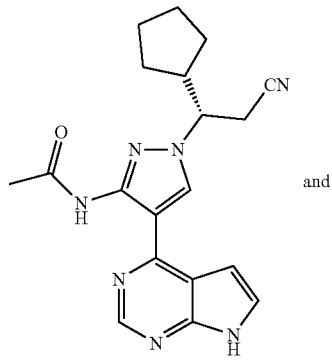
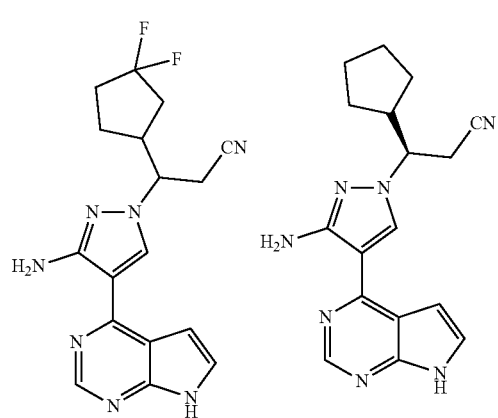
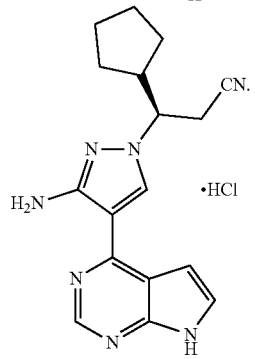
and
·HCl
As a preferable embodiment for the compound of Formula (I) of the present application, provided is the compound represented by Formula (Ia), a stereoisomer thereof, or a pharmaceutically acceptable salt thereof, as shown below:

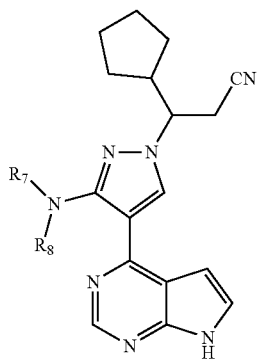

Ia wherein, R₇ and R₈ are each independently selected from the group consisting of H, $C_{1-6}$alkyl, $C_{1-6}$alkylacyl, and $C_{1-6}$alkylsulfonyl.

As a preferable embodiment for the compound represented by Formula (Ia), R₇ and R₈ are each independently selected from the group consisting of H, methyl, ethyl, propyl, butyl, pentyl, hexyl, formyl, acetyl, propionyl, butyryl, valeryl, hexanoyl, methylsulfonyl, ethylsulfonyl, propylsulfonyl, butylsulfonyl, pentylsulfonyl, and hexylsulfonyl.

As a preferable embodiment for the compound represented by Formula (Ia), R₇ is selected from H, and R₈ is selected from the group consisting of methyl, ethyl, propyl, butyl, pentyl, hexyl, formyl, acetyl, propionyl, butyryl, valeryl, hexanoyl, methylsulfonyl, ethylsulfonyl, propylsulfonyl, butylsulfonyl, pentylsulfonyl, and hexylsulfonyl.

In some particularly specific preferable embodiments, the compound of Formula (Ia) of the present application is selected from the group consisting of:

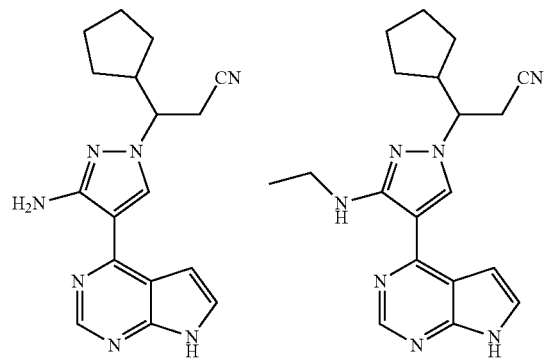

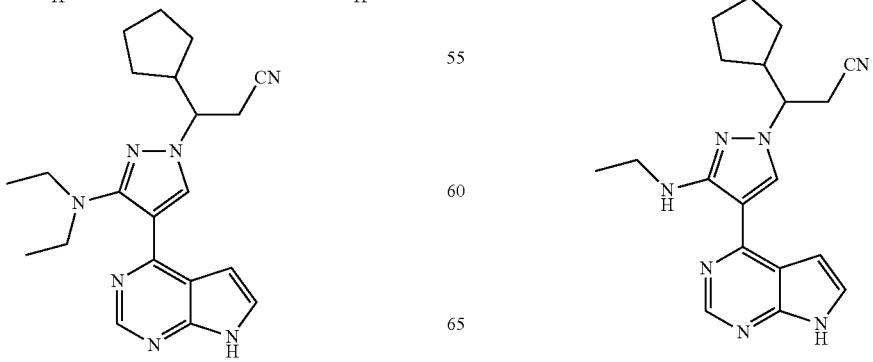

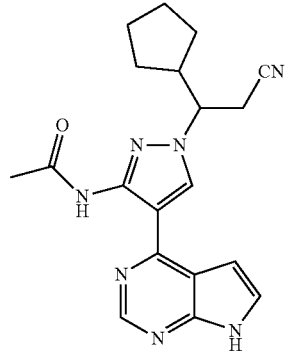

and

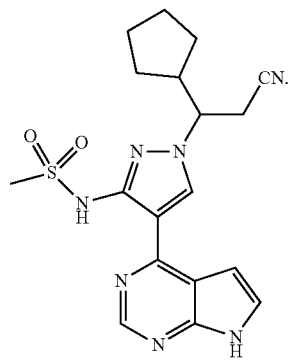

In further particularly preferable embodiments, the compound of Formula (I) of the present application is selected from the group consisting of:

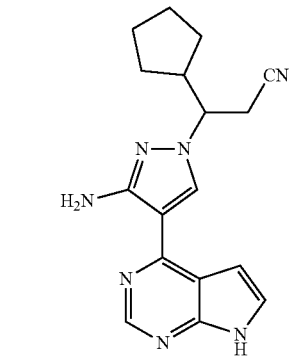

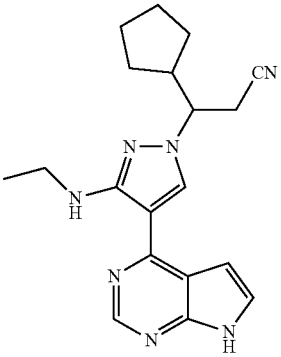

and

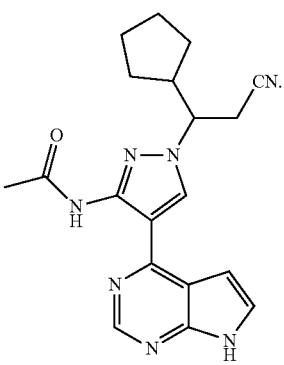

In some embodiments, the stereoisomer of the compound of Formula (I) is particularly preferably selected from the group consisting of:

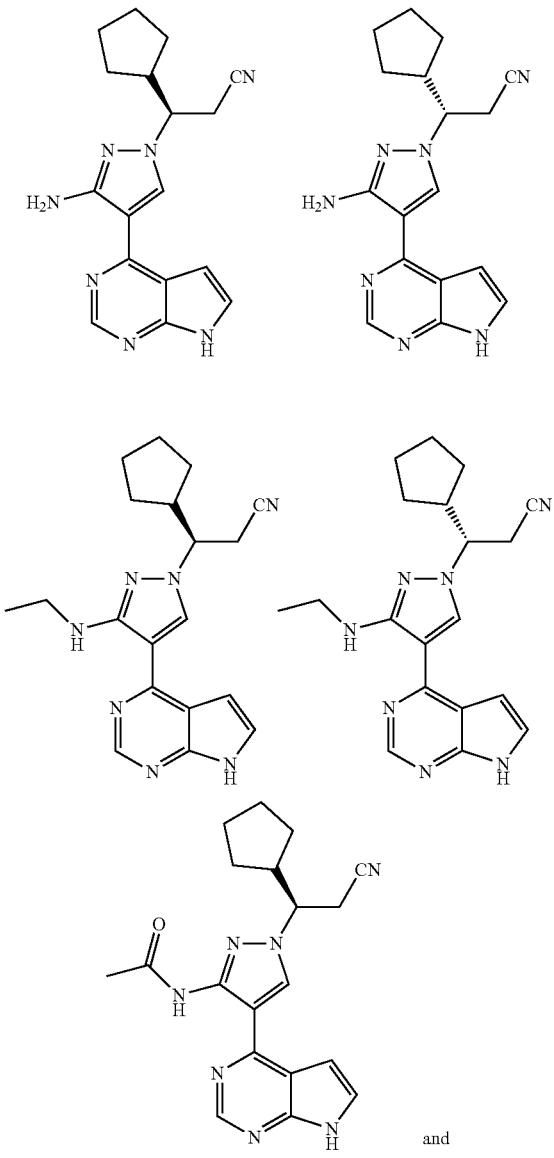

and

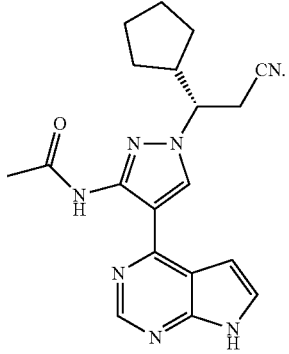

Definitions

Unless specified otherwise, the following terms used herein have the following meanings. If a particular term or phrase is not specifically defined, it cannot be considered to be indefinite or unclear, and shall be understood according to the ordinary meaning in the art. Where a trade name is cited herein, it is intended to indicate the corresponding product or its active ingredient.

The term "optional" or "optionally" is intended to mean that the subsequently described event or circumstance may or may not occur, and that the description includes instances where said event or circumstance occurs and instances where said event or circumstance does not occur. For example, when ethyl is "optionally" substituted with halo, it is intended to mean that ethyl may be un-substituted ($CH_2CH_3$), mono-substituted (e.g., $CH_2CH_2F$), poly-substituted (e.g., $CHFCH_2F$, $CH_2CHF_2$, etc), or fully substituted ($CF_2CF_3$). It will be understood by those skilled in the art with respect to any group containing one or more substituents that such groups are not intended to introduce any substitution or substitution patterns which are sterically impractical and/or synthetically non-feasible.

"$C_{m\sim n}$" as used herein means there are m-n carbon atoms in the moiety. For example, "$C_{1\sim8}$alkyl" means there are 1~8 carbon atoms in the alkyl group.

The numerical range as used herein refers to each integer within the given range. For example, "$C_{1\sim8}$" means that the group may have one carbon atom, two carbon atoms, three carbon atoms, four carbon atoms, five carbon atoms, six carbon atoms, seven carbon atoms, or eight carbon atoms.

The term "substituted" is intended to mean that any one or more hydrogen atoms on the specific atom is substituted with substituent(s), as long as the valence state of the specific atom is normal and the substituted compound is stable. When the substituent is oxo (i.e., =O), it is intended to mean that two hydrogen atoms are substituted, and the oxo will not occur in an aromatic group.

When any variable (e.g., R) occurs in the composition or structure of a compound more than once, the variable is independently defined in each case. Therefore, for example, if a group is substituted with 0-2 Rs, the group may be optionally substituted with up to two Rs, and in each case, R is independently selected. In addition, the combination of substituents and/or variants thereof is allowed if such a combination will result in a stable compound.

The term "halo" refers to fluorine, chlorine, bromine, or iodine.

The term "hydroxyl" refers to —OH group.
The term "cyano" refers to —CN group.
The term "oxo" refers to =O group.

The term "amino" refers to —NH$_2$ group, —NH(C$_{1~6}$alkyl) group or —N(C$_{1~6}$alkyl)$_2$ group. The specific examples of the amino group include, but not limited to, —NH$_2$, —NHCH$_3$, —N(CH$_3$)$_2$, —NHC$_2$H$_5$, —N(C$_2$H$_5$)$_2$, —N(C$_3$H)$_2$, —N(CH$_3$)C$_2$H$_5$ and the like.

The term "alkyl" refers to a straight or branched saturated aliphatic hydrocarbon group consisting of carbon atoms and hydrogen atoms, which is attached to the rest of the molecule via a single bond. Non-limiting examples of this term includes methyl, ethyl, propyl, butyl, pentyl, hexyl, heptyl, octyl, nonyl, decyl, —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), and the like. The term "C$_{1~8}$alkyl" refers to an alkyl having 1~8 carbon atoms. The term "C$_{1~6}$alkyl" refers to an alkyl having 1~6 carbon atoms. The term "C$_{1~4}$alkyl" refers to an alkyl having 1~4 carbon atoms. The "alkyl", "C$_{1~8}$alkyl", "C$_{1~6}$alkyl" or "C$_{1~4}$alkyl" may be unsubstituted or substituted with one or more substituents selected from the group consisting of hydroxyl, halo, and amino.

A group composed of a literal description, which indicates the carbon atom number, such as "prop-", "but-", "pent-" and the like, and a functional group, includes all isomers thereof, for example, 1) butyl group includes CH$_3$CH$_2$CH$_2$—, (CH$_3$)$_2$CH—; 2) butyryl group includes CH$_3$CH$_2$CH$_2$CO—, (CH$_3$)$_2$CHCO—.

The term "alkylene" refers to a straight or branched saturated aliphatic hydrocarbon group consisting of carbon atoms and hydrogen atoms, which is attached to the rest of the molecule via two bonding sites. Non-limiting examples of this term include methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—), and the like. The term "C$_{1~6}$alkylene" refers to an alkylene having 1-6 carbon atoms. The term "C$_{1~4}$alkylene" refers to an alkylene having 1-4 carbon atoms.

The term "cycloalkylene" refers to a saturated cycloalkane, which is attached to the rest of the molecule via two binding sites. Non-limiting examples of this term include 1,2-cyclopropylene

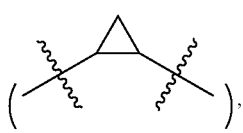

1,1-cyclopropylene

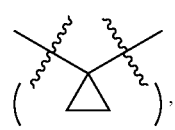

1,3-cyclobutylene

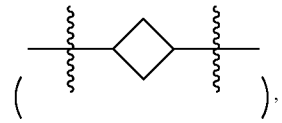

1,1-cyclobutylene

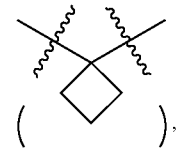

1,3-cyclopentylene

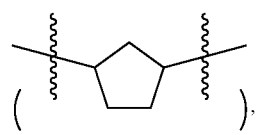

1,3-cyclohexylene

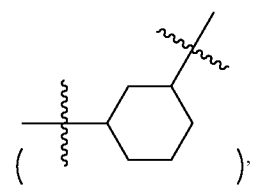

1,4-cyclohexylene

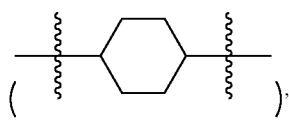

and the like. The term "C$_{3~6}$cycloalkylene" refers to a cycloalkylene having 3~6 carbon atoms. The term "C$_{3~5}$cycloalkylene" refers to a cycloalkylene having 3~5 carbon atoms.

The term "alkenylene" refers to a straight or branched unsaturated aliphatic hydrocarbon group consisting of carbon atoms and hydrogen atoms and containing at least one double bond, which is attached to the rest of the molecule via two bonding sites. Non-limiting examples of "alkenylene" include, but not limited to, 1,2-vinylene (—CH═CH—), 1,3-propenylene (—CH═CH—CH$_2$—), 1,4-but-2-enylene (—CH$_2$—CH═CH—CH$_2$—), and the like. The term "C$_{2~6}$alkenylene" refers to an alkenylene having 2~6 carbon atoms. The term "C$_{2~4}$alkenylene" refers to an alkenylene having 2~4 carbon atoms.

The term "alkylacyl" refers to a group formed by connecting an alkyl with —CO—, and non-limiting examples thereof include formyl, acetyl, propionyl, butyryl, and the like. The term "C$_{1~6}$alkylacyl" refers to a group formed by connecting $C_{1\sim6}$alkyl with —CO—. The term "$C_{1\sim4}$alkylacyl" refers to a group formed by connecting $C_{1\sim4}$alkyl with —CO—.

The term "alkylsulfonyl" refers to a group formed by connecting an alkyl with —SO$_2$—, and non-limiting examples thereof include methylsulfonyl, ethylsulfonyl, propylsulfonyl, butylsulfonyl, and the like. The term "$C_{1\sim6}$alkylsulfonyl" refers to a group formed by connecting $C_{1\sim6}$alkyl with —SO$_2$—. The term "$C_{1\sim4}$alkylsulfonyl" refers to a group formed by connecting $C_{1\sim4}$alkyl with —SO$_2$—.

The term "heteroaryl" refers to a monocyclic or fused polycyclic system, which contains at least one ring atom selected from N, O or S and the other ring atoms are C, and has at least one aromatic ring. Non-limiting examples of "heteroaryl" include, but not limited to, pyrrolyl, furyl, thienyl, imidazolyl, oxazolyl, 1,2,4-oxadiazolyl, pyrazolyl, pyridyl, pyrimidyl, pyrazinyl, quinolyl, isoquinolyl, tetrazolyl, triazolyl, triazinyl, benzofuryl, benzothienyl, indolyl, isoindolyl, and the like. The term "5- or 6-membered heteroaryl" refers to a heteroaryl having 5~6 ring atoms. The "heteroaryl" or "5- or 6-membered heteroaryl" may be unsubstituted or substituted with one or more substituents selected from the group consisting of hydroxyl, halo, and $C_{1\sim4}$alkyl.

The term "heterocyclyl" refers to a nonaromatic monocyclic, fused polycyclic, bridged or spiro ring system, wherein a part of ring atoms may be heteroatom(s) selected from N, O, S(O)$_n$ (wherein, n is 0, 1 or 2), and the other ring atoms are C. Such ring may be saturated or unsaturated (e.g., having one or more double bonds), but do not have completed conjugated 2-electron system. Non-limiting examples of "heterocyclyl" include oxiranyl, thiiranyl, aziranyl, azetidinyl, oxetanyl, thietanyl, tetrahydrofuranyl, pyrrolidinyl, oxazolidinyl, tetrahydropyrazolyl, pyrrolinyl, dihydrofuranyl, dihydrothienyl, piperidinyl, tetrahydropyranyl, tetrahydrothiapyranyl, morpholinyl, piperazinyl, dihydropyridyl, tetrahydropyridyl, dihydropyranyl, tetrahydropyranyl, dihydrothiapyranyl, azacycloheptyl, oxacycloheptyl, thiacycloheptyl, oxa-azabicyclo[2.2.1]heptyl, azaspiro[3.3]heptyl, and the like. The term "5- or 6-membered heterocyclyl" refers to a heterocyclyl having 5~6 ring atoms. The "heterocyclyl" or "5- or 6-membered heterocyclyl" may be unsubstituted or substituted with one or more substituents selected from the group consisting of hydroxyl, halo, $C_{1\sim4}$alkyl, and oxo.

The term "pharmaceutically acceptable" refers to those compounds, materials, compositions and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

For example, a metal salt, an ammonium salt, a salt formed with an organic base, a salt formed with an inorganic acid, a salt formed with an organic acid, a salt formed with an alkaline or acidic amino acid, and the like can be mentioned as a pharmaceutically acceptable salt. Non-limiting examples of a metal salt include, but not limited to, a salt of alkali metal, such as sodium salt, potassium salt, and the like; a salt of alkali earth metal, such as calcium salt, magnesium salt, barium salt, and the like; aluminum salt, and the like. Non-limiting examples of a salt formed with an organic base include, but not limited to, those salts formed with trimethylamine, triethylamine, pyridine, methylpyridine, 2,6-dimethylpyridine, ethanol amine, diethanol amine, triethanol amine, cyclohexylamine, dicyclohexylamine, and the like. Non-limiting examples of a salt formed with an inorganic acid include, but not limited to, those salts formed with hydrochloric acid, hydrobromic acid, nitric acid, sulfuric acid, phosphoric acid, and the like. Non-limiting examples of a salt formed with an organic acid include, but not limited to, those salts formed with formic acid, acetic acid, trifluoroacetic acid, fumaric acid, oxalic acid, malic acid, maleic acid, tartaric acid, citric acid, succinic acid, methanesulfonic acid, benzenesulfonic acid, p-methylbenzene sulfonic acid, and the like. Non-limiting examples of a salt formed with an alkaline amino acid include, but not limited to, those salts formed with arginine, lysine, omithine, and the like. Non-limiting examples of a salt formed with an acidic amino acid include, but not limited to, those salts formed with aspartic acid, glutamic acid, and the like.

The pharmaceutically acceptable salt as used herein can be synthesized from a parent compound containing an acid radical or a base radical through a conventional chemical process. In general, the process for preparing such a salt comprises: reacting these compounds in the form of a free acid or base with stoichiometric appropriate base or acid in water or an organic solvent or a mixture of water and an organic solvent, and then separating a solid of salt product from the reaction solution. However, other processes for forming a salt can be used. In general, non-aqueous medium, such as ether, ethyl acetate, ethanol, isopropanol, acetonitrile and the like, is preferable.

Some of the compounds in the present application may exist as non-solvate form or solvate form, including hydrate form. In general, the solvate form is comparative to the non-solvate form, and both of them are contemplated by the present invention. Some of compounds in the present application may exist as polycrystal or amorphous form.

Some of compounds in the present application may have unsymmetrical carbon atom (optical center) or double bond. Racemate, diastereoisomer, geometrical isomer and individual isomer are all included within the scope of the present invention.

The graphical representations for racemic, ambiscalemic and scalemic, or enantiomerically pure compounds herein are obtained from Maehr, J. Chem. Ed. 1985, 62: 114-120. Unless specified otherwise, the wedge shaped bond and dotted line bond are used to represent the absolute configuration of a stereoscopic center. Where the compounds herein contain an olefinic double bond or other geometrically unsymmetrical center, unless specified otherwise, they comprise E-, Z-geometrical isomers. Similarly, the tautomer forms are all included within the scope of the present invention.

The compounds of the present application may have particular geometrical isomers or stereoisomer forms. Such compounds are all contemplated in the present application, including cis- and trans-isomers, Z- and E-isomers, (−)- and (+)-enantiomers, (R)- and (S)-enantiomers, diastereoisomers, (D)-isomers, (L)-isomers, and racemic mixtures thereof and other mixtures, such as a enantiomer or diastereoisomer-rich mixture. All such mixtures are included within the scope of the present invention. Substituents such as alkyl group may have additional unsymmetrical carbon atoms. Such isomers and mixtures thereof are all included within the scope of the present invention.

Optically active (R)- and (S)-isomers and D- and L-isomers can be prepared by using chiral resolution, chiral synthesis or chiral reagents, or other conventional technology. If one enantiomer of certain compound of the present application is desired, this enantiomer can be prepared by an asymmetric synthesis or a derivatization process with a chiral adjuvant, which comprises separating a mixture of diastereoisomers, and cleaving assistant groups to provide a desired pure enantiomer. Alternatively, when the molecule contains an alkaline functional group (such as amino group) or an acidic functional group (such as carboxyl group), a diastereoisomer salt can be formed by the molecule and an appropriate optically active acid or base, then the diastereoisomer is resolved by a fractional crystallization or chromatography as well-known in the art, thereby recovering a pure enantiomer. In addition, the separation of an enantiomer and a diastereoisomer is generally achieved by a chromatography using a chiral stationary phase, or optionally combining with a chemical derivatization process (e.g., using amine to produce a carbamate salt).

The compound of the present application can contain atomic isotopes at a non-natural ratio, on one or more atoms that constitute the compound. For example, the compound can be labeled with a radioactive isotope, such as tritium ($^3H$), iodine-125 ($^{125}I$) or carbon-14 ($^{14}C$). The transformations formed by all the isotopes for the compound of the present application, whether they are radioactive or not, are all contemplated by the present application.

The compound of the present application also contains the prodrug of the compound herein. The term "prodrug" as used herein refers to any covalently bonded carriers that release the active parent compound when such prodrug is administered to a mammal patient. The prodrug can be prepared by modifying functional groups present in the compound in such a way that the prodrug can be converted into the parent compound, by a routine manipulation or in vivo. Prodrug includes a compound, e.g., wherein hydroxyl, amino, mercapto or carboxyl group is bonded to any groups, and when the prodrug is administered to a mammal patient, will cleave to form free hydroxyl, free amino, free mercapto or free carboxyl group, respectively. Examples of the prodrug include, but not limited to, acetate, formate and benzoate derivatives of the alcohol functional group in the compounds of the present invention, or methyl amine and ethyl amine derivatives of the amino functional group in the compounds of the present invention.

The compounds of the present application can be prepared by various synthesis processes well-known to a person skilled in the art, including the specific embodiments illustrated in the following description, the embodiments obtained by combining the specific embodiments with other chemical synthesis processes, as well as equivalent embodiments well-known to the skilled person in the art. The preferable embodiments include, but not limited to, the Examples of the present application.

The chemical reactions in the specific embodiments of the present application are carried out in appropriate solvents that must be suitable for chemical modification of the present application, as well as the reagents and materials needed in such modification. In order to obtain the compounds of the present application, a person skilled in the art sometimes need to modify or select synthesis steps or reaction processes on the basis of the existing embodiments.

It is one important consideration factor for any synthesis scheme in the art to select appropriate protecting groups for the reactive functional groups (such as the amino group in the present application). As for any trained practitioner, Greene and Wuts, Protective Groups In Organic Synthesis, Wiley and Sons, 1991, is authoritative in this aspect. All references cited in the present application are incorporated herein by reference in their entirety.

The reactions herein can be monitored according to any known suitable methods in the art. For example, the formation of a product can be monitored by broad spectrum methods, for example, nuclear magnetic resonance spectroscopy (such as $^1H$ or $^{13}C$), infrared spectroscopy, spectrophotometry (such as UV-visible light) or mass spectrography, or by chromatography, for example, high performance liquid chromatography (HPLC) or thin layer chromatography.

Some of the compounds of Formula (I) of the present application can be prepared by a person skilled in the art of organic synthesis art via a standard process in the art according to Scheme 1:

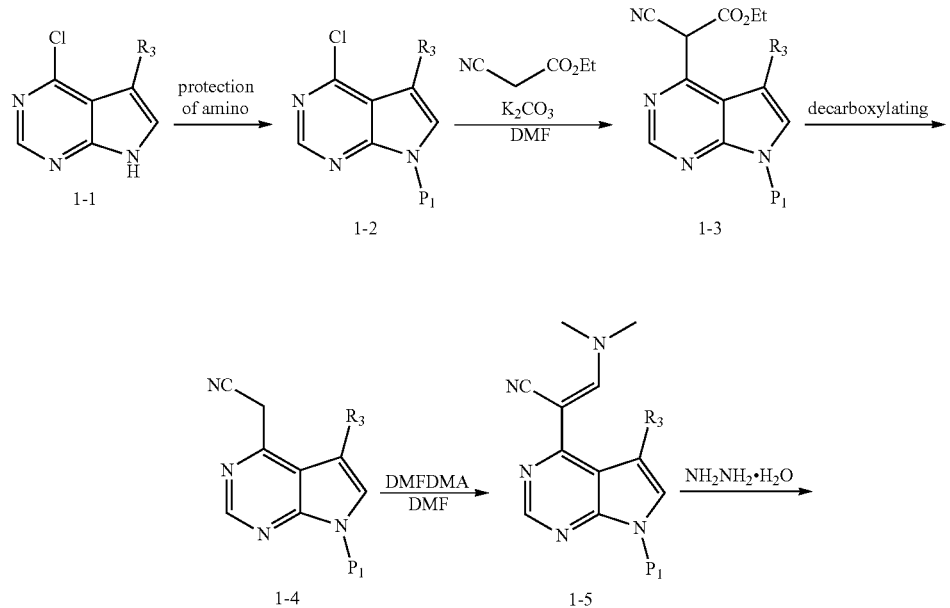

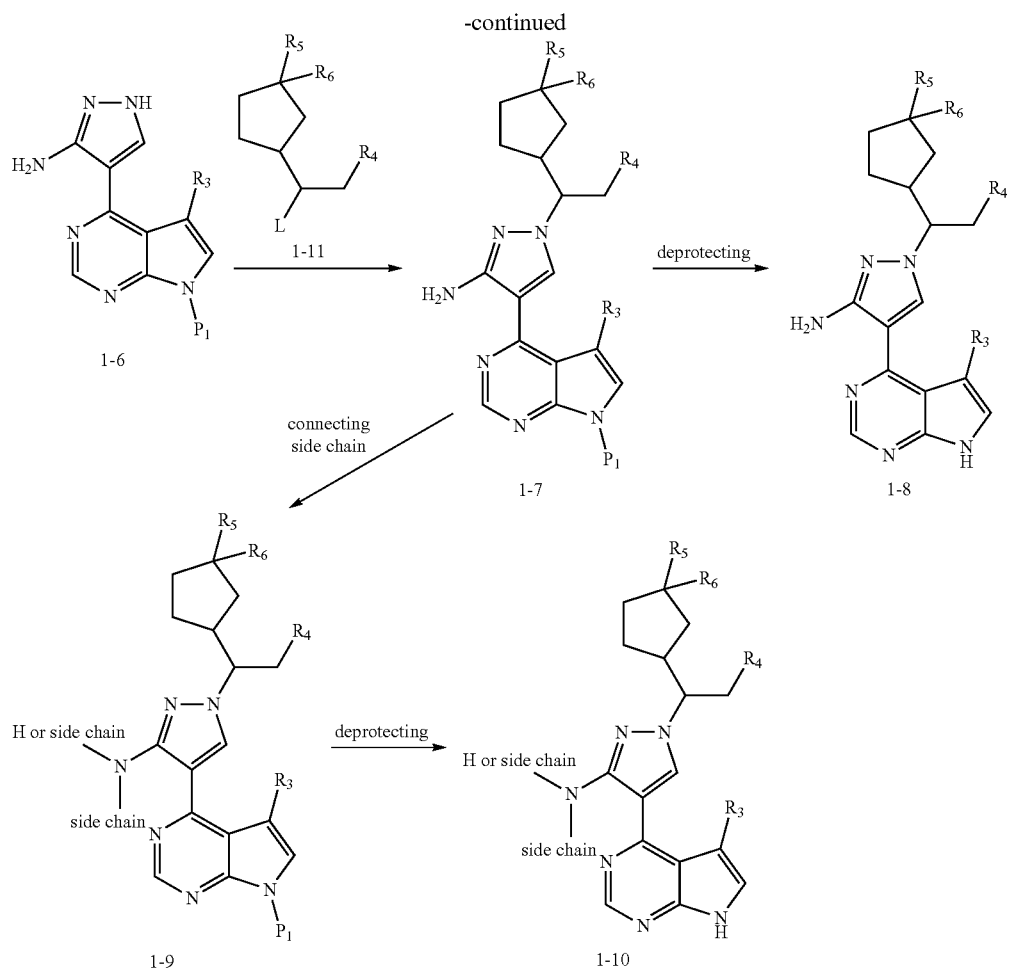

As shown in Scheme 1, the compounds 1-8 and 1-10 containing the amino-substituted pyrazolyl core can be synthesized from pyrrolo[2,3-b]pyrimidine as a starting material. The amino group of the compound 1-1 can be protected with an appropriate protecting group ($P_1$) to obtain the compound 1-2, which is reacted with ethyl cyanoacetate to produce the compound 1-3; the compound 1-3 is subjected to decarboxylation to produce the compound 1-4, which is then reacted with N,N-dimethylformamide dimethylacetal (DMF-DMA) to produce the compound 1-5; the compound 1-5 is reacted with hydrazine hydrate, and then cyclized to produce the compound 1-6 containing the amino-substituted pyrazolyl core, which can be further reacted with the reagent 1-11 (wherein L is a leaving group) to produce the compound 1-7; the protecting group in the compound 1-7 is deprotected to produce the compound 1-8 of the present application. The compound 1-7 is connected with various side chains to produce the compound 1-9, which is deprotected to produce the compound of the present application containing an amino-substituted pyrazole.

Some of the compounds of Formula (I) of the present application can also be prepared by a person skilled in the organic synthesis art via a standard process in the art according to Scheme 2:

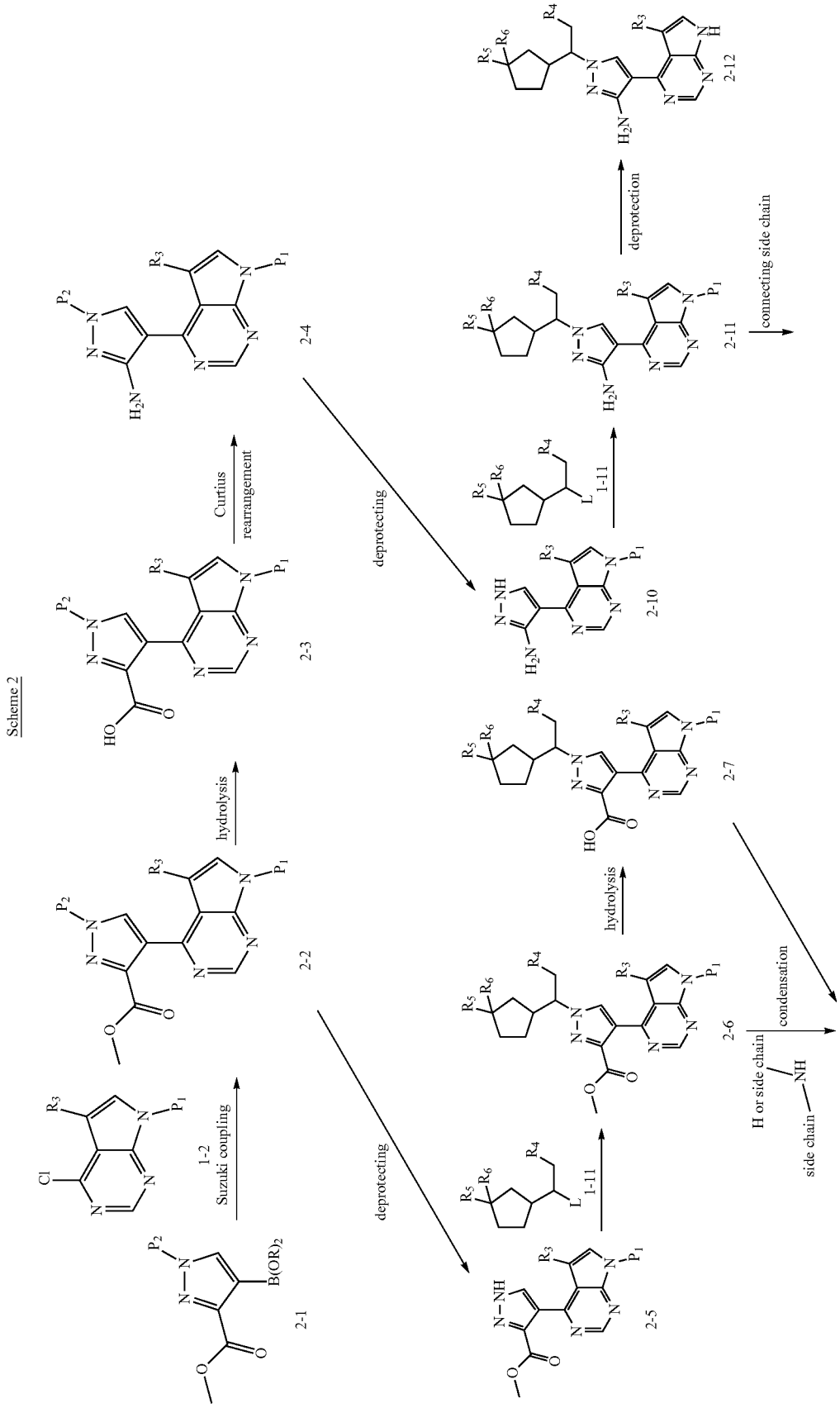

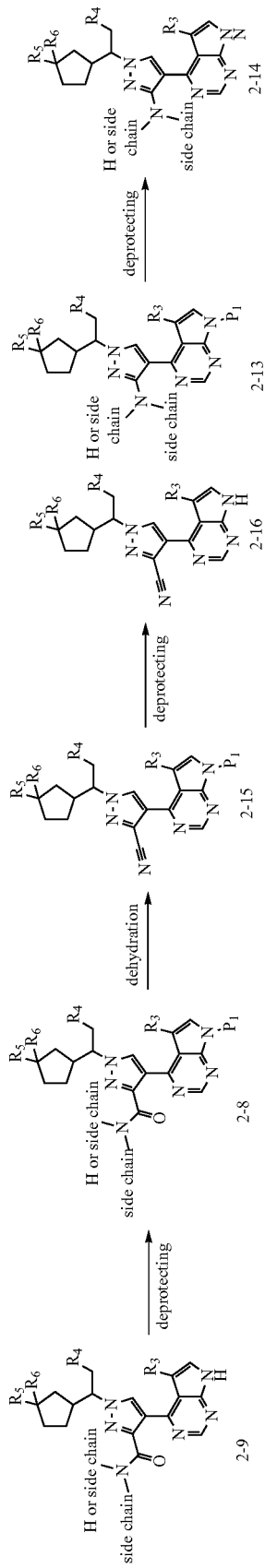

As shown in Scheme 2, the compounds 2-14, 2-9 and 2-16 containing the amino/aminoacyl/cyano-substituted pyrazolyl core can be synthesized from ester group-substituted pyrazole 2-1 ($P_2$ is a protecting group) as a starting material. The compound 2-1 is reacted with the compound 1-2 by Suzuki coupling reaction to produce the compound 2-2, which is subjected to hydrolysis and Curtius rearrangement to produce amino-substituted pyrazole compound 2-4; the protecting group on pyrazolyl of the compound 2-4 is deprotected to produce the compound 2-10, which is reacted with the reagent 1-11 (wherein L is a leaving group) to produce the compound 2-11; the compound 2-11 can be deprotected to produce the compound 2-12 of the present application, or can be deprotected after connecting a side chain to amino group to produce the compound 2-14 of the present application. The compound 2-2 can be deprotected, and then reacted with the reagent 1-11 (wherein L is a leaving group) to produce the compound 2-6, which is subjected to hydrolysis, then condensation with an amine, or direct reaction with an amine to produce the compound 2-8. The compound 2-8 can be deprotected to produce the amido-substituted compound 2-9 of the present application, or the amido group is subjected to hydrolysis to produce the cyano-substituted compound 2-15, which is deprotected to produce the compound 2-16 of the present application.

Some of the compounds of Formula (I) of the present application can also be prepared by a person skilled in the organic synthesis art via a standard process in the art according to Scheme 3:

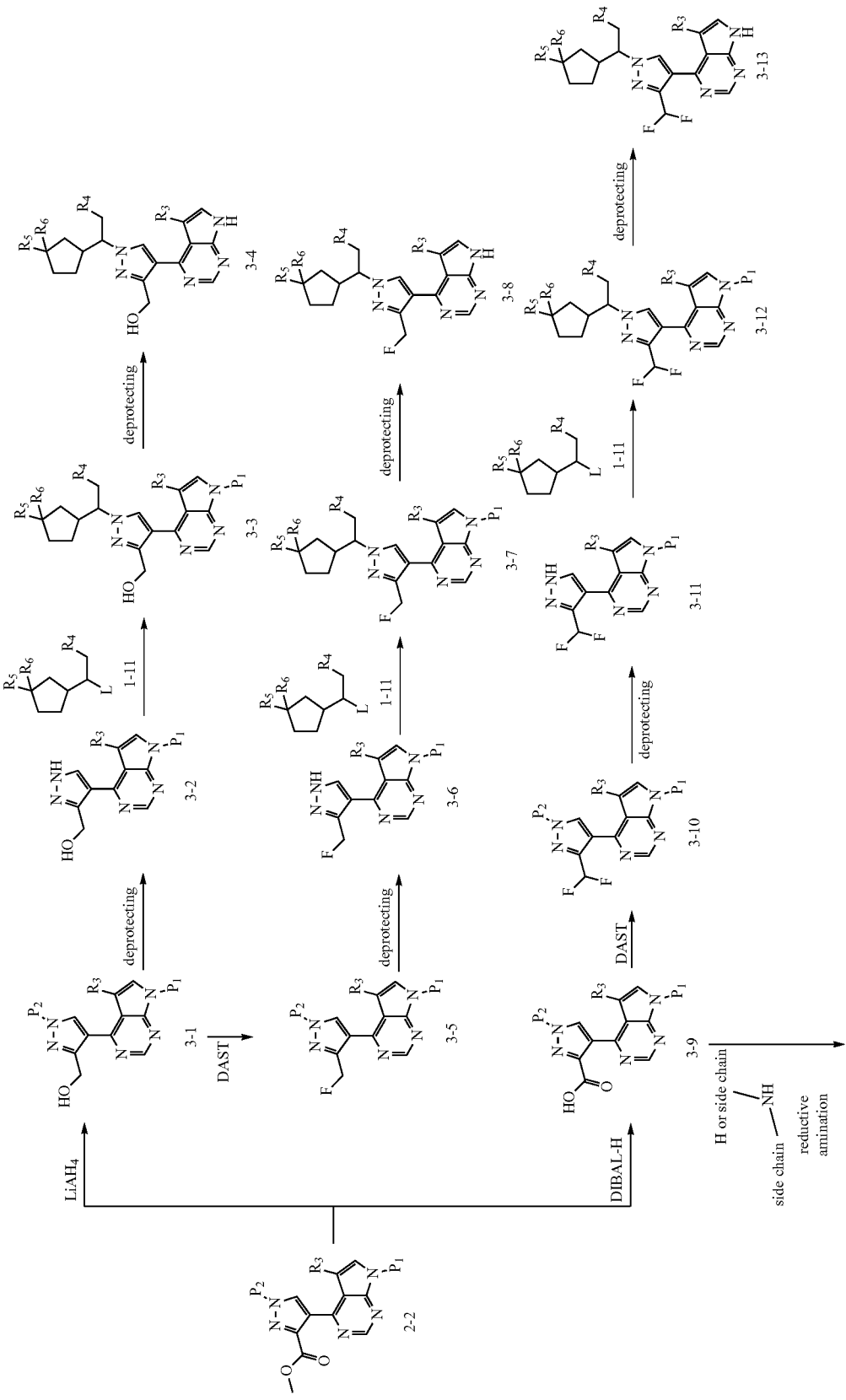

-continued
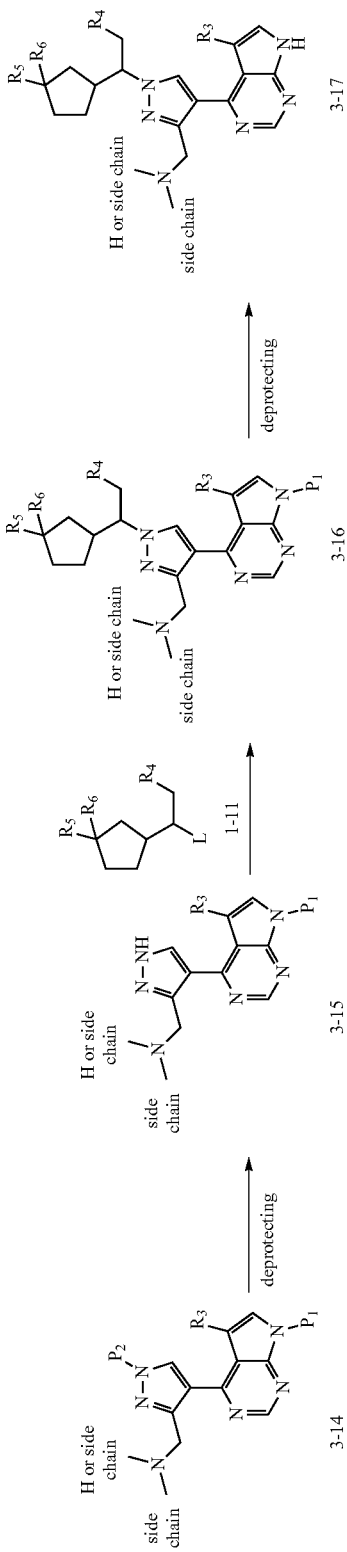

As shown in Scheme 3 the compounds 3-4, 3-8, 313 and 3-17 which contain the hydroxylmethyl/fluoromethyl/difluoromethyl/aminomethyl group can be synthesized from the compound 2-2 in Scheme 2. The ester group substituted compound 2-2 is reduced with lithium aluminum hydride to produce the alcohol 3-1 which is treated with DAST (diethylamino sulfur trifluoride) to produce the fluoro compound 3-5. The compound 2-2 can also be reduced with DIBAL-H (diisobutyl aluminum hydride) to produce the aldehyde group substituted compound 3-9, which can be treated with DAST to produce the difluoro compound 3-10, or subjected to reductive amination reaction to produce the compound 3-14. The obtained intermediates 3-1, 3-5, 3-10 and 3-14 are deprotected, reacted with the compound 1-11 (wherein L is a leaving group), and then deprotected to produce the compounds 3-4, 3-8, 3-13 and 3-17 of the present application, respectively.

Some of the compounds of Formula (I) of the present application can also be prepared by a person skilled in the organic synthesis art via a standard process in the art according to Scheme 4:

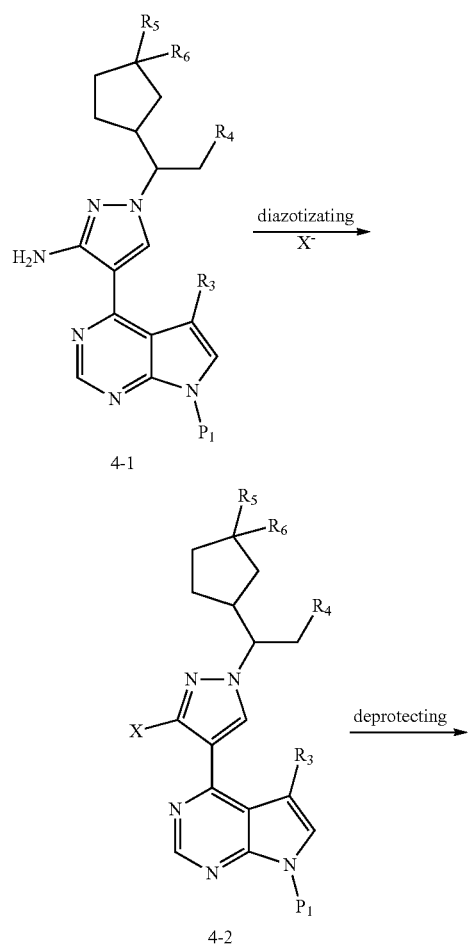

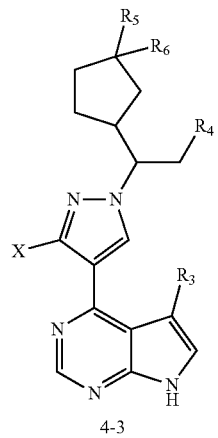

As shown in Scheme 4, the compound 4-3 containing the halo group can be synthesized from the compound 4-1 (i.e., the compound 1-7 in Scheme 1 or the compound 2-11 in Scheme 2). The compound 4-1 is subjected diazotization and halogenation to produce the compound 4-2, and the protecting group on amino group of the compound 4-2 is deprotected to produce the compound 4-3 of the present application.

In another aspect, the present application provides the use of a compound represented by Formula (I), a stereoisomer thereof, or a pharmaceutically acceptable salt thereof, in the preparation of a medicament for treating a disease mediated by Janus kinase.

In still another aspect, the present application provides a method for treating a disease mediated by Janus kinase, comprising administering to a patient a therapeutically effective amount of a compound represented by Formula (I), a stereoisomer thereof, or a pharmaceutically acceptable salt thereof.

The disease mediated by Janus kinase described in the present application includes, but not limited to, tumor (such as lymphoma, leukemia). Lymphoma described in the present application may include, but not limited to, Hodgkins disease or Non-Hodgkins lymphoma, and the Non-Hodgkins lymphoma includes, but not limited to, B-cell lymphoma and T-cell lymphoma. Leukemia described in the present application includes, but not limited to, acute lymphoblastic leukemia, chronic lymphocytic leukemia, acute myeloid leukemia, and chronic myelocytic leukemia.

The compounds in the examples of the present application exhibit significant JAK inhibitory activity. For example, in one or more tests herein, the compounds exhibit a JAK inhibitory activity of less than 1000 nM, preferably a JAK inhibitory activity of less than 200 nM, more preferably a JAK inhibitory activity of less than 100 nM, and particularly preferably a JAK inhibitory activity of less 20 nM.

Compared with other JAK inhibitors, some representative compounds of the present application also exhibit especially excellent pharmacokinetic properties, and these compounds, as active ingredients, can be administered to a patient at a lower dose, thereby reducing the therapy cost of the patient.

The term "patient" refers to any animals including mammals, preferably mice, rats, other rodents, rabbits, dogs, cats, swine, cattle, sheep, horses, or primates, most preferably human being.

The phrase "therapeutically effective amount" as used herein refers to an amount of an active compound or pharmaceutical agent that elicits the biological or medical response that is being sought in a tissue, system, animal, subject or human being by a researcher, veterinarian, medical doctor or other clinicians, comprising one or more of:

(1) preventing a disease: for example, preventing a disease, disorder or condition in a subject who may be predisposed to the disease, disorder or condition but does not yet experience or display the pathology or symptomatology of the disease;

(2) inhibiting a disease: for example, inhibiting a disease, disorder or condition in a subject who is experiencing or displaying the pathology or symptomatology of the disease, disorder or condition (i.e., preventing the further development of the pathology and/or symptomatology);

(3) ameliorating a disease: for example, ameliorating a disease, disorder or condition in a subject who is experiencing or displaying the pathology or symptomatology of the disease, disorder or condition (i.e., reversing the pathology and/or symptomatology).

In another aspect, the present application provides a pharmaceutical composition comprising a therapeutically effective amount of a compound represented by Formula (I), or a pharmaceutically acceptable salt thereof, and one or more pharmaceutically acceptable carriers or excipients.

When used as a medicine, the compounds of the present application can be administered in the form of pharmaceutical compositions. These compositions can be prepared in a manner well-known in the pharmaceutical art, and can be administered by a variety of routes, depending upon whether a local or systemic treatment is desired and upon the area to be treated. Administration may be topical (for example, transdermal, epidermal, ophthalmic and mucous membranes including intranasal, vaginal and rectal delivery), pulmonary (for example, by inhalation or insufflation of powders or aerosols, including by nebulizer; intratracheal or intranasal), oral or parenteral. Parenteral administration includes intravenous, intraarterial, subcutaneous, intraperitoneal, or intramuscular injection or infusion; or intracranial such as intrathecal or intraventricular administration. Parenteral administration may be in the form of a single large dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, water, powders or oily bases, thickeners and the like may be necessary or desirable. Coated condoms, gloves and the like may also be useful.

The present application also includes a pharmaceutical composition which contains one or more of the compounds of the present application above as active ingredient in combination with one or more pharmaceutically acceptable carriers. During the preparation of the composition of the present application, the active ingredient is typically mixed with an excipient, diluted by an excipient or enclosed within such a carrier in the form of, for example, a capsule, sachet, paper or other container. When the excipient serves as a diluent, it can be a solid, semi-solid, or liquid material, which acts as a vehicle, carrier or medium for an active ingredient. Therefore, the composition can be in the form of tablets, pills, powders, lozenges, sachets, cachets, elixirs, suspensions, emulsions, solutions, syrups, aerosols (a solid or dissolved in a liquid medium); ointments containing, for example, up to 10% by weight of an active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying agents and suspending agents; preserving agents such as methylbenzoate and hydroxyl propyl benzoate; sweetening agents; and flavoring agents. The compositions of the present application can be formulated by employing procedures known in the art, so as to provide quick, sustained or delayed release of the active ingredient after administration to the patient.

The compositions may be formulated in a unit dosage form, each dosage containing from about 5-1000 mg, more typically about 100-500 mg, of the active ingredient. The term "unit dosage form" refers to physically discrete unit suitable as unitary dosage for human patient and other mammals, each unit containing a predetermined quantity of the active material calculated to be able to produce the desired therapeutic effect, and mixed with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing a solid composition such as tablets, the principal active ingredient is mixed with a pharmaceutical excipient to form a solid preformulation composition containing a homogeneous mixture of a compound of the present application. When these preformulation compositions are referred to be homogeneous, it means that the active ingredient is typically dispersed evenly throughout the composition so that the composition can be readily subdivided into equally effective unit dosage forms such as tablets, pills and capsules. This solid preformulation is then subdivided into unit dosage forms of the types described above containing, for example, about 0.1~1000 mg of the active ingredient of the present application.

The tablets or pills of the present application can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intactly through the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms for administration orally or by injection, in which the compounds and compositions of the present application can be incorporated, include aqueous solutions, suitably flavored syrups, aqueous or oil suspensions, and emulsions flavored with edible oils such as cottonseed oil, sesame oil, coconut oil, or peanut oil, as well as elixirs and similar pharmaceutical vehicles.

Compositions for inhalation or insufflation include solutions and suspensions dissolved in pharmaceutically acceptable aqueous or organic solvents, or mixtures thereof, and powders. The liquid or solid composition may contain a suitable pharmaceutically acceptable excipient as described above. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of the compound or composition administered to a patient will vary depending upon what is being administered, the purpose of the administration, such as prophylaxis or therapy, the state of the patient, the manner of administration, and the like. In therapeutic application, the composition can be administered to a patient already suffering from a disease in an amount sufficient to cure or at least partially arrest the symptom of the disease and its complication. Effective dose will depend on the disease condition being treated as well as the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being mixed with a sterile aqueous carrier prior to administration. The pH of the compound preparations typically will be 3~11, more preferably 5~9 and most preferably 7~8. It will be understood that use of certain of the foregoing excipients, carriers, or stabilizers will result in the formation of pharmaceutical salts.

The therapeutic dosage of the compounds of the present application can be determined according to, for example, the particular use for which the treatment is made, the manner of administration of the compound, the health and condition of the patient, and the judgment of the prescribing physician. The proportion or concentration of a compound of the present application in a pharmaceutical composition can vary depending upon a number of factors including dosage, chemical characteristics (e.g., hydrophobicity), and the route of administration. For example, the compound of the present application can be provided in an aqueous physiological buffer solution containing about 0.1~10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and progression extent of the disease or condition, the overall health status of the particular patient, the relative biological efficacy of the compound selected, formulation of the excipient, and its route of administration. Effective doses can be obtained by extrapolating from dose-response curves derived from in vitro or animal model test systems.

EXAMPLES

The present invention will be described in more detail by way of specific examples. The following examples are provided for illustrative proposes, and are not intended to limit the present invention in any manner. A person skilled in the art will readily recognize that a variety of non-critical parameters may be changed or modified to obtain substantively the same results. The compounds in the following examples are found to be JAK inhibitors according to one or more tests herein.

Example 1: 3-[3-amino-4-(7H-pyrrolo[2,3-d]pyrimidin-4-yl)-1H-pyrazol-1-yl]-3-cyclopentylpropanenitrile

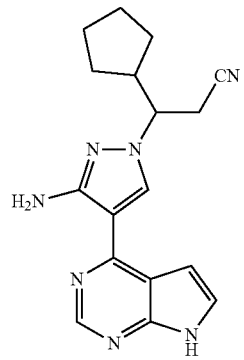

Step A: 3-cyclopentylacrylonitrile

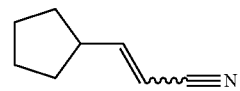

To a solution of 1.0 M potassium tert-butoxide (28.0 g, 250 mmol, 1.2 eq.) in freshly distilled tetrahydrofuran was added dropwise a solution of diethyl cyanomethylphosphonate (44.3 g, 250.0 mmol, 1.2 eq.) in tetrahydrofuran, under stirring in an ice bath. The ice-bath was removed, and the reactants were stirred for 0.5 hr at room temperature. Then, cyclopentanecarbaldehyde (20.0 g, 204 mmol, 1.0 eq.) was added dropwise under the cooling of an ice bath. After the addition was completed, the reactants were stirred overnight at room temperature, then the reaction was quenched by adding water, and the resulting mixture was extracted with ethyl acetate two times. The combined organic phase was washed with brine, dried over sodium sulfate, filtered and concentrated in vacuo. The resulting residue was separated by column chromatography on silica gel column to give 3-cyclopentylacrylonitrile (22.3 g, 91% yield).

$^1$HNMR (400 MHz, CDCl$_3$) δ 6.69 (dd, J=18.8 Hz, J=10.4 Hz, 0.5H, trans-olefins), 6.37 (t, J=10.8 Hz, 0.5H, cis-olefins), 5.29 (d, J=17.6 Hz, 0.5H, trans-olefins), 5.20 (d, J=10.8 Hz, 0.5H, cis-olefins), 3.06-2.99 (m, 0.5H, cis-product), 2.62-2.56 (m, 0.5H, trans-product), 2.04-1.82 (m, 2H), 1.74-1.59 (m, 4H), 1.42-1.26 (m, 2H).

Step B: 4-chloro-7-{[2-(trimethylsilyl)ethoxy]methyl}-7H-pyrrolo[2,3-d]pyrimidine

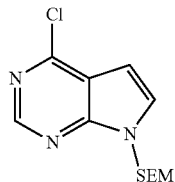 [SMILES: C[Si](C)(C)CCOCn1ccc2c(Cl)ncnc21]

To a solution of 4-chloro-7H-pyrrolo[2,3-d]pyrimidine (20.0 g, 130.4 mmol, 1.0 eq.) in dry DMF was added NaH (6.6 g, 57% content, 156.8 mmol, 1.2 eq.), under stirring in an ice bath. After the reactants were stirred for 1 hr at room temperature, SEMCl (26.1 g, 156.5 mmol, 1.2 eq.) was added dropwise under the cooling of an ice bath. After the addition was completed, the reactants were stirred for 1 hr in an ice bath, then the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give 4-chloro-7-{[2-(trimethylsilyl)ethoxy]methyl)}-7H-pyrrolo[2,3-d]pyrimidine (33.43 g, 90.4% yield).

$^1$HNMR (400 MHz, CDCl$_3$) δ 8.67 (s, 1H), 7.39 (d, J=3.6 Hz, 1H), 6.67 (d, J=3.6 Hz, 1H), 5.65 (s, 2H), 3.53 (dd, J=9.2 Hz, J=8.0 Hz, 2H), 0.91 (t, J=8.4 Hz, 2H), 0.00 (s, 9H).
m/z=284[M+1]$^+$.

Step C: ethyl 2-cyano-2-(7-{[2-(trimethylsilyl)ethoxy]methyl)}-7H-pyrrolo[2,3-d]pyrimidin-4-yl) acetate

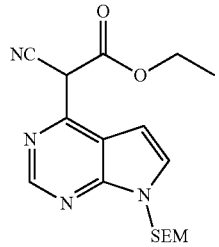 [SMILES: CCOC(=O)C(C#N)c1ncnc2c1ccn2COCC[Si](C)(C)C]

To a mixture of ethyl cyanoacetate (40.1 g, 354.0 mmol, 3.0 eq.) and potassium carbonate (33.0 g, 238 mmol, 2.0 eq.) was added 4-chloro-7-{[2-(trimethylsilyl)ethoxy]methyl}-7H-pyrrolo[2,3-d]pyrimidine (33.5 g, 118 mmol, 1.0 eq.) under stirring at room temperature. The reactants were warmed to 60° C. and reacted for 0.5 hr, then warmed to 130° C. and reacted for 1.0 hr. After the resulting mixture was cooled to room temperature, the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give ethyl 2-cyano-2-(7-{[2-(trimethylsilyl) ethoxy]methyl}-7H-pyrrolo[2,3-d]pyrimidin-4-yl)acetate (30.6 g, 72% yield).

$^1$HNMR (400 MHz, CDCl3): δ 13.87 (brs, 1H), 8.05 (s, 1H), 7.44 (d, J=4.0 Hz, 1H), 7.20 (d, J=3.6 Hz, 1H), 5.57 (s, 2H), 4.30 (dd, J=14.4 Hz, J=7.2 Hz, 2H), 3.5 (t, J=8.4 Hz, 2H), 1.37 (t, J=7.2 Hz, 3H), 0.92 (t, J=8.4 Hz, 2H), 0.00 (s, 9H).
m/z=361 [M+1]$^+$.

Step D: 2-(7-{[2-(trimethylsilyl)ethoxy]methyl}-7H-pyrrolo[2,3-d]pyrimidin-4-yl) acetonitrile

To ethyl 2-cyano-2-(7-{[2-(trimethylsilyl)ethoxy]methyl)}-7H-pyrrolo[2,3-d]pyrimidin-4-yl)acetate (30.6 g, 84.9 mmol, 1.0 eq.) in a mixed solvent of DMSO and water was added sodium chloride (49.7 g, 849.0 mmol, 10.0 eq.) under stirring at room temperature. The reaction liquid was protected with nitrogen gas to react for 5 days at 150° C. After the reaction liquid was cooled to room temperature, the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give 2-(7-{[2-(trimethylsilyl)ethoxy]methyl}-7H-pyrrolo[2,3-d]pyrimidin-4-yl)acetonitrile (18.4 g, 75% yield).

$^1$HNMR (400 MHz, CDCl3) δ 8.87 (s, 1H), 7.40 (d, J=3.6 Hz, 1H), 6.80 (d, J=3.6 Hz, 1H), 5.67 (s, 2H), 4.15 (s, 2H), 3.53 (t, J=8.4 Hz, 2H), 0.92 (t, 8.4 Hz, 2H), 0.01 (s, 9H).
m/z=289[M+1]$^+$.

Step E: 3-(dimethylamino)-2-(7-{[2-(trimethylsilyl)ethoxy]methyl}-7H-pyrrolo[2,3-d]pyrimidin-4-yl) acrylonitrile

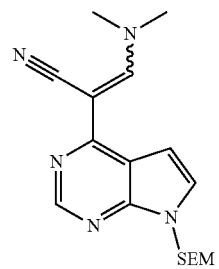 [SMILES: CN(C)C=C(C#N)c1ncnc2c1ccn2COCC[Si](C)(C)C]

To a sealed tube containing DMF solution were added 2-(7-{[2-(trimethylsilyl) ethoxy]methyl}-7H-pyrrolo[2,3-d] pyrimidin-4-yl)acetonitrile (5.3 g, 18.38 mmol, 1.0 eq.) and DMF-DMA (6.57 g, 55.14 mmol, 3.0 eq.). The reaction liquid was stirred overnight at 140° C. After the reaction liquid was cooled to room temperature, the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give 3-(dimethylamino)-2-(7-{[2-(trimethylsilyl)ethoxy]methyl}-7H-pyrrolo[2,3-d]pyrimidin-4-yl)acrylonitrile (3.35 g, 53% yield).

¹HNMR (400 MHz, CDCl₃): δ 8.61 (s, 1H), 8.50 (s, 1H), 7.37 (d, J=3.6 Hz, 1H), 7.27 (d, J=3.6 Hz, 1H), 5.66 (s, 2H), 3.58 (t, J=8.4 Hz, 2H), 3.38 (brs, 6H), 1.04 (t, J=6.8 Hz, 2H), 0.00 (s, 9H).

m/z=344[M+1]⁺.

Step F: 4-(7-{[2-(trimethylsilyl)ethoxy]methyl}-7H-pyrrolo[2,3-d]pyrimidin-4-yl)-3-amino-1H-pyrazole

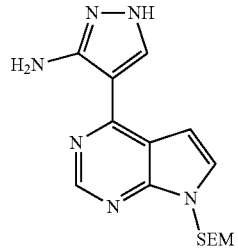 [SMILES: C[Si](C)(C)CCOCn1ccc2c(-c3c[nH]nc3N)ncnc21]

To a solution of 3-(dimethylamino)-2-(7-{[2-(trimethylsilyl)ethoxy]methyl})-7H-pyrrolo[2,3-d]pyrimidin-4-yl) acrylonitrile (1.2 g, 3.5 mmol, 1.0 eq.) in ethanol was added hydrazine hydrate (85%, 2.1 g, 35.6 mmol, 10.0 eq.) under stirring at room temperature. The reaction liquid was protected with nitrogen gas and stirred overnight at 90° C. After the reaction liquid was cooled to room temperature, the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give 4-(7-{[2-(trimethylsilyl)ethoxy]methyl}-7H-pyrrolo[2,3-d]pyrimidin-4-yl)-3-amino-1H-pyrrole (456 mg, 40% yield).

¹HNMR (400 MHz, DMSO-d6) δ 12.20 (brs, 1H), 8.75 (s, 1H), 8.30 (brs, 1H), 7.71 (d, J=3.2 Hz, 1H), 7.11 (d, J=3.6 Hz, 1H), 6.66 (brs, 2H), 5.70 (s, 2H), 3.62 (t, J=8.0 Hz, 2H), 0.93 (t, J=8.0 Hz, 2H), 0.00 (s, 9H).

m/z=331 [M+1]⁺.

Step G: 3-[3-amino-4-(7-{[2-(trimethylsilyl)ethoxy]methyl})-7H-pyrrolo[2,3-d]pyrimidin-4-yl)-1H-pyrazol-1-yl]-3-cyclopentylpropanenitrile 3-[5-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile

G1

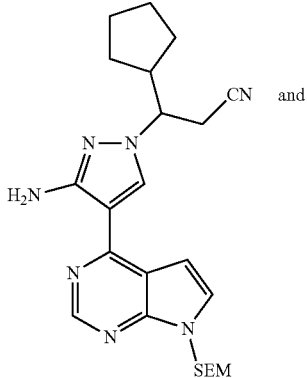

and

G2

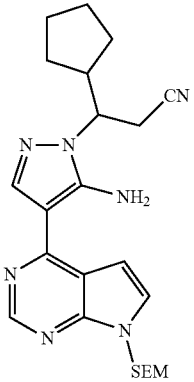

To a solution of 4-(7-{[2-(trimethylsilyl)ethoxy]methyl}-7H-pyrrolo[2,3-d]pyrimidin-4-yl)-3-amino-1H-pyrazole (5.6 g, 16.95 mmol, 1.0 eq.) in acetonitrile was added 3-cyclopentylacrylonitrile (5.176 g, 42.71 mmol, 2.52 eq.) under stirring at room temperature, and then DBU (5.42 g, 35.60 mmol, 2.1 eq.) was added. The reaction liquid was protected with nitrogen gas and stirred overnight at 70° C. After the reaction liquid was cooled to room temperature, the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (4.49 g, 59% yield) and 3-[5-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (1.60 g, 21% yield).

G1: ¹HNMR (400 MHz, CDCl₃) δ 8.79 (s, 1H), 8.01 (s, 1H), 7.34 (d, J=3.6 Hz, 1H), 6.68 (d, J=3.6 Hz, 1H), 5.66 (brs, 4H), 4.00 (t, J=2.0 Hz, 1H), 3.53 (t, J=8 Hz, 2H), 3.08 (dd, J=16.8 Hz, J=8.4 Hz, 1H), 2.89 (dd, J=16.8 Hz, J=3.6 Hz, 1H), 2.53 (s, 1H), 1.95-1.93 (m, 1H), 1.74-1.57 (m, 5H), 1.28-1.22 (m, 2H), 0.92 (dd, J=14 Hz, J=8.4 Hz, 2H), 0.00 (s, 9H).

m/z=452[M+1]⁺.

G2: ¹HNMR (400 MHz, CDCl₃) δ 8.74 (s, 1H), 8.13 (s, 1H), 7.33 (d, J=3.6 Hz, 1H), 6.80 (d, J=3.6 Hz, 1H), 6.12 (brs, 2H), 5.30 (s, 2H), 4.12-4.07 (m, 1H), 3.53 (t, J=8.4 Hz, 2H), 3.14 (dd, J=16.8 Hz, J=9.6 Hz, 1H), 2.90 (dd, J=16.8 Hz, J=4.0 Hz, 1H), 2.60-2.57 (m, 1H), 1.94-1.91 (m, 1H), 1.74-1.54 (m, 5H), 1.34-1.22 (m, 2H), 0.92 (t, J=8.0 Hz, 2H), 0.00 (s, 9H).

m/z=452[M+1]⁺.

Step H: 3-[3-amino-4-(7H-pyrrolo[2,3-d]pyrimidin-4-yl)-1H-pyrazol-1-yl]-3-cyclopentylpropanenitrile

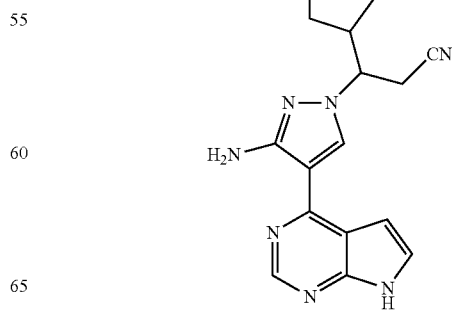

To a solution of 3-[3-amino-4-(7-{[2-(trimethylsilyl) ethoxy]methyl}-7H-pyrrolo[2,3-d]pyrimidin-4-yl)-1H-pyrazol-1-yl]-3-cyclopentylpropanenitrile (3.395 g, 7.52 mmol, 1.0 eq.) in dichloromethane was added trifluoroacetic acid (20 mL) under stirring in an ice bath. The reaction liquid was protected with nitrogen gas and stirred overnight at room temperature. The reaction liquid was concentrated in vacuo, and the residue was dissolved in dichloromethane and again concentrated in vacuo two times. The concentrate was dissolved in methanol, and ethylenediamine (2 mL) was added, then the resulting mixture was stirred overnight. The resulting mixture was concentrated in vacuo, diluted with water and ethyl acetate, and extracted with ethyl acetate. The combined organic phase was washed with brine, dried over sodium sulfate, filtered and concentrated in vacuo. The resulting residue was separated by column chromatography on silica gel column to give 3-[3-amino-4-(7H-pyrrolo[2,3-d]pyrimidin-4-yl)-1H-pyrazol-1-yl]-3-cyclopentylpropanenitrile (1.94 g, 80.0% yield).

¹HNMR (400 MHz, CDCl₃) δ10.45 (s, 1H), 8.79 (s, 1H), 8.02 (s, 1H), 7.33 (dd, J 3.9 Hz, 2.4 Hz, 1H), 6.66 (dd, J=3.9 Hz, 2.4 Hz, 1H), 5.69 (brs, 2H), 3.98-4.03 (m, 1H), 3.08 (dd, J=16.8 Hz, 8.4 Hz, 1H), 2.88 (dd, J=16.8 Hz, 3.6 Hz, 1H), 2.49-2.59 (m, 1H), 1.89-1.96 (m, 1H), 1.56-1.74 (m, 4H), 1.21-1.29 (m, 3H).

m/z=322[M+1]⁺.

Example 2: 3-[3-amino-4-(7H-pyrrolo[2,3-d]pyrimidin-4-yl)-1H-pyrazol-1-yl]-3-cyclopentyl propanamide

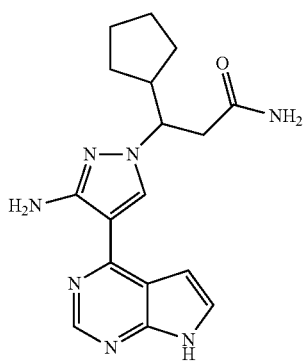 [SMILES: NC(=O)CC(C1CCCC1)n1cc(-c2ncnc3[nH]ccc23)c(N)n1]

The compound of Example 2 (0.45 g, 18% yield) was obtained from the separation by column chromatography on silica gel column in the step H of Example 1.

¹HNMR (400 MHz, DMSO-d6) δ 11.93 (s, 1H), 8.58 (s, 1H), 8.37 (s, 1H), 7.45-7.47 (m, 1H), 7.27 (s, 1H), 6.88-6.89 (m, 1H), 6.74 (s, 1H), 6.09 (s, 2H), 4.30-4.37 (m, 1H), 2.79 (dd, J=15.2 Hz, 9.6 Hz, 1H), 2.54 (dd, J=15.2 Hz, 4.0 Hz, 1H), 2.22-2.31 (m, 1H), 1.69-1.79 (m, 1H), 1.37-1.62 (m, 4H), 1.19-1.32 (m, 3H).

m/z=340[M+1]⁺.

Example 3: 3-[5-amino-4-(7H-pyrrolo[2,3-d]pyrimidin-4-yl)-1H-pyrazol-1-yl]-3-cyclopentylpropanenitrile

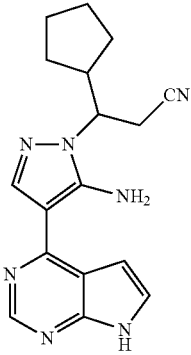 [SMILES: N#CCC(C1CCCC1)n1ncc(-c2ncnc3[nH]ccc23)c1N]

3-[5-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (130 mg, 0.289 mmol) was prepared by the step G of Example 1, and the compound of Example 3 (14 mg, 15.1% yield) was prepared according to the step H of Example 1.

¹HNMR (400 MHz, CDCl₃) δ 10.51-10.61 (brs, 1H), 8.70 (s, 1H), 8.16 (s, 1H), 7.33-7.35 (m, 1H), 6.80-6.81 (m, 1H), 6.01-6.35 (brs 2H), 4.11-4.17 (m, 1H), 3.17 (dd, 16.8 Hz, J=9.6 Hz, 1H), 2.92 (dd, J=16.8 Hz, J=4.0 Hz, 1H), 2.56-2.64 (m, 1H), 1.90-1.98 (m, 1H), 1.53-1.75 (m, 4H), 1.25-1.35 (m, 3H).

m/z=322[M+1]⁺.

Example 4: 3-[5-amino-4-(7H-pyrrolo[2,3-d]pyrimidin-4-yl)-1H-pyrazol-1-yl]-3-cyclopentyl propanamide

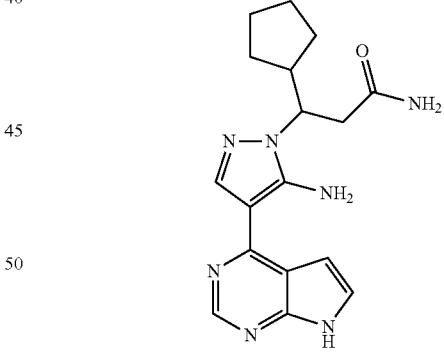

3-[5-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (130 mg, 0.289 mmol) was prepared by the step G of Example 1, and the compound of Example 4 (65 mg, 70% yield) was prepared according to the step H of Example 1.

¹HNMR (400 MHz, CDCl₃) δ11.94 (s, 1H), 8.60 (s, 1H), 8.16 (s, 1H), 7.46 (t, J=3.2 Hz, 1H), 7.39 (s, 1H), 6.92-6.94 (s, 1H), 6.90 (s, 2H), 6.87 (s, 1H), 4.43-4.48 (m, 1H), 2.86 (dd, J=15.2 Hz, 10.0 Hz, 1H), 2.65 (dd, J=15.2 Hz, 3.6 Hz, 1H), 2.35-2.44 (m, 1H), 1.80-1.89 (m, 1H), 1.45-1.73 (m, 4H), 1.23-1.39 (m, 3H).

m/z=340[M+1]⁺.

Example 5: (3R)-3-[3-amino-4-(7H-pyrrolo[2,3-d]pyrimidin-4-yl)-1H-pyrazol-1-yl]-3-cyclopentylpropanenitrile

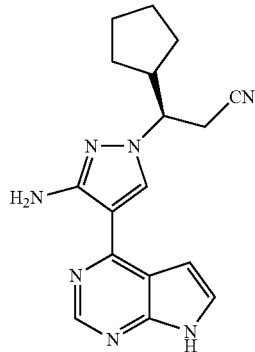

3-[3-amino-4-(7H-pyrrolo[2,3-d]pyrimidin-4-yl)-1H-pyrazol-1-yl]-3-cyclopentylpropanenitrile, obtained from the step H of Example 1, was separated by preparative HPLC (OJ-H column, 20% isopropanol/n-hexane, column temperature 25° C., flow rate 1.0 ml/min, retention time 20.30 min) to give (R)-configuration compound.

$^1$HNMR (400 MHz, CDCl$_3$) δ 9.37 (s, 1H), 8.79 (s, 1H), 8.02 (s, 1H), 7.32 (dd, J 3.9 Hz, 2.4 Hz, 1H), 6.68 (dd, J=3.9 Hz, 2.4 Hz, 1H), 5.69 (brs, 2H), 3.99-4.03 (m, 1H), 3.08 (dd, J=16.8 Hz, 8.8 Hz, 1H), 2.89 (dd, J=16.8 Hz, 3.6 Hz, 1H), 2.52-2.58 (m, 1H), 1.90-1.98 (m, 1H), 1.58-1.77 (m, 4H), 1.23-1.33 (m, 3H).

m/z=322[M+1]$^+$.

(3R)-3-[3-amino-4-(7H-pyrrolo[2,3-d]pyrimidin-4-yl)-1H-pyrazol-1-yl]-3-cyclopentylpropanenitrile hydrochloride

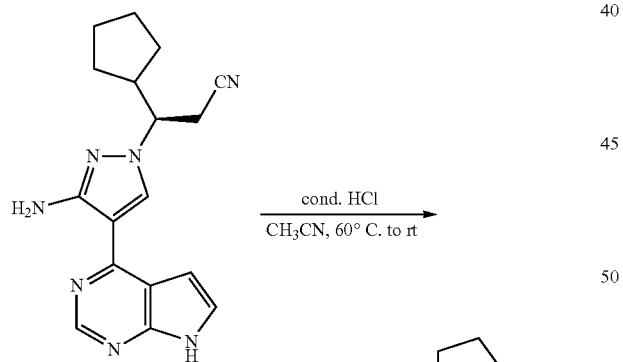

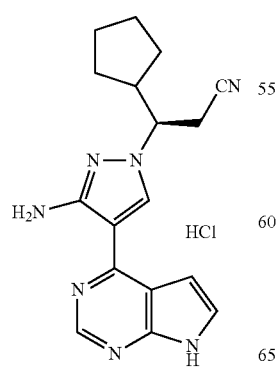

To a solution of (3R)-3-[3-amino-4-(7H-pyrrolo[2,3-d]pyrimidin-4-yl)-1H-pyrazol-1-yl]-3-cyclopentylpropanenitrile (2.0 g, 6.223 mmol, 1.0 eq.) in acetonitrile was added dropwise concentrated hydrochloric acid (12M, 0.52 mL, 6.223 mmol, 1.0 eq.) at room temperature. The reaction liquid was stirred for 1 hr at 60° C., until the solution became clear. The solution was stirred and cooled at room temperature to precipitate solids. The resulting mixture was concentrated under reduced pressure, dichloromethane was added, and the resulting mixture was concentrated two times to give crude product (2.3 g) as a dark yellow solid. To the crude product was added ethyl acetate (12 mL). The mixture was heated to 60° C. and stirred for 1 hr, then cooled to room temperature with stirring. The light yellow flocculent solids were filtered, washed with ethyl acetate, and pumped to dryness to give a light yellow solid (2.2 g, yield 99.6%, purity 99.82%, ee value more than 99.0%).

Example 6: (3S)-3-[3-amino-4-(7H-pyrrolo[2,3-d]pyrimidin-4-yl)-1H-pyrazol-1-yl]-3-cyclopentylpropanenitrile

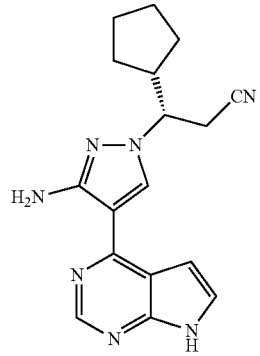 [SMILES: N#CC[C@@H](C1CCCC1)n1cc(-c2ncnc3[nH]ccc23)c(N)n1]

3-[3-amino-4-(7H-pyrrolo[2,3-d]pyrimidin-4-yl)-1H-pyrazol-1-yl]-3-cyclopentylpropanenitrile, obtained from the step H of Example 1, was separated by preparative HPLC (OJ-H column, 20% isopropanol/n-hexane, column temperature 25° C., flow rate 1.0 ml/min, retention time 17.20 min) to give (S)-configuration compound.

$^1$HNMR (400 MHz, CDCl$_3$) δ 9.23 (s, 1H), 8.78 (s, 1H), 8.02 (s, 1H), 7.32 (dd, J=3.9 Hz, 2.4 Hz, 1H), 6.68 (dd, J=3.9 Hz, 2.4 Hz, 1H), 5.69 (brs, 2H), 3.98-4.03 (m, 1H), 3.08 (dd, J=16.8 Hz, 8.8 Hz, 1H), 2.89 (dd, J=17.2 Hz, 3.6 Hz, 1H), 2.52-2.58 (m, 1H), 1.90-1.95 (m, 1H), 1.58-1.74 (m, 4H), 1.22-1.33 (m, 3H).

m/z=322[M+1]$^+$.

Example 7: 3-[3-ethylamino-4-(7H-pyrrolo[2,3-d]pyrimidin-4-yl)-1H-pyrazol-1-yl]-3-cyclopentylpropanenitrile

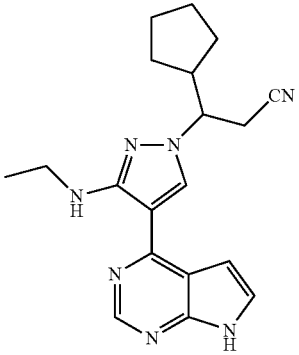 [SMILES: CCNc1nn(C(CC#N)C2CCCC2)cc1-c1ncnc2[nH]ccc12]

Step A: 3-[3-ethylamino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile

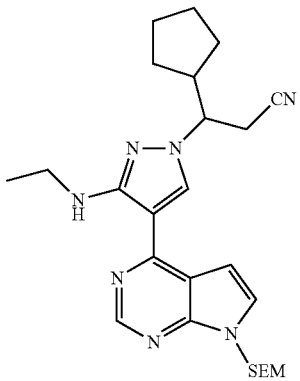 [SMILES: CCNc1nn(C(CC#N)C2CCCC2)cc1-c1ncnc2c1ccn2COCC[Si](C)(C)C]

To a solution of 3-[3-amino-4-(7-{[2-(trimethylsilyl)ethoxy]methyl)}-7H-pyrrolo[2,3-d]pyrimidin-4-yl)-1H-pyrazol-1-yl]-3-cyclopentylpropanenitrile (500 mg, 1.11 mmol, 1.0 eq., prepared by the step G of Example 1) and potassium carbonate (460 mg, 3.33 mmol, 3.0 eq.) in DMF was added iodoethane (347 mg, 2.22 mmol, 2.0 eq.) at room temperature. The reaction liquid was protected with nitrogen gas and stirred overnight at 70° C. The resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give 3-[3-ethylamino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (116 mg, 22.6% yield).

$^1$HNMR (400 MHz, CDCl$_3$): δ 8.77 (s, 1H), 8.01 (s, 1H), 7.32 (d, J=3.6, 1H), 7.01-7.17 (brs, 1H), 6.67 (d, J=4.0, 1H), 5.65 (s, 2H), 4.07-4.01 (m, 1H), 3.55-3.51 (m, 2H), 3.46-3.41 (m, 2H), 3.10 (dd, J=16.8 Hz, J=8, 1H), 2.91 (dd, J=17.2 Hz, J=4, 1H), 2.62-2.60 (m, 1H), 1.96-1.93 (m, 1H), 1.74-1.55 (m, 7H), 1.35-1.22 (m, 3H), 0.91 (t, J=8.0, 2H), 0.00 (s, 9H).

m/z=480[M+1]$^+$.

Step B: 3-[3-ethylamino-4-(7H-pyrrolo[2,3-d]pyrimidin-4-yl)-1H-pyrazol-1-yl]-3-cyclopentylpropanenitrile

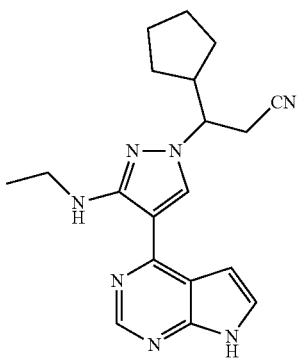 [SMILES: CCNc1nn(C(CC#N)C2CCCC2)cc1-c1ncnc2[nH]ccc12]

The compound of Example 7 was prepared according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with 3-[3-ethylamino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile.

$^1$HNMR (400 MHz, CDCl$_3$) δ 9.47 (s, 1H), 8.76 (s, 1H), 8.03 (s, 1H), 7.29-7.30 (m, 1H), 7.01-7.17 (brs, 1H), 6.66-6.68 (m, 1H), 4.03-4.08 (m, 1H), 3.44 (q, J=7.2 Hz, 2H), 3.11 (dd, J=16.8 Hz, 7.6 Hz, 1H), 2.92 (dd, J=16.8 Hz, 3.6 Hz, 1H), 2.58-2.64 (m, 1H), 1.91-1.99 (m, 1H), 1.59-1.78 (m, 4H), 1.34 (t, J=7.2 Hz, 3H), 1.27-1.32 (m, 3H).

m/z=350[M+1]$^+$.

Example 7A: (R)-3-[3-ethylamino-4-(7H-pyrrolo[2,3-d]pyrimidin-4-yl)-1H-pyrazol-1-yl]-3-cyclopentyl-propanenitrile

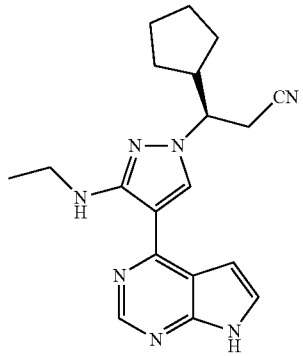 [SMILES: CCNc1nn([C@H](CC#N)C2CCCC2)cc1-c1ncnc2[nH]ccc12]

3-[3-ethylamino-4-(7H-pyrrolo[2,3-d]pyrimidin-4-yl)-1H-pyrazol-1-yl]-3-cyclopentylpropanenitrile, obtained from Example 7, was separated by preparative HPLC (OD-H column, 5% absolute ethanol/n-hexane, column temperature 30° C., flow rate 1.0 mL/min, retention time 35.32 min) to give (R)-configuration compound.

$^1$HNMR (400 MHz, CDCl$_3$) δ 9.47 (s, 1H), 8.77 (s, 1H), 8.04 (s, 1H), 7.29-7.30 (m, 1H), 7.03-7.17 (brs, 1H), 6.65-6.67 (m, 1H), 4.04-4.08 (m, 1H), 3.44 (q, J=7.2 Hz, 2H), 3.11 (dd, J=16.8 Hz, 7.6 Hz, 1H), 2.92 (dd, J=16.8 Hz, 3.6 Hz, 1H), 2.58-2.64 (m, 1H), 1.91-1.98 (m, 1H), 1.59-1.78 (m, 4H), 1.34 (t, J=7.2 Hz, 3H), 1.27-1.32 (m, 3H).

m/z=350[M+1]$^+$.

Example 7B: (S)-3-[3-ethylamino-4-(7H-pyrrolo[2,3-d]pyrimidin-4-yl)-1H-pyrazol-1-yl]-3-cyclopentyl-propanenitrile

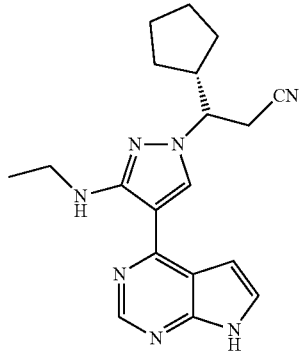

3-[3-ethylamino-4-(7H-pyrrolo[2,3-d]pyrimidin-4-yl)-1H-pyrazol-1-yl]-3-cyclopentylpropanenitrile, obtained from Example 7, was separated by preparative HPLC (OD-H column, 5% absolute ethanol/n-hexane, column temperature 30° C., flow rate 1.0 mL/min, retention time 32.13 min) to give (S)-configuration compound.

$^1$HNMR (400 MHz, CDCl$_3$) δ 9.46 (s, 1H), 8.77 (s, 1H), 8.04 (s, 1H), 7.29-7.30 (m, 1H), 7.02-7.17 (brs, 1H), 6.65-6.67 (m, 1H), 4.03-4.08 (m, 1H), 3.44 (q, J=7.2 Hz, 2H), 3.11 (dd, J=16.8 Hz, 7.6 Hz, 1H), 2.92 (dd, J=16.8 Hz, 3.6 Hz, 1H), 2.58-2.63 (m, 1H), 1.91-1.99 (m, 1H), 1.59-1.77 (m, 4H), 1.34 (t, J=7.2 Hz, 3H), 1.27-1.32 (m, 3H).

m/z=350[M+1]$^+$.

Example 8: 3-cyclopentyl-3-[3-(diethylamino)-4-(7H-pyrrolo[2,3-d]pyrimidin-4-yl)-1H-pyrazol-1-yl]propionitrile

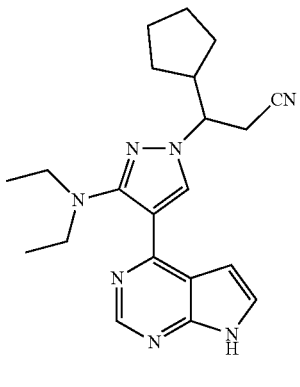 [SMILES: CCN(CC)c1nn(C(CC#N)C2CCCC2)cc1-c1ncnc2[nH]ccc12]

Step A: 3-cyclopentyl-3-[3-(diethylamino)-4-(7-{[2-(trimethylsilyl)ethoxy]methyl}-7H-pyrrolo[2,3-d]pyrimidin-4-yl)-1H-pyrazol-1-yl]propionitrile

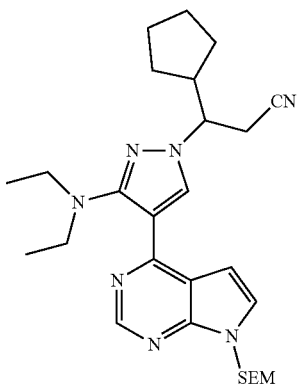 [SMILES: CCN(CC)c1nn(C(CC#N)C2CCCC2)cc1-c1ncnc2c1ccn2COCC[Si](C)(C)C]

To a solution of 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (500 mg, 1.11 mmol, 1.0 eq., prepared from the step G of Example 1) and potassium carbonate (460 mg, 3.33 mmol, 3.0 eq.) in DMF was added iodoethane (347 mg, 2.22 mmol, 2.0 eq.) at room temperature. The reaction liquid was protected with nitrogen gas and stirred overnight at 70° C. The resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give 3-[3-ethylamino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (2 mg, 0.4% yield).

$^1$HNMR (400 MHz, CDCl$_3$) δ 8.90 (s, 1H), 8.01 (s, 1H), 7.32 (s, 1H), 7.14 (s, 1H), 5.72 (s, 2H), 4.13-4.09 (m, 1H), 3.62 (t, J=8.0, 2H), 3.25-3.18 (m, 4H), 3.14 (dd, J=16.8 Hz, J=8.0 Hz, 1H), 2.91 (dd, J=16.8 Hz, J=4.0 Hz, 1H), 2.70-2.53 (m, 1H), 2.05-1.95 (m, 1H), 1.82-1.51 (m, 4H), 1.43-1.31 (m, 3H), 1.17-1.11 (m, 6H), 1.04-0.90 (m, 2H), 0.00 (s, 9H).

m/z=508[M+1]$^+$.

Step B: 3-cyclopentyl-3-[3-(diethylamino)-4-(7H-pyrrolo[2,3-d]pyrimidin-4-yl)-1H-pyrazol-1-yl]propionitrile

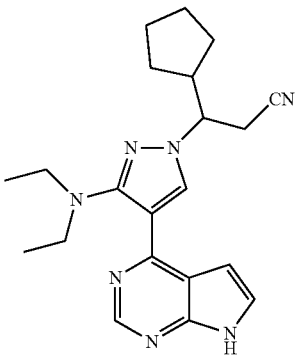 [SMILES: CCN(CC)c1nn(C(CC#N)C2CCCC2)cc1-c1ncnc2[nH]ccc12]

The compound of Example 8 was prepared according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with 3-[3-(diethylamino)-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile.

m/z=378[M+1]$^+$.

Example 9: N-[1-(2-cyano-1-cyclopentylethyl)-4-(7H-pyrrolo[2,3-d]pyrimidin-4-yl)-1H-pyrazol-3-yl]acetamide

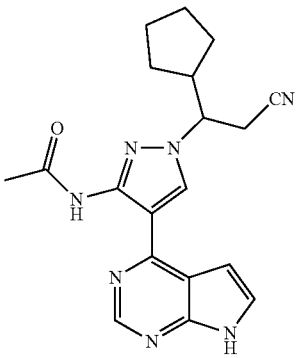

Step A: N-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-yl]acetamide

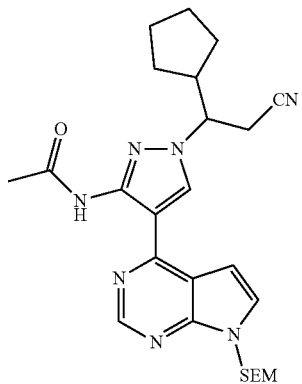 [SMILES: CC(=O)Nc1nn(C(CC#N)C2CCCC2)cc1-c1ncnc2c1ccn2COCC[Si](C)(C)C]

To a solution of 3-[3-amino-4-(7-{[2-(trimethylsilyl)ethoxy]methyl)}-7H-pyrrolo[2,3-d]pyrimidin-4-yl)-1H-pyrazol-1-yl]-3-cyclopentylpropanenitrile (100 mg, 0.221 mmol, 1.0 eq., prepared from the step G of Example 1) in dichloromethane was added dropwise acetyl chloride (17.4 mg, 0.211 mmol, 1.0 eq.) at 0° C. The reaction liquid was stirred for 2 hrs at room temperature. After the reaction was completed, the resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give N-(1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-yl]acetamide (90 mg, 83% yield).

Step B: N-(1-(2-cyano-1-cyclopentylethyl)-4-(7H-pyrrolo[2,3-d]pyrimidin-4-yl)-1H-pyrazol-3-yl)acetamide

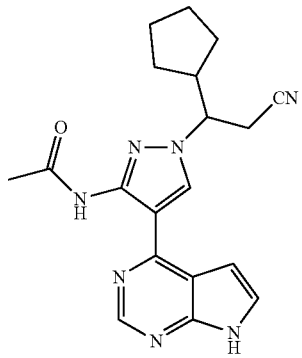 [SMILES: CC(=O)Nc1nn(C(CC#N)C2CCCC2)cc1-c1ncnc2[nH]ccc12]

The compound of Example 9 was prepared according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with N-[1-(2-cyano-1-cyclopentylethyl)-4-(7-{[2-(trimethylsilyl)ethoxy]methyl)}-7H-pyrrolo[2,3-d]pyrimidin-4-yl)-1H-pyrazol-3-yl]acetamide.

¹HNMR (400 MHz, CDCl₃) δ 11.51-11.61 (brs, 1H), 10.21-10.41 (brs, 1H), 8.83 (s, 1H), 8.20 (s, 1H), 7.41 (dd, J=3.2 Hz, J=2.4 Hz, 1H), 6.70 (s, 1H), 4.27-4.39 (m, 1H), 3.11 (dd, J=16.8 Hz, J=7.6 Hz, 1H), 2.97-3.01 (m, 1H), 2.43-2.71 (m, 4H), 1.94-2.01 (m, 1H), 1.56-1.79 (m, 4H), 1.25-1.31 (m, 3H).
m/z=364[M+1]⁺.

Example 9A: N-[1-((R)-2-cyano-1-cyclopentyl-ethyl)-4-(7H-pyrrolo[2,3-d]pyrimidin-4-yl)-1H-pyrazol-3-yl]acetamide

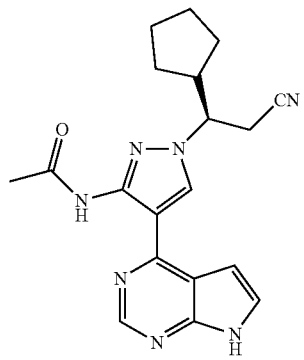 [SMILES: CC(=O)Nc1nn([C@H](CC#N)C2CCCC2)cc1-c1ncnc2[nH]ccc12]

N-(1-(2-cyano-1-cyclopentylethyl)-4-(7H-pyrrolo[2,3-d]pyrimidin-4-yl)-1H-pyrazol-3-yl)acetamide, obtained from Example 9, was separated by preparative HPLC (OJ-H column, 7% absolute ethanol/n-hexane, column temperature 35° C., flow rate 1.0 mL/min, retention time 60.6 min) to give (R)-configuration compound.

¹HNMR (400 MHz, CDCl₃) δ 11.52-11.61 (brs, 1H), 10.22-10.41 (brs, 1H), 8.83 (s, 1H), 8.20 (s, 1H), 7.41 (dd, J=3.2 Hz, J=2.4 Hz, 1H), 6.70 (s, 1H), 4.27-4.39 (m, 1H), 3.11 (dd, J=16.8 Hz, J=7.6 Hz, 1H), 2.97-3.02 (m, 1H), 2.41-2.71 (m, 4H), 1.93-2.01 (m, 1H), 1.56-1.78 (m, 4H), 1.24-1.31 (m, 3H).
m/z=364[M+1]⁺.

Example 9B: N-[1-((S)-2-cyano-1-cyclopentyl-ethyl)-4-(7H-pyrrolo[2,3-d]pyrimidin-4-yl)-1H-pyrazol-3-yl]acetamide

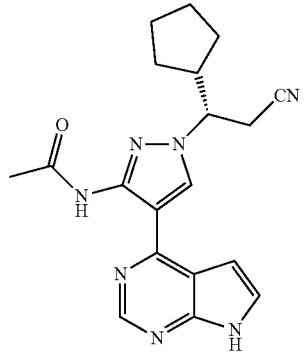 [SMILES: CC(=O)Nc1nn([C@@H](CC#N)C2CCCC2)cc1-c1ncnc2[nH]ccc12]

N-(1-(2-cyano-1-cyclopentylethyl)-4-(7H-pyrrolo[2,3-d]pyrimidin-4-yl)-TH-pyrazol-3-yl)acetamide, obtained from Example 9, was separated by preparative HPLC (OJ-H column, 7% absolute ethanol/n-hexane, column temperature 35° C., flow rate 1.0 mL/min, retention time 55.5 min) to give (S)-configuration compound.

¹HNMR (400 MHz, CDCl₃) δ 11.52-11.62 (brs, 1H), 10.22-10.41 (brs, 1H), 8.83 (s, 1H), 8.20 (s, 1H), 7.41 (dd, J=3.2 Hz, J=2.4 Hz, 1H), 6.70 (s, 1H), 4.27-4.40 (m, 1H), 3.11 (dd, J=16.8 Hz, J=7.6 Hz, 1H), 2.98-3.04 (m, 1H), 2.41-2.72 (m, 4H), 1.94-2.01 (m, 1H), 1.55-1.79 (m, 4H), 1.24-1.33 (m, 3H).

m/z=364[M+1]⁺.

Example 10: N-[1-(2-cyano-1-cyclopentylethyl)-4-(7H-pyrrolo[2,3-d]pyrimidin-4-yl)-1H-pyrazol-3-yl]methylsulfamide

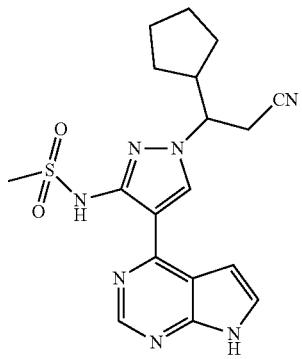 [SMILES: CS(=O)(=O)Nc1nn(C(CC#N)C2CCCC2)cc1-c1ncnc2[nH]ccc12]

Step A: N-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-yl]methylsulfamide

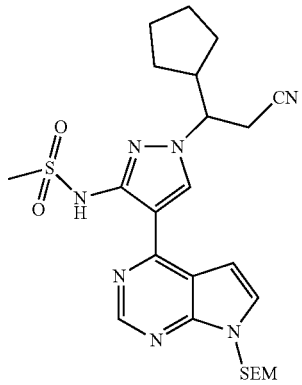 [SMILES: C[Si](C)(C)CCOCn1ccc2c(-c3cn(C(CC#N)C4CCCC4)nc3NS(C)(=O)=O)ncnc21]

To a solution of 3-[3-amino-4-(7-{[2-(trimethylsilyl)ethoxy]methyl})-7H-pyrrolo[2,3-d]pyrimidin-4-yl)-1H-pyrazol-1-yl]-3-cyclopentylpropanenitrile (100 mg, 0.221 mmol, 1.0 eq., prepared from the step G of Example 1) in dichloromethane was added dropwise pyridine (30.0 mg, 0.379 mmol, 1.7 eq.) at 0° C., and methylsufonyl chloride (25.0 mg, 0.211 mmol, 1.0 eq.) was added dropwise subsequently. The reaction liquid was stirred for 72 hrs at room temperature. After the reaction was completed, the resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give N-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-yl]methylsulfamide (85 mg, 73% yield).

¹HNMR (400 MHz, CDCl₃) δ 11.20-10.70 (brs, 1H), 8.78 (s, 1H), 8.15 (s, 1H), 7.40 (s, 1H), 6.67 (s, 1H), 5.65 (s, 2H), 4.21-4.18 (m, 1H), 3.53 (t, J=8.0, 2H), 3.31 (s, 3H), 3.16-3.10 (m, 1H), 2.94 (d, J=8.0 Hz, 1H), 2.62-2.60 (m, 1H), 2.03-1.92 (m, 1H), 1.75-1.58 (m, 4H), 1.32-1.23 (m, 3H), 0.93-0.85 (m, 2H), 0.00 (s, 9H).

m/z=530[M+1]⁺.

Step B: N-(1-(2-cyano-1-cyclopentylethyl)-4-(7H-pyrrolo[2,3-d]pyrimidin-4-yl)-1H-pyrazol-3-yl)methylsulfamide

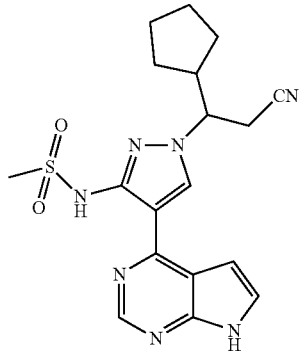 [SMILES: CS(=O)(=O)Nc1nn(C(CC#N)C2CCCC2)cc1-c1ncnc2[nH]ccc12]

The compound of Example 10 was prepared according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with N-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-yl]methylsulfamide.

¹HNMR (400 MHz, CDCl₃) δ 12.25 (s, 1H), 10.80 (s, 1H), 8.91 (s, 1H), 8.72 (s, 1H), 7.65 (dd, J=3.2 Hz, J=2.4 Hz, 1H), 7.01 (dd, J=3.6 Hz, J=1.6 Hz, 1H), 4.40-4.46 (m, 1H), 3.32 (s, 3H), 3.24 (dd, J=17.6 Hz, J=9.2 Hz, 1H), 3.18 (dd, J=17.6 Hz, J=4.4 Hz, 1H), 2.40-2.46 (m, 1H), 1.77-1.86 (m, 1H), 1.35-1.63 (m, 7H).

m/z=400[M+1]⁺.

Example 11: 3-cyclopentyl-3-[3-(2-morpholinylethylamino)-4-(7H-pyrrolo[2,3-d]pyrimidin-4-yl)-1H-pyrazol-1-yl]propionitrile

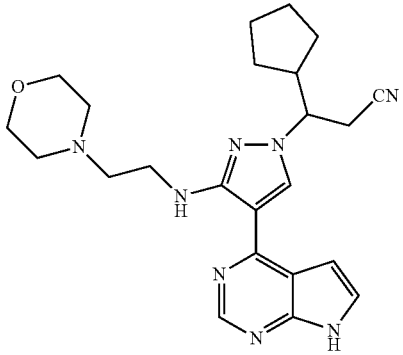 [SMILES: N#CCC(C1CCCC1)n1cc(-c2ncnc3[nH]ccc23)c(NCCN2CCOCC2)n1]

Step A: 3-cyclopentyl-3-(3-(2-morpholinylethyl-amino)-4-7-{[2-(trimethylsilyl) ethoxy]methyl}-7H-pyrrolo[2,3-d]pyrimidin-4-yl)-1H-pyrazol-1-yl]propionitrile

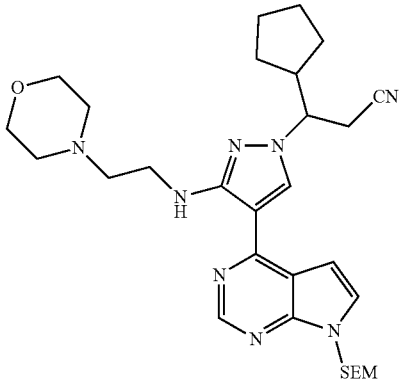 [SMILES: C[Si](C)(C)CCOCn1ccc2c(-c3cn(C(CC#N)C4CCCC4)nc3NCCN3CCOCC3)ncnc21]

To a solution of 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (100 mg, 0.211 mmol, 1.0 eq., prepared from the step G of Example 1) in acetonitrile were added 4-(2-chloroethyl)morpholine (46 mg, 0.243 mmol, 1.1 eq.), potassium carbonate (91 mg, 0.663 mmol, 3.0 eq.) and potassium iodide (4 mg, 0.023 mmol, 0.1 eq.) at room temperature. The reaction liquid was subjected to microwave for 3 hrs at 90° C. The resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give 3-cyclopentyl-3-[3-(2-morpholinylethylamino)-4-7-{[2-(trimethylsilyl)ethoxy]methyl}-7H-pyrrolo[2,3-d]pyrimidin-4-yl)-1H-pyrazol-1-yl]propionitrile (12 mg, 9.7% yield).

$^1$HNMR (400 MHz, CDCl$_3$): δ 8.84 (s, 1H), 8.06 (s, 1H), 7.68-7.43 (brs, 1H), 7.36 (d, J 3.2 Hz, 1H), 6.73 (d, J=3.6 Hz, 1H), 5.71 (s, 2H), 4.12-4.06 (m, 1H), 3.96-3.83 (m, 4H), 3.76-3.65 (m, 2H), 3.63 (t, J=12.4 Hz, 2H), 3.20-3.14 (m, 1H), 2.98-2.92 (m, 3H), 2.89-2.70 (m, 4H), 2.68-2.62 (m, 1H), 2.01-1.98 (m, 1H), 1.80-1.63 (m, 4H), 1.38-1.30 (m, 3H), 0.99-0.91 (m, 2H), 0.00 (s, 9H).
m/z=565 [M+1]$^+$.

Step B: 3-cyclopentyl-3-[3-(2-morpholinylethyl-amino)-4-(7H-pyrrolo[2,3-d]pyrimidin-4-yl)-1H-pyrazol-1-yl]propionitrile

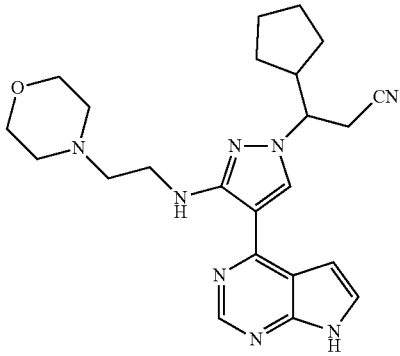 [SMILES: N#CCC(C1CCCC1)n1cc(-c2ncnc3[nH]ccc23)c(NCCN2CCOCC2)n1]

The compound of Example 11 was prepared according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with 3-cyclopentyl-3-[3-(2-morpholinylethyl-amino)-4-7-{[2-(trimethylsilyl)ethoxy]methyl}-7H-pyrrolo[2,3-d]pyrimidin-4-yl)-1H-pyrazol-1-yl]propionitrile.

$^1$HNMR (400 MHz, CDCl$_3$) δ 10.98 (s, 1H), 8.78 (s, 1H), 8.03 (s, 1H), 7.46-7.58 (brs, 1H), 7.34 (d, J=2.0 Hz, 1H), 6.64 (d, J=3.2 Hz, 1H), 4.03-4.08 (m, 1H), 3.77-3.90 (m, 4H), 3.56-3.70 (m, 2H), 3.13 (dd, J=16.8 Hz, J=8.4 Hz, 1H), 2.92 (dd, J=16.8 Hz, J=3.6 Hz, 1H), 2.54-2.79 (m, 7H), 1.92-1.99 (m, 1H), 1.59-1.78 (m, 4H), 1.28-1.32 (m, 3H). m/z=435[M+1]$^+$.

Example 12: N-[1-(2-cyano-1-cyclopentylethyl)-4-(7H-pyrrolo[2,3-d]pyrimidin-4-yl)-1H-pyrazol-3-yl]-2-morpholinylacetamide

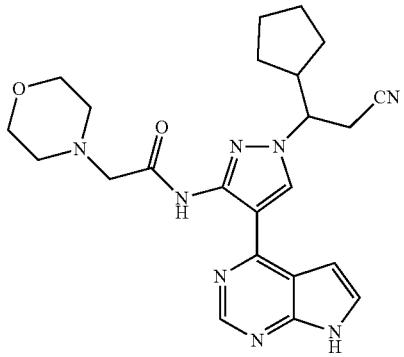 [SMILES: N#CCC(C1CCCC1)n1cc(-c2ncnc3[nH]ccc23)c(NC(=O)CN2CCOCC2)n1]

Step A: 2-chloro-N-[1-(2-cyano-1-cyclopentyl-ethyl)-4-(7-{[2-(trimethylsilyl)ethoxy]methyl}-7H-pyrrolo[2,3-d]pyrimidin-4-yl)-1H-pyrazol-3-yl]acet-amide

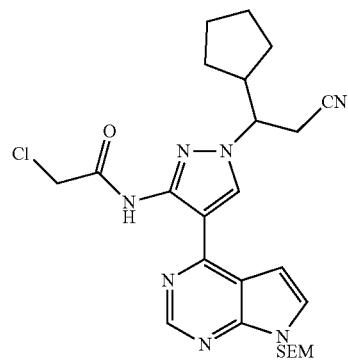 [SMILES: C[Si](C)(C)CCOCn1ccc2c(-c3cn(C(CC#N)C4CCCC4)nc3NC(=O)CCl)ncnc21]

To a solution of 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (60 mg, 0.13 mmol, 1.0 eq., prepared from the step G of Example 1) and triethylamine (20 mg, 0.20 mmol, 1.5 eq.) in dry THF was added 2-chloroacetyl chloride (17 mg, 0.15 mmol, 1.1 eq.) under stirring in an ice bath. The reaction liquid was stirred for 15 min at room temperature. The resulting mixture was diluted with water and ethyl acetate, and extracted with ethyl acetate. The combined organic phase was washed with brine, dried over sodium sulfate, filtered and concentrated in vacuo. The residue was directly used in the next step of the reaction.

¹H NMR (CDCl₃) δ 12.78 (1H, s), 8.86 (1H, s), 8.25 (1H, s), 7.45 (1H, d, J=3.6 Hz), 6.76 (1H, d, J=3.6 Hz), 5.71 (2H, s), 4.30-4.39 (3H, m), 3.57 (2H, t, J=8.4 Hz), 3.14 (1H, dd, J=17.2 Hz, 7.2 Hz), 3.03 (1H, dd, J=17.2 Hz, 3.6 Hz), 2.70-2.80 (1H, m), 1.99-2.06 (1H, m), 1.55-1.80 (4H, m), 1.34-1.38 (3H, m), 0.95 (2H, t, J=8.4 Hz), −0.02 (9H, s).

m/z=528[M+1]⁺.

Step B: N-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-yl]-2-morpholinylacetamide

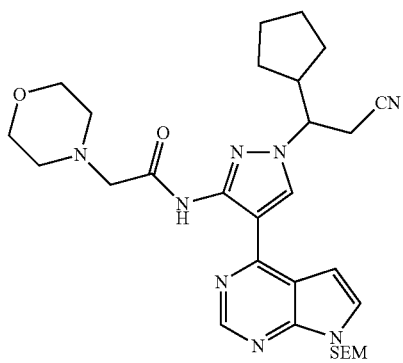 [SMILES: C[Si](C)(C)CCOCn1ccc2c(-c3cn(C(CC#N)C4CCCC4)nc3NC(=O)CN3CCOCC3)ncnc21]

The crude product obtained in the above step was dissolved in DMF solution (5 mL), and morpholine (13 mg, 0.15 mmol, 1.1 eq.), potassium carbonate (37 mg, 0.27 mmol, 2.2 eq.) and sodium iodide (20 mg, 0.13 mmol, 1.0 eq.) were added thereto. The mixture was stirred overnight at 100° C. The mixture was cooled to room temperature, diluted with water and ethyl acetate, and extracted with ethyl acetate. The combined organic phase was washed with brine, dried over sodium sulfate, filtered and concentrated in vacuo. The resulting residue was separated by column chromatography on silica gel column to give the titled compound (97 mg), as a yellow solid.

¹H NMR (CDCl₃) δ 12.27 (1H, s), 8.97 (1H, s), 8.21 (1H, s), 7.41 (1H, d, J=3.6 Hz), 6.73 (1H, d, J=3.6 Hz), 5.68 (2H, s), 4.30-4.35 (1H, m), 3.84-3.89 (4H, m), 3.57 (2H, t, J=8.4 Hz), 3.26 (2H, s), 3.10 (1H, dd, J=17.3 Hz, 6.9 Hz), 3.02 (1H, dd, J=17.2 Hz, 3.6 Hz), 2.72-2.77 (1H, m), 2.66-2.70 (4H, m), 1.97-2.04 (1H, m), 1.58-1.80 (4H, m), 1.30-1.34 (3H, m), 0.93 (2H, t, J=8.4 Hz), −0.05 (9H, s).

m/z=579[M+1]⁺.

Step C: N-[1-(2-cyano-1-cyclopentylethyl)-4-(7H-pyrrolo[2,3-d]pyrimidin-4-yl)-1H-pyrazol-3-yl]-2-morpholinylacetamide

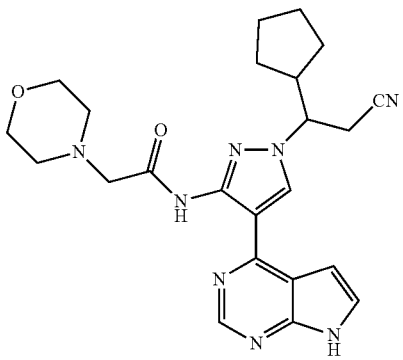 [SMILES: N#CCC(C1CCCC1)n1cc(-c2ncnc3[nH]ccc23)c(NC(=O)CN2CCOCC2)n1]

The compound obtained in the above step was reacted according to the step H of Example 1 to obtain the titled compound (40 mg, 67% yield), as a white solid.

¹H NMR (CDCl₃) δ 12.27 (1H, s), 9.71 (1H, s), 8.97 (1H, s), 8.24 (1H, s), 7.41 (1H, d, J=3.2 Hz), 6.74 (1H, d, J=3.2 Hz), 4.33-4.38 (1H, m), 3.87-3.90 (4H, m), 3.28 (2H, s), 3.11 (1H, dd, J=17.2 Hz, 6.8 Hz), 3.02 (1H, dd, J=17.2 Hz, 4.0 Hz), 2.69-2.72 (5H, m), 1.95-2.06 (1H, m), 1.55-1.81 (4H, m), 1.28-1.34 (3H, m).

m/z=449[M+1]⁺.

Example 13: 3-cyclopentyl-3-[3-(3-morpholinyl-3-oxopropylamino)-4-(7H-pyrrolo[2,3-d]pyrimidin-4-yl)-1H-pyrazol-1-yl]propionitrile

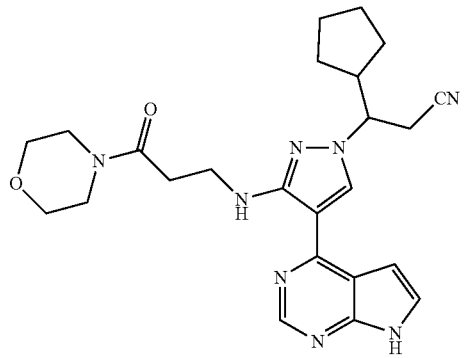 [SMILES: N#CCC(C1CCCC1)n1cc(-c2ncnc3[nH]ccc23)c(NCCC(=O)N2CCOCC2)n1]

Step A: 3-cyclopentyl-3-[3-(3-morpholinyl-3-oxopropylamino)-4-7-{[2-(trimethylsilyl)ethoxy]methyl}-7H-pyrrolo[2,3-d]pyrimidin-4-yl)-1H-pyrazol-1-yl]propionitrile

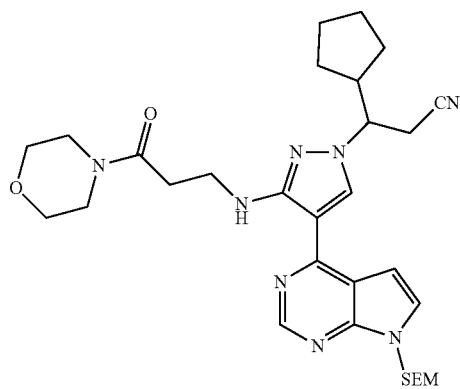 [SMILES: C[Si](C)(C)CCOCn1ccc2c(-c3cn(C(CC#N)C4CCCC4)nc3NCCC(=O)N3CCOCC3)ncnc21]

The compound was prepared according to the step A of Example 11, except that 4-(2-chloroethyl)morpholine was replaced with a side chain 3-bromo-N-propionylmorpholine.

¹HNMR (400 MHz, CDCl₃) δ 8.76 (s, 1H), 8.00 (s, 1H), 7.65-7.58 (brs, 1H), 7.36 (d, J 3.6 Hz, 1H), 6.60 (d, J=4.0 Hz, 1H), 5.65 (s, 2H), 4.02-4.01 (m, 1H), 3.82-3.73 (m, 2H), 3.64-3.59 (m, 4H), 3.55-3.15 (m, 6H), 3.12-3.08 (dd, J=16.8 Hz, J=8.8 Hz, 1H), 2.89-2.72 (m, 3H), 2.62-2.52 (m, 1H), 1.94-1.92 (m, 1H), 1.74-1.57 (m, 4H), 1.33-1.24 (m, 3H), 0.93-0.88 (m, 2H), 0.00 (s, 9H).

m/z=593[M+1]⁺.

Step B: 3-cyclopentyl-3-[3-(3-morpholinyl-3-oxo-propylamino)-4-(7H-pyrrolo[2,3-d]pyrimidin-4-yl)-1H-pyrazol-1-yl]propionitrile

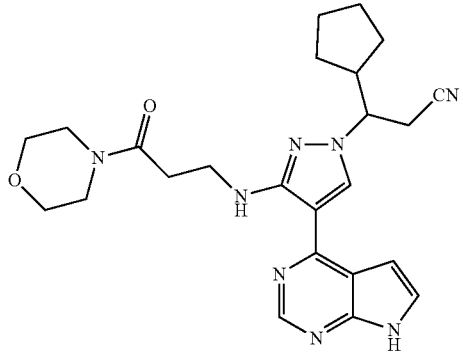 [SMILES: N#CCC(C1CCCC1)n1cc(-c2ncnc3[nH]ccc23)c(NCCC(=O)N2CCOCC2)n1]

The compound of Example 13 was prepared according to the step H of Example 1, except that 3-[3-amino-4-(7-{[2-(trimethylsilyl)ethoxy]methyl}-7H-pyrrolo[2,3-d]pyrimidin-4-yl]-1H-pyrazol-1-yl]-3-cyclopentylpropanenitrile was replaced with 3-cyclopentyl-3-[3-(3-morpholinyl-3-oxopropylamino)-4-7-{[2-(trimethylsilyl)ethoxy]methyl}-7H-pyrrolo[2,3-d]pyrimidin-4-yl)-1H-pyrazol-1-yl]propionitrile.

¹HNMR (400 MHz, CDCl₃) δ 10.59 (s, 1H), 8.74 (s, 1H), 8.14 (s, 1H), 7.31 (d, J=2.8 Hz, 1H), 6.62 (d, J=2.8 Hz, 1H), 4.01-4.06 (m, 1H), 3.75-3.80 (m, 2H), 3.46-3.66 (m, 8H), 3.12 (dd, J=16.8 Hz, J=8.8 Hz, 1H), 2.82-2.91 (m, 2H), 2.71-2.78 (m, 1H), 2.51-2.57 (m, 1H), 1.88-1.96 (m, 1H), 1.54-1.75 (m, 4H), 1.27-1.32 (m, 3H).

m/z=463 [M+1]⁺.

Example 14: 3-cyclopentyl-3-[3-(2-morpholinyl-2-oxoethylamino)-4-(7H-pyrrolo[2,3-d]pyrimidin-4-yl)-1H-pyrazol-1-yl]propionitrile

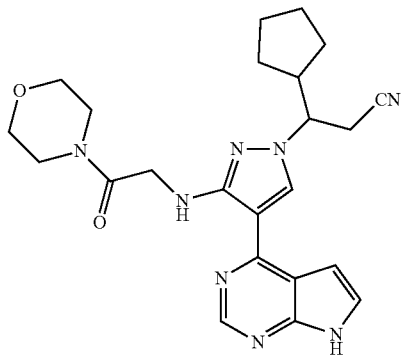 [SMILES: N#CCC(C1CCCC1)n1cc(-c2ncnc3[nH]ccc23)c(NCC(=O)N2CCOCC2)n1]

Step A: ethyl-2-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]acetate

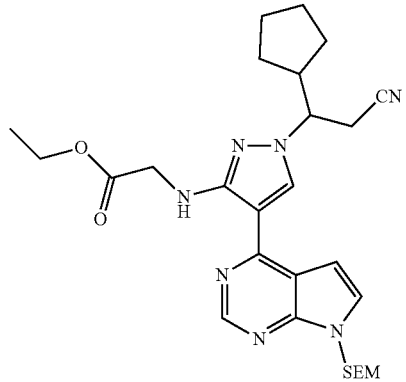 [SMILES: CCOC(=O)CNc1nn(C(CC#N)C2CCCC2)cc1-c1ncnc2c1ccn2COCC[Si](C)(C)C]

The compound was prepared according to the step A of Example 11, except that 4-(2-chloroethyl)morpholine was replaced with a side chain ethyl bromoacetate.

¹HNMR (400 MHz, CDCl₃) δ 8.81 (s, 1H), 8.01 (s, 1H), 7.33 (d, J=3.6 Hz, 1H), 6.67 (d, J=3.6 Hz, 1H), 5.66 (s, 2H), 4.27-4.19 (m, 4H), 4.03-4.01 (m, 1H), 3.53 (t, J=8.4 Hz, 2H), 3.10 (dd, J=16.8 Hz, J=8.4 Hz, 1H), 2.90 (dd, J=16.8 Hz, J=4.0 Hz, 1H), 2.60-2.60 (m, 1H), 1.97-1.90 (m, 1H), 1.72-1.57 (m, 5H), 1.31-1.24 (m, 5H), 0.93-0.89 (t, J=8.4 Hz, 2H), 0.00 (s, 9H).

m/z=538[M+1]⁺.

Step B: 2-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]acetic acid

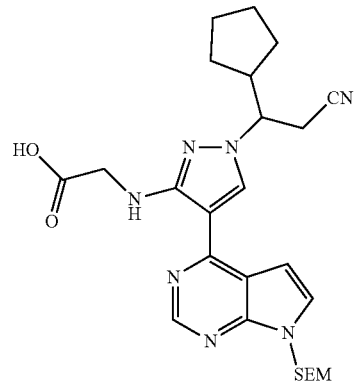 [SMILES: C[Si](C)(C)CCOCn1ccc2c(-c3cn(C(CC#N)C4CCCC4)nc3NCC(=O)O)ncnc21]

To a solution of ethyl-2-[1-(2-cyano-1-cyclopentylethyl)-4-(7-{[2-(trimethylsilyl) ethoxy]methyl}-7H-pyrrolo[2,3-d]pyrimidin-4-yl)-1H-pyrazol-3-ylamino]acetate (223 mg, 0.415 mmol, 1.0 eq.) in methanol and water (methanol/water=5/1) was added lithium hydroxide monohydrate (88 mg, 2.08 mmol, 5.0 eq.) at room temperature, and the resulting mixture was stirred overnight. After the reaction was completed, the solvent was removed in vacuo. The resulting mixture was diluted with water, and pH of the solution was adjusted with 2N diluted hydrochloric acid to 1-2, and the resultant was filtered to give 2-[1-(2-cyano-1- cyclopentylethyl)-4-(7-{[2-(trimethylsilyl)ethoxy]methyl}-7H-pyrrolo[2,3-d]pyrimidin-4-yl)-1H-pyrazol-3-ylamino] acetic acid (170 mg, 81% yield).

¹HNMR (400 MHz, CDCl₃) δ 8.80 (s, 1H), 8.06 (s, 1H), 7.37 (d, J=3.2 Hz, 1H), 6.68 (d, J=3.2 Hz, 1H), 5.67 (s, 2H), 4.22 (d, J=3.6 Hz, 2H), 4.10-4.03 (m, 1H), 3.53 (t, J 8.0 Hz, 2H), 3.06 (dd, J=8.4 Hz, J=4.0 Hz, 1H), 2.91 (dd, J=16.4 Hz, J=2.8 Hz, 1H), 2.56-2.54 (m, 1H), 1.95-1.91 (m, 1H), 1.72-1.23 (m, 4H), 1.58-1.20 (m, 3H), 0.94-0.89 (m, 2H), 0.00 (s, 9H).

m/z=510[M+1]⁺.

Step C: 3-cyclopentyl-3-[3-(2-morpholinyl-2-oxo-ethylamino)-4-(7-{[2-(trimethylsilyl)ethoxy]methyl}-7H-pyrrolo[2,3-d]pyrimidin-4-yl)-1H-pyrazol-1-yl]propionitrile

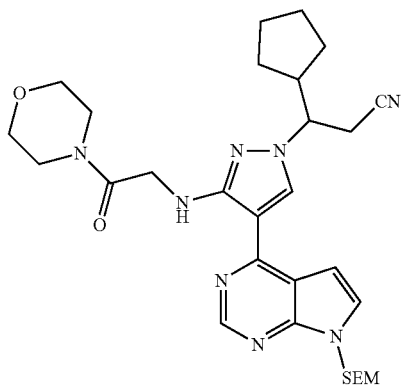 [SMILES: C[Si](C)(C)CCOCn1ccc2c(-c3cn(C(CC#N)C4CCCC4)nc3NCC(=O)N3CCOCC3)ncnc21]

Morpholine (10.3 mg, 0.118 mmol, 1.2 eq.), HATU (27 mg, 0.07 mmol, 0.7 eq.) and 2-[1-(2-cyano-1-cyclopentyl-ethyl)-4-(7-{[2-(trimethylsilyl)ethoxy]methyl}-7H-pyrrolo[2,3-d]pyrimidin-4-yl)-1H-pyrazol-3-ylamino]acetic acid (50 mg, 0.098 mmol, 1.0 eq.) were dissolved in DMF at room temperature. The reaction liquid was stirred and cooled to 0° C., and DIEA (19 mg, 0.147 mmol, 1.5 eq.) was added thereto. The reaction liquid was stirred overnight. After the reaction was completed, the resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give 3-cyclopentyl-3-[3-(2-morpholinyl-2-oxoethylamino)-4-(7-{[2-(trimethylsilyl)ethoxy]methyl}-7H-pyrrolo[2,3-d]pyrimidin-4-yl)-1H-pyrazol-1-yl]propionitrile (42 mg, 74% yield).

¹HNMR (400 MHz, CDCl₃): δ 8.94 (s, 1H), 8.08 (s, 1H), 7.38 (d, J=3.6 Hz, 1H), 6.73 (d, J=3.6 Hz, 1H), 5.72 (s, 2H), 4.30 (s, 2H), 4.12-4.06 (m, 1H), 3.93-3.70 (m, 6H), 3.62-3.57 (m, 4H), 3.14 (dd, J=17.2 Hz, J=8.0 Hz, 1H), 2.96 (dd, J=17.2 Hz, J=7.6 Hz, 1H), 2.63-2.61 (m, 1H), 2.03-1.98 (m, 1H), 1.82-1.63 (m, 4H), 1.38-1.29 (m, 3H), 0.97-0.94 (m, 2H), 0.00 (s, 9H).

m/z=579[M+1]⁺.

Step D: 3-cyclopentyl-3-[3-(2-morpholinyl-2-oxo-ethylamino)-4-(7H-pyrrolo[2,3-d]pyrimidin-4-yl)-1H-pyrazol-1-yl]propionitrile

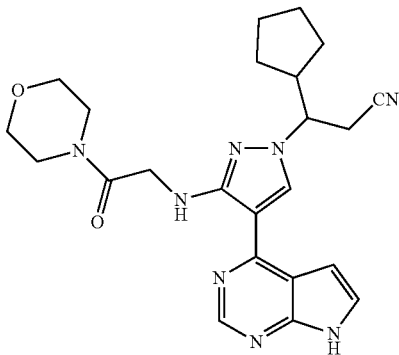 [SMILES: N#CCC(C1CCCC1)n1cc(-c2ncnc3[nH]ccc23)c(NCC(=O)N2CCOCC2)n1]

The compound of Example 14 was prepared according to the step H of Example 1, except that 3-[3-amino-4-(7-{[2-(trimethylsilyl)ethoxy]methyl)}-7H-pyrrolo[2,3-d]pyrimidin-4-yl)-1H-pyrazol-1-yl]-3-cyclopentylpropanenitrile was replaced with 3-cyclopentyl-3-[3-(2-morpholinyl-2-oxoethylamino)-4-(7-{[2-(trimethylsilyl)ethoxy]methyl}-7H-pyrrolo[2,3-d]pyrimidin-4-yl)-1H-pyrazol-1-yl]propionitrile.

¹HNMR (400 MHz, CDCl₃) δ 10.21 (s, 1H), 8.80 (s, 1H), 8.02 (s, 1H), 7.27 (d, J=3.2 Hz, 1H), 6.60 (d, J=3.2 Hz, 1H), 4.25 (s, 2H), 4.02-4.07 (m, 1H), 3.64-3.80 (m, 6H), 3.57-3.61 (m, 2H), 3.09 (dd, J=16.8 Hz, J=8.0 Hz, 1H), 2.91 (dd, J=16.8 Hz, J=4.0 Hz, 1H), 2.52-2.63 (m, 1H), 1.94-2.07 (m, 1H), 1.55-1.81 (m, 4H), 1.25-1.32 (m, 3H).

m/z=449[M+1]⁺.

Example 15: Ethyl 4-[1-(2-cyano-1-cyclopentyl-ethyl)-4-(7H-pyrrolo[2,3-d]pyrimidin-4-yl)-1H-pyrazol-3-ylamino]-4-oxobutanoate

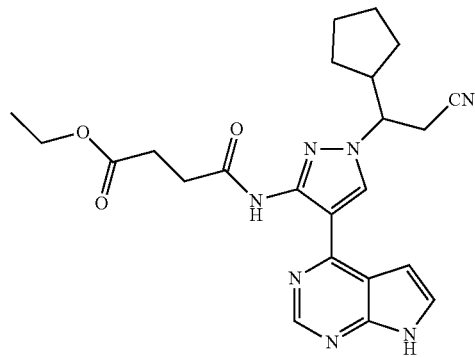 [SMILES: CCOC(=O)CCC(=O)Nc1nn(C(CC#N)C2CCCC2)cc1-c1ncnc2[nH]ccc12]

Step A: Ethyl 4-[1-(2-cyano-1-cyclopentylethyl)-4-(7-{[2-(trimethylsilyl) ethoxy]methyl}-7H-pyrrolo[2,3-d]pyrimidin-4-yl)-1H-pyrazol-3-ylamino]-4-oxobutanoate

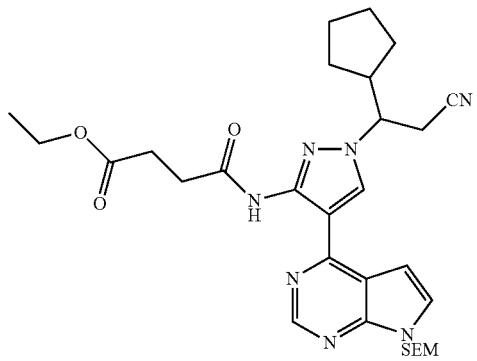 [SMILES: CCOC(=O)CCC(=O)Nc1nn(C(CC#N)C2CCCC2)cc1-c1ncnc2c1ccn2COCC[Si](C)(C)C]

To a solution of 3-[3-amino-4-(7-{[2-(trimethylsilyl)ethoxy]methyl)}-7H-pyrrolo[2,3-d]pyrimidin-4-yl)-1H-pyrazol-1-yl]-3-cyclopentylpropanenitrile (250 mg, 0.553 mmol, 1.0 eq., prepared from the step G of Example 1) and N,N-diisopropylethylamine (86 mg, 0.664 mmol, 1.2 eq.) in dichloromethane (10 mL) was added ethyl succinyl chloride (109 mg, 0.664 mmol, 1.2 eq.) under stirring in an ice bath. The reaction liquid was stirred for 3 hrs at room temperature, and then N,N-diisopropylethylamine (0.2 mL) and ethyl succinyl chloride (0.1 mL) were added additionally. After reacting overnight, the resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give the titled compound (237 mg, 74% yield).

$^1$H NMR (CDCl$_3$) δ 11.63-11.68 (1H, brs), 8.85 (1H, s), 8.18 (1H, s), 7.41 (1H, d, J=3.6 Hz), 6.72 (1H, d, J=3.6 Hz), 5.68 (2H, s), 4.22-4.36 (1H, m), 4.16 (2H, q, J=7.2 Hz), 3.55 (2H, t, J=8.4 Hz), 3.13 (1H, dd, J=17.2 Hz, 7.6 Hz), 2.99 (1H, dd, J=17.2 Hz, 3.6 Hz), 2.62-2.88 (5H, m), 1.93-2.01 (1H, m), 1.60-1.80 (4H, m), 1.28-1.34 (3H, m), 1.26 (3H, t, J=7.2 Hz), 0.93 (2H, t, J=8.4 Hz), −0.04 (9H, s).
m/z=580[M+1]$^+$.

Step B: Ethyl 4-[1-(2-cyano-1-cyclopentylethyl)-4-(7H-pyrrolo[2,3-d]pyrimidin-4-yl)-1H-pyrazol-3-ylamino]-4-oxobutanoate

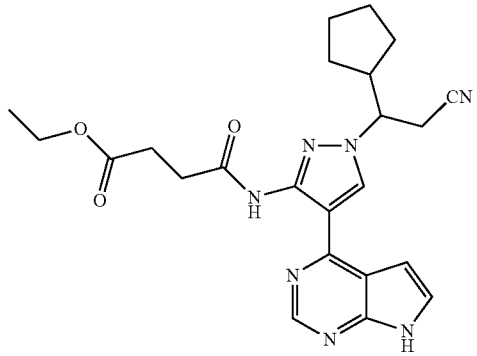 [SMILES: CCOC(=O)CCC(=O)Nc1nn(C(CC#N)C2CCCC2)cc1-c1ncnc2[nH]ccc12]

The compound (237 mg, 0.409 mmol, 1 eq.) obtained from the above step was dissolved in acetonitrile (4 mL) and water (0.5 mL), and LiBF$_4$ (383 mg, 4.09 mmol, 10 eq.) was added. The mixture was stirred overnight at 90° C. and then cooled to room temperature.

An ammonia solution was added, and the resulting mixture was stirred for 1 hr. Brine and ethyl acetate were added, and the resulting mixture was extracted with ethyl acetate. The combined organic phase was dried over sodium sulfate, filtered and concentrated in vacuo.

The resulting residue was separated by column chromatography on silica gel column to give the titled compound.

$^1$H NMR (CDCl$_3$) δ 11.65 (1H, s), 9.78 (1H, s), 8.80 (1H, s), 8.23 (1H, s), 7.38 (1H, d, J=3.6 Hz), 6.68 (1H, d, J=3.6 Hz), 4.29-4.36 (1H, m), 4.25 (2H, q, J=7.2 Hz), 3.24 (1H, dd, J=17.2 Hz, 8.0 Hz), 3.04 (1H, dd, J=17.2 Hz, 3.6 Hz), 2.82-2.94 (4H, m), 2.67-2.76 (1H, m), 1.97-2.05 (1H, m), 1.57-1.83 (4H, m), 1.34 (3H, t, J=7.2 Hz), 1.28-1.32 (3H, m).
m/z=450[M+1]$^+$.

Example 16: 3-cyclopentyl-3-[3-(succinimid-1-yl)-4-(7H-pyrrolo[2,3-d]pyrimidin-4-yl)-1H-pyrazol-1-yl]propionitrile

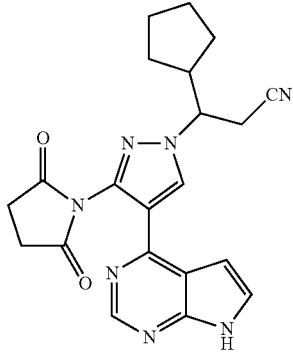 [SMILES: N#CCC(C1CCCC1)n1cc(-c2ncnc3[nH]ccc23)c(N2C(=O)CCC2=O)n1]

Step A: 3-cyclopentyl-3-[3-(succinimid-1-yl)-4-(7-{[2-(trimethylsilyl)ethoxy]methyl}-7H-pyrrolo[2,3-d]pyrimidin-4-yl)-1H-pyrazol-1-yl]propionitrile

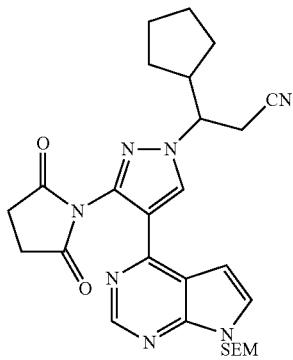 [SMILES: C[Si](C)(C)CCOCn1ccc2c(-c3cn(C(CC#N)C4CCCC4)nc3N3C(=O)CCC3=O)ncnc21]

3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (200 mg, 0.443 mmol, 1.0 eq., prepared from the step G of Example 1) and succinic anhydride (88 mg, 0.879 mmol, 2.0 eq.) were dissolved in 1,2-dichloroethane (10 mL), and the mixture was refluxed overnight. The resulting mixture was concentrated in vacuo and separated by column chromatography on silica gel column to give the titled compound (103 mg, 44% yield).

$^1$H NMR (CDCl$_3$) δ 8.70 (1H, s), 8.31 (1H, s), 7.37 (1H, d, J=4.0 Hz), 6.67 (1H, d, J=4.0 Hz), 5.64 (2H, s), 4.26-4.32 (1H, m), 3.50 (2H, t, J=8.4 Hz), 3.08 (1H, dd, J=17.2 Hz, 6.8 Hz), 3.02 (1H, dd, J=17.2 Hz, 4.8 Hz), 2.94 (4H, s), 2.62-2.70 (1H, m), 1.96-2.05 (1H, m), 1.59-1.77 (4H, m), 1.27-1.34 (3H, m), 0.90 (2H, t, J=8.4 Hz), −0.06 (9H, s). m/z=534[M+1]$^+$.

Step B: 3-cyclopentyl-3-[3-(succinimid-1-yl)-4-(7H-pyrrolo[2,3-d]pyrimidin-4-yl)-1H-pyrazol-1-yl]propionitrile

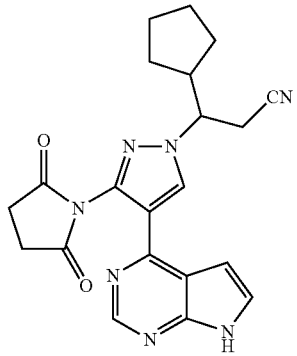 [SMILES: N#CCC(C1CCCC1)n1cc(-c2ncnc3[nH]ccc23)c(N2C(=O)CCC2=O)n1]

The compound (103 mg, 0.193 mmol, 1 eq.) obtained from the above step was dissolved in acetonitrile (4 mL) and water (0.5 mL), and LiBF$_4$ (181 mg, 1.93 mmol, 10 eq.) was added. The mixture was stirred overnight at 90° C. and cooled to room temperature. An ammonia solution was added, and the mixture was stirred for 1 hr. Brine and ethyl acetate were added, and the resulting mixture was extracted with ethyl acetate. The combined organic phase was dried over sodium sulfate, filtered and concentrated in vacuo. The resulting residue was separated by column chromatography on silica gel column to give the titled compound.

$^1$H NMR (CDCl$_3$) δ 9.41-9.46 (1H, brs), 8.69 (1H, s), 8.34 (1H, s), 7.32 (1H, d, J=3.2 Hz), 6.63 (1H, d, J=3.2 Hz), 4.30-4.35 (1H, m), 3.11 (1H, dd, J=17.2 Hz, 7.2 Hz), 3.04 (1H, dd, J=17.2 Hz, 4.4 Hz), 2.96 (4H, s), 2.61-2.69 (1H, m), 1.95-2.04 (1H, m), 1.56-1.78 (4H, m), 1.28-1.33 (3H, m). m/z=404[M+1]$^+$.

Example 17: 3-[3-(3-morpholin-4-carbonyl)cyclobutylamino-4-(7H-pyrrolo[2,3-d]pyrimidin-4-yl)-1H-pyrazolyl]-3-cyclopentylpropanenitrile

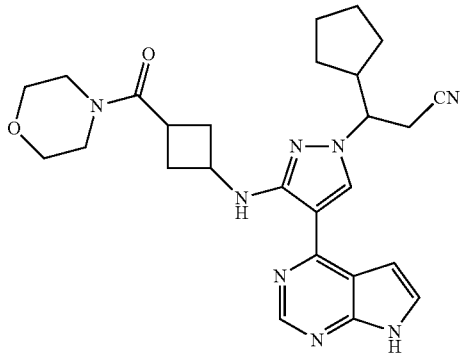 [SMILES: N#CCC(C1CCCC1)n1cc(-c2ncnc3[nH]ccc23)c(NC2CC(C(=O)N3CCOCC3)C2)n1]

Step A: methyl 3-oxocyclobutanecarboxylate

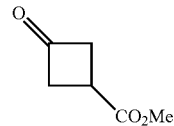

Concentrated sulfuric acid (0.2 mL) was added dropwise to a solution of 3-oxocyclobutanecarboxylic acid (1 g, 8.77 mmol) in methanol, and the mixture was refluxed at 75° C. After the starting materials were reacted completely, the reaction was quenched by adding sodium bicarbonate, and the solvent was removed. The resulting residue was extracted to give methyl 3-oxocyclobutanecarboxylate (1.1 g, 99% yield).

$^1$HNMR (400 MHz, CDCl$_3$) δ 3.22-3.34 (m, 3H), 3.40-3.47 (m, 2H), 3.78 (s, 3H).

Step B: methyl 3-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]cyclobutanecarboxylate

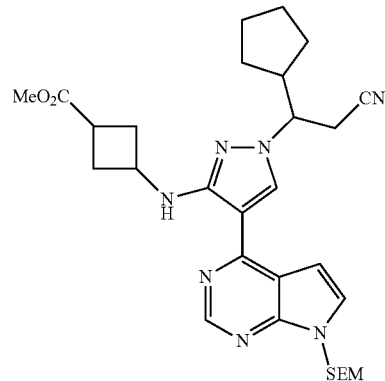 [SMILES: COC(=O)C1CC(Nc2nn(C(CC#N)C3CCCC3)cc2-c2ncnc3c2ccn3COCC[Si](C)(C)C)C1]

To a solution of 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (410.0 mg, 0.91 mmol, prepared from the step G of Example 1) in 1,2-dichloroethane were added methyl 3-oxocyclobutanecarboxylate (117.0 mg, 0.91 mmol), acetic acid (54.6 mg, 0.91 mmol) and sodium cyanoborohydride (80.0 mmg, 1.27 mmol) in an ice bath. The ice bath was removed and the mixture was stirred overnight at room temperature. After the starting materials were reacted completely, the reaction was quenched by adding saturated ammonium chloride. The resulting mixture was washed with water and extracted with ethyl acetate to give the titled compound (172 mg, 34% yield).

$^1$HNMR (400 MHz, CDCl$_3$) δ 8.85 (s, 1H), 8.00 (s, 1H), 7.36 (m, 1H), 6.93 (brs, 1H), 6.75 (s, 1H), 5.69 (s, 2H), 4.91 (d, 1H), 4.00-4.05 (m, 1H), 3.70 (s, 3H), 3.55 (t, J=8.4 Hz, 2H), 3.00-3.20 (m, 1H), 1.80-2.95 (m, 8H), 1.25-1.80 (m, 7H), 0.91 (t, J=8.0, 2H), −0.05 (s, 9H).

m/z=564[M+1]$^+$.

Step C: 3-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]cyclobutanecarboxylic acid

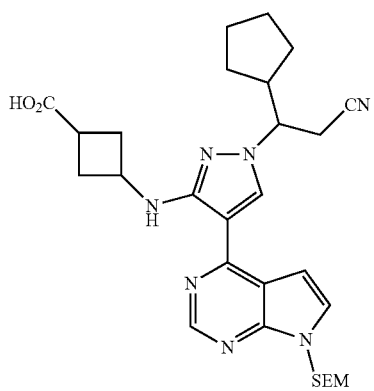 [SMILES: C[Si](C)(C)CCOCn1ccc2c(-c3cn(C(CC#N)C4CCCC4)nc3NC3CC(C(=O)O)C3)ncnc21]

To a solution of methyl 3-[1-(2-cyano-1-cyclopentylethyl)-4-(7-{[2-(trimethylsilyl) ethoxy]methyl}-7H-pyrrolo[2,3-d]pyrimidin-4-yl)-1H-pyrazol-3-ylamino]cyclobutanecarboxylate (84 mg, 0.144 mmol) in methanol was added dropwise an aqueous solution of lithium hydroxide monohydrate (30 mmg, 0.72 mmol) in an ice bath. The mixture was stirred overnight at room temperature. After the starting materials were reacted completely, the solvent was removed. The resulting mixture was washed with water, extracted with ethyl acetate, dried over anhydrous sodium sulfate, and column chromatographed (ethyl acetate:petroleum ether=1:1, followed by methanol) to give the titled compound (29 mg, 37% yield).

Step C: 3-{3-[3-(morpholin-4-carbonyl)cyclobutylamino]-4-(7-{[2-(trimethylsilyl) ethoxy]methyl}-7H-pyrrolo[2,3-d]pyrimidin-4-yl)-1H-pyrazolyl}-3-cyclopentylpropanenitrile

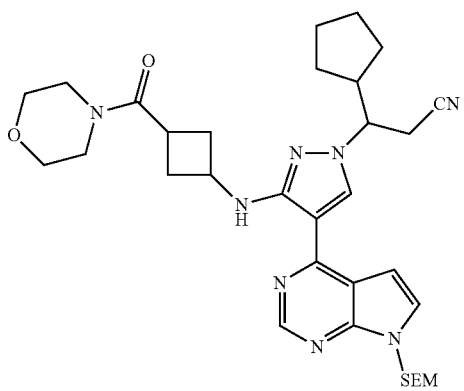 [SMILES: C[Si](C)(C)CCOCn1ccc2c(-c3cn(C(CC#N)C4CCCC4)nc3NC3CC(C(=O)N4CCOCC4)C3)ncnc21]

To a solution of 3-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]cyclobutanecarboxylic acid (25 mg, 0.0455 mmol) in DMF were successively added morpholine (4.78 mg, 0.0545 mmol) and HBTU (17.3 mg, 0.0455 mmol) in an ice bath. The mixture was stirred for 5 min, DIEA (11.8 mg, 0.091 mmol) was added thereto and the resulting mixture was stirred at room temperature. After the starting materials were reacted completely as monitored by TLC, the reaction was quenched by adding water. The resulting mixture was extracted with ethyl acetate, and dried over anhydrous sodium sulfate to give a crude product which was directly used in the next step.

Step D: 3-[3-(3-(morpholin-4-carbonyl)cyclobutylamino)-4-(7H-pyrrolo[2,3-d]pyrimidin-4-yl)-1H-pyrazolyl]-3-cyclopentylpropanenitrile

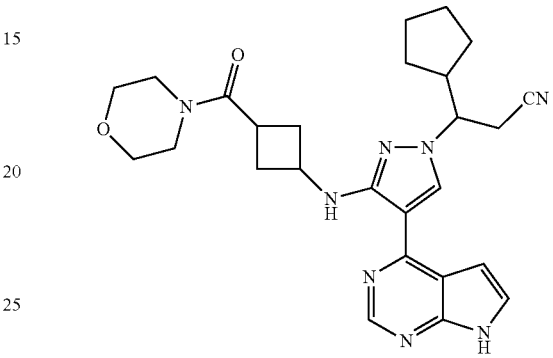

The crude product obtained from the step C was dissolved in dichloromethane, and trifluoroacetic acid (3 mL) was added thereto. The mixture was stirred overnight at room temperature. After the solvent was removed, a yellow oily material was obtained, and it was dissolved in methanol. Two drops of ethylenediamine were added thereto, and the mixture was stirred at room temperature. After the starting materials were reacted completely as monitored by TLC, the solvent was removed. The resulting mixture was washed with water and extracted with ethyl acetate to give the titled compound (17 mg, yield 76% over two steps).

$^1$HNMR (400 MHz, CDCl$_3$) δ 9.53 (brs, 1H), 8.76 (s, 1H), 8.0 (s, 1H), 7.35 (brs, 1H), 7.30 (s, 1H), 6.65 (s, 1H), 4.24-4.34 (m, 1H), 4.00-4.03 (m, 1H), 3.50-3.65 (m, 6H), 3.40-3.43 (m, 2H), 3.05-3.12 (m, 1H), 2.88-2.92 (m, 2H), 2.37-2.72 (m, 5H), 1.90-1.98 (m, 1H), 1.10-1.80 (m, 7H).
m/z=489[M+1]$^+$.

Example 18: 3-[3-bromo-4-(5-bromo-7H-pyrrolo[2,3-d]pyrimidin-4-yl)-1H-pyrazol-1-yl]-3-cyclopentyl-propanenitrile

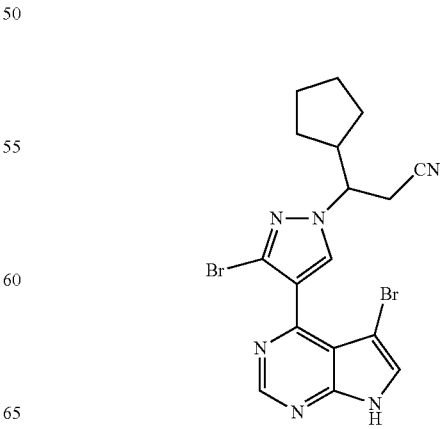

Step A: 3-[3-bromo-4-(5-bromo-7-{[2-(trimethylsilyl)ethoxy]methyl}-7H-pyrrolo[2,3-d]pyrimidin-4-yl)-1H-pyrazol-1-yl]-3-cyclopentylpropanenitrile

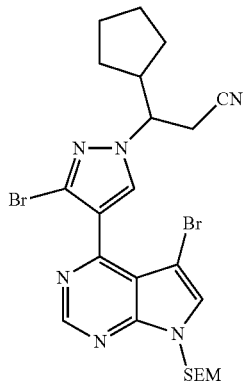 [SMILES: C[Si](C)(C)CCOCn1cc(Br)c2c(-c3cn(C(CC#N)C4CCCC4)nc3Br)ncnc21]

To a solution of 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (200 mg, 0.442 mmol, 1.0 eq., prepared from the step G of Example 1) in acetonitrile was added copper bromide (198 mg, 0.886 mmol, 2.0 eq.) at room temperature. The reaction liquid was protected with nitrogen gas and stirred for 0.5 hr at 60° C. Tert-butyl nitrite (68 mg, 0.66 mmol, 1.5 eq.) was added dropwise to the reaction liquid, and the mixture was stirred for 3 hrs at 60° C. The resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give 3-[3-bromo-4-(5-bromo-7-{[2-(trimethylsilyl) ethoxy]methyl}-7H-pyrrolo[2,3-d]pyrimidin-4-yl)-1H-pyrazol-1-yl]-3-cyclopentylpropanenitrile (123 mg, 54% yield).

$^1$HNMR (400 MHz, CDCl$_3$): δ 8.99 (s, 1H), 7.86 (s, 1H), 7.44 (s, 1H), 5.77 (s, 2H), 4.21-4.19 (dd, J=2.4 Hz, J=1.2 Hz, 1H), 3.58 (t, J=8.4 Hz, 2H), 3.16-3.10 (m, 1H), 2.95 (dd, J=16.8 Hz, J=4.0 Hz, 1H), 2.63-2.56 (m, 1H), 2.00-1.90 (m, 1H), 1.71-1.56 (m, 4H), 1.32-1.17 (m, 3H), 0.96-0.86 (m, 2H), 0.00 (s, 9H).

m/z=595[M+1]$^+$.

Step B: 3-[3-bromo-4-(5-bromo-7H-pyrrolo[2,3-d]pyrimidin-4-yl)-1H-pyrazol-1-yl]-3-cyclopentylpropanenitrile

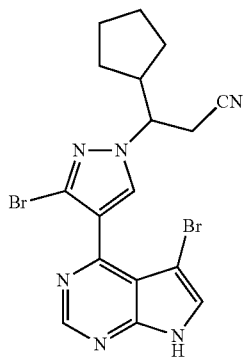 [SMILES: N#CCC(C1CCCC1)n1cc(-c2ncnc3[nH]cc(Br)c23)c(Br)n1]

The compound of Example 18 was prepared according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with 3-[3-bromo-4-(5-bromo-7-{[2-(trimethylsilyl)ethoxy]methyl}-7H-pyrrolo[2,3-d]pyrimidin-4-yl)-1H-pyrazol-1-yl]-3-cyclopentylpropanenitrile.

$^1$HNMR (400 MHz, CDCl$_3$) δ 9.71-9.73 (brs, 1H), 8.99 (s, 1H), 7.89 (s, 1H), 7.42 (s, 1H), 4.18-4.31 (m, 1H), 3.14 (dd, J=17.2 Hz, J=8.8 Hz, 1H), 2.96 (dd, J=17.2 Hz, J=4.0 Hz, 1H), 2.58-2.64 (m, 1H), 1.90-2.01 (m, 1H), 1.59-1.76 (m, 4H), 1.25-1.32 (m, 3H).

m/z=465[M+1]$^+$.

Example 19: 3-[3-bromo-4-(7H-pyrrolo[2,3-d]pyrimidin-4-yl)-1H-pyrazol-1-yl]-3-cyclopentylpropanenitrile

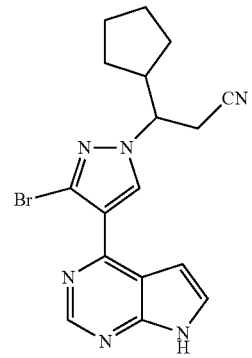 [SMILES: N#CCC(C1CCCC1)n1cc(-c2ncnc3[nH]ccc23)c(Br)n1]

Step A: 3-[3-bromo-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile

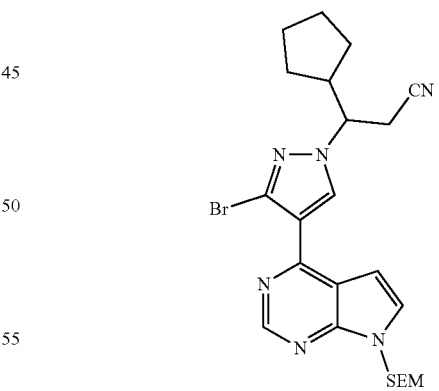

3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (100 mg, 0.221 mmol, 1.0 eq., prepared from the step G of Example 1) was added in 2N diluted hydrochloric acid solution under stirring in an ice bath and the reaction liquid was stirred for 0.5 hr. A majority of the aqueous solution of sodium nitrite (61 mg, 0.884 mmol, 4.0 eq.) was rapidly added to the reaction liquid, and then the rest of the aqueous solution and sodium bromide (23 mg, 0.33 mmol, 1.5 eq.) were added thereto. The reaction liquid was stirred for 0.5 hr at 0° C. The resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give 3-[3-bromo-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (9 mg, 8% yield).

$^1$HNMR (400 MHz, CDCl$_3$): δ 9.00 (s, 1H), 8.10 (s, 1H), 7.43 (s, 1H), 6.82 (s, 1H), 5.73 (s, 2H), 4.30-4.18 (m, 1H), 3.61 (t, J=8.4 Hz, 2H), 2.95 (dd, J=17.2 Hz, J=8.4 Hz, 1H), 3.01 (dd, J=16.8 Hz, J=8.0 Hz, 1H), 2.72-2.61 (m, 1H), 2.05-1.99 (m, 1H), 1.82-1.64 (m, 4H), 1.47-1.18 (m, 3H), 1.09-0.76 (m, 2H), 0.00 (s, 9H).

m/z=516[M+1]$^+$.

Step B: 3-[3-bromo-4-(7H-pyrrolo[2,3-d]pyrimidin-4-yl)-1H-pyrazol-1-yl]-3-cyclopentylpropanenitrile

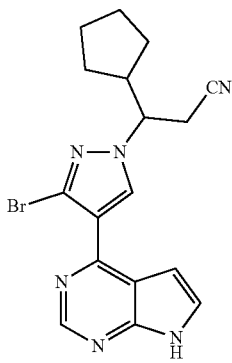 [SMILES: N#CCC(C1CCCC1)n1cc(-c2ncnc3[nH]ccc23)c(Br)n1]

The compound of Example 19 was prepared according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with 3-[3-bromo-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile.

$^1$HNMR (400 MHz, CDCl$_3$) δ 10.01-10.08 (brs, 1H), 8.95 (s, 1H), 8.04 (s, 1H), 3.38-7.40 (m, 1H), 6.76-6.78 (m, 1H), 4.19-4.25 (m, 1H), 3.12 (dd, J=17.2 Hz, J=8.4 Hz, 1H), 2.97 (dd, J=17.2 Hz, J=4.0 Hz, 1H), 2.57-2.69 (m, 1H), 1.93-2.07 (m, 1H), 1.58-1.79 (m, 4H), 1.28-1.32 (m, 3H).

m/z=386[M+1]$^+$.

Example 20: (E)-4-[1-(2-cyano-1-cyclopentylethyl)-4-(7H-pyrrolo[2,3-d]pyrimidin-4-yl)-1H-pyrazol-3-ylamino]-N-hydroxyl-2-butenamide

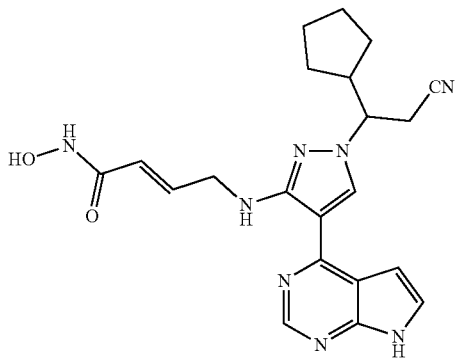 [SMILES: N#CCC(C1CCCC1)n1cc(-c2ncnc3[nH]ccc23)c(NC/C=C/C(=O)NO)n1]

Step A: (E)-methyl-4-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]-2-butenoate

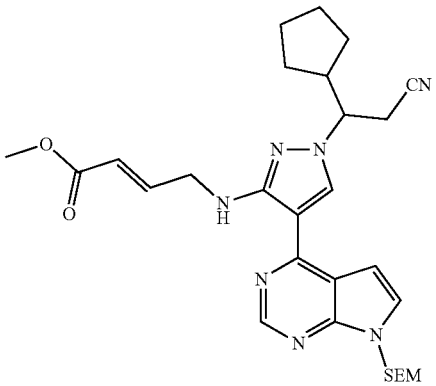 [SMILES: COC(=O)/C=C/CNc1nn(C(CC#N)C2CCCC2)cc1-c1ncnc2c1ccn2COCC[Si](C)(C)C]

The compound was prepared according to the step A of Example 11, except that 4-(2-chloroethyl)morpholine was replaced with a side chain methyl 4-bromocrotonate.

$^1$HNMR (400 MHz, CDCl$_3$) δ 8.77 (s, 1H), 8.02 (s, 1H), 7.47 (t, J=5.6 Hz, 1H), 7.33 (s, 1H), 7.16-7.10 (m, 1H), 6.68 (s, 1H), 6.07 (d, J=15.6 Hz, 1H), 5.66 (s, 2H), 4.22 (d, J=9.2 Hz, 2H), 4.04-4.01 (m, 1H), 3.72 (s, 3H), 5.53 (t, J=8.4 Hz, 2H), 3.08 (dd, J=16.8 Hz, J 8.4 Hz, 1H), 2.88 (dd, J=13.2 Hz, J=6.4 Hz, 1H), 2.62-2.48 (m, 1H), 1.97-1.92 (m, 1H), 1.72-1.56 (m, 4H), 1.33-1.21 (m, 3H), 0.92-0.86 (m, 2H), 0.00 (s, 9H).

m/z=550[M+1]$^+$.

Step B: (E)-4-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]-2-butenoic acid

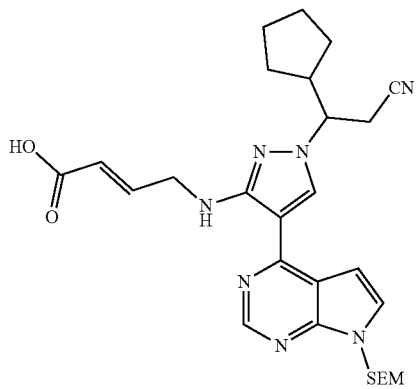 [SMILES: C[Si](C)(C)CCOCn1ccc2c(-c3cn(C(CC#N)C4CCCC4)nc3NC/C=C/C(=O)O)ncnc21]

To a solution of (E)-methyl-4-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]-2-butenoate (215 mg, 0.391 mmol, 1.0 eq.) in tetrahydrofuran and water (tetrahydrofuran/water=5/1) was added lithium hydroxide monohydrate (91 mg, 2.0 mmol, 5.0 eq.) at room temperature, and the mixture was stirred overnight at room temperature. After the reaction was completed, the solvent was removed in vacuo. The resulting mixture was diluted with water, and pH of the solution was adjusted with 2N diluted hydrochloric acid to 1-2, and the mixture was filtered to give (E)-4-[1-(2-cyano-1-cyclopentylethyl)-4-(7-{[2-(trimethyl-silyl) ethoxy]methyl}-7H-pyrrolo[2,3-d]pyrimidin-4-yl)-1H-pyrazol-3-ylamino]-2-butenoic acid (91 mg, 44% yield).

Step C: (E)-4-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]-N-(tetra-hydro-2H-pyran-2-oxy)-2-butenamide

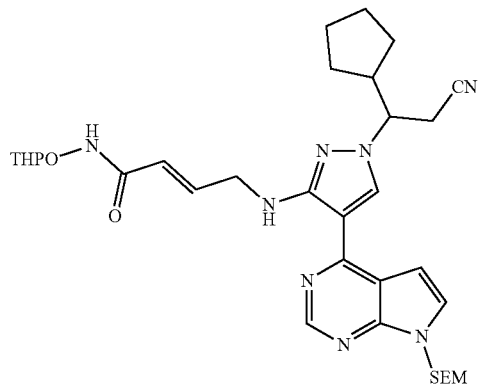

O-(tetrahydro-2H-pyran-2-yl)hydroxyl amine (40.0 mg, 0.34 mmol, 2.0 eq.), HATU (65 mg, 0.17 mmol, 1.0 eq.) and (E)-4-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]-2-butenoic acid (91 mg, 0.17 mmol, 1.0 eq.) were dissolved in DMF at room temperature. The reaction liquid was stirred and cooled to 0° C., and DIEA (44 mg, 0.34 mmol, 2.0 eq.) was added thereto. The reaction liquid was stirred overnight. After the reaction was completed, the mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give the titled compound (66 mg, 62% yield).
m/z=635[M+1]$^+$.

Step D: (E)-4-[1-(2-cyano-1-cyclopentylethyl)-4-(7H-pyrrolo[2,3-d]pyrimidin-4-yl)-1H-pyrazol-3-ylamino]-N-hydroxyl-2-butenamide

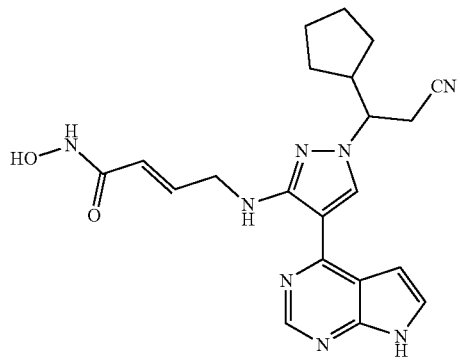 [SMILES: N#CCC(C1CCCC1)n1cc(-c2ncnc3[nH]ccc23)c(NC/C=C/C(=O)NO)n1]

The compound of Example 20 was prepared according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with (E)-4-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]-N-(tetrahydro-2H-pyran-2-oxy)-2-butenamide.
m/z=421 [M+1]$^+$.

Example 21: 3-[1-(2-cyano-1-cyclopentylethyl)-4-(7H-pyrrolo[2,3-d]pyrimidin-4-yl)-1H-pyrazol-3-ylamino]-N-hydroxylpropanamide

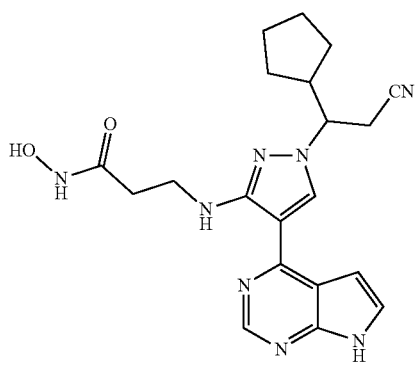 [SMILES: N#CCC(C1CCCC1)n1cc(-c2ncnc3[nH]ccc23)c(NCCC(=O)NO)n1]

Step A: ethyl-3-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]propionate

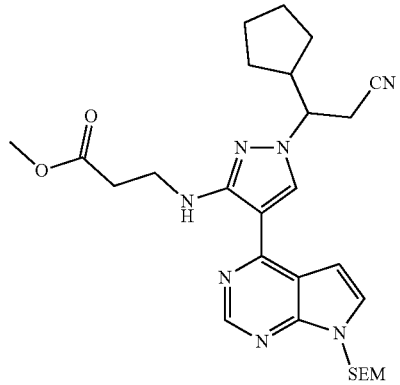 [SMILES: COC(=O)CCNc1nn(C(CC#N)C2CCCC2)cc1-c1ncnc2c1ccn2COCC[Si](C)(C)C]

The compound was prepared according to the step A of Example 11, except that 4-(2-chloroethyl)morpholine was replaced with a side chain ethyl 3-bromopropionate.
$^1$HNMR (400 MHz, CDCl$_3$) δ 8.76 (s, 1H), 8.00 (s, 1H), 7.40 (brs, 1H), 7.32 (d, J 3.6 Hz, 1H), 6.66 (d, J=4.0 Hz, 1H), 5.65 (s, 2H), 4.19-4.14 (m, 2H), 4.03-3.99 (m, 1H), 3.72 (d, J=6.8 Hz, 2H), 3.52 (d, J=8.0 Hz, 2H), 3.11 (dd, J=16.4 Hz, J=8.0 Hz, 1H), 2.92 (dd, J=16.8 Hz, J=3.6 Hz, 1H), 2.75 (t, J=6.4 Hz, 2H), 2.64-2.53 (m, 1H), 1.98-1.88 (m, 1H), 1.67-1.57 (m, 5H), 1.30-1.22 (m, 5H), 0.91 (d, J=8.0 Hz, 2H), −0.06 (s, 9H).
m/z=552[M+1]$^+$.

Step B: 3-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]propionic acid

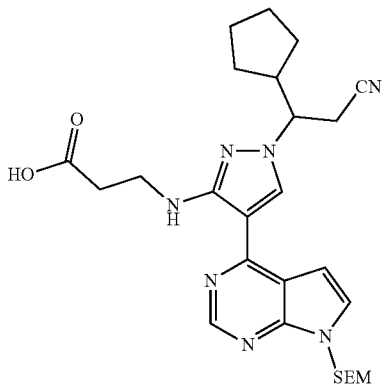 [SMILES: C[Si](C)(C)CCOCn1ccc2c(-c3cn(C(CC#N)C4CCCC4)nc3NCCC(=O)O)ncnc21]

The compound was prepared according to the step B of Example 14, except that ethyl-2-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]acetate was replaced with ethyl-3-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]propionate.

$^1$HNMR (400 MHz, CDCl$_3$) δ 8.79 (s, 1H), 8.04 (s, 1H), 7.9-7.4 (brs, 1H), 7.35 (d, J 4.0 Hz, 1H), 6.68 (d, J=3.6 Hz, 1H), 5.67 (s, 2H), 4.08-4.01 (m, 1H), 3.73 (t, J=6.0 Hz, 2H), 3.53 (t, J=8.4 Hz, 2H), 3.09 (dd, J=17.2 Hz, J=8.8 Hz, 1H), 2.94-2.83 (m, 3H), 2.64-2.56 (m, 1H), 1.96-1.93 (m, 1H), 1.74-1.59 (m, 4H), 1.30-1.23 (m, 3H), 0.91 (t, J=8.4 Hz, 2H), −0.06 (s, 9H).

m/z=524[M+1]$^+$.

Step C: N-(benzyloxy)-3-[1-(2-cyano-1-cyclopentylethyl)-4-(7-{[2-(trimethylsilyl) ethoxy]methyl}-7H-pyrrolo[2,3-d]pyrimidin-4-yl)-1H-pyrazol-3-ylamino]propanamide

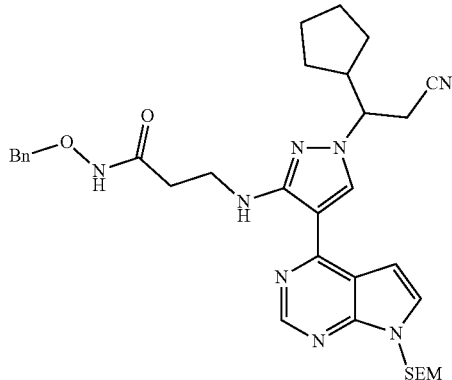 [SMILES: C[Si](C)(C)CCOCn1ccc2c(-c3cn(C(CC#N)C4CCCC4)nc3NCCC(=O)NOCc3ccccc3)ncnc21]

The compound was prepared according to the step C of Example 20, except that (E)-4-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]-2-butenoic acid was replaced with 3-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]propionic acid and O-(tetrahydro-2H-pyran-2-yl) hydroxyl amine was replaced with O-benzyl hydroxyl amine.

$^1$HNMR (400 MHz, CDCl$_3$) δ 9.08 (brs, 1H), 8.83 (s, 1H), 8.09 (s, 1H), 8.04 (s, 1H), 7.52 (brs, 1H), 7.42-7.30 (m, 5H), 6.73 (d, J=3.6 Hz, 1H), 5.72 (s, 2H), 4.92 (s, 2H), 4.04-3.99 (m, 1H), 3.78 (d, J=4.8 Hz, 2H), 3.60 (t, J=8.4 Hz, 2H), 3.03-2.95 (m, 2H), 2.67-2.59 (m, 3H), 1.99-1.96 (m, 1H), 1.81-1.64 (m, 4H), 1.50-1.28 (m, 3H), 1.00-0.93 (m, 2H), 0.00 (s, 9H).

m/z=629[M+1]$^+$.

Step D: 3-[1-(2-cyano-1-cyclopentylethyl)-4-(7H-pyrrolo[2,3-d]pyrimidin-4-yl)-1H-pyrazol-3-ylamino]-N-hydroxylpropanamide

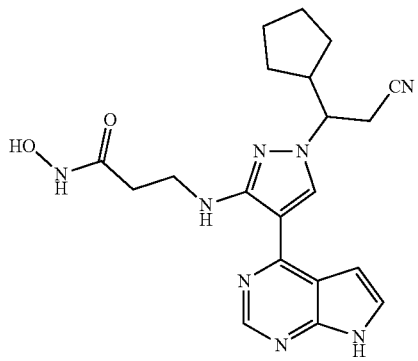 [SMILES: N#CCC(C1CCCC1)n1cc(-c2ncnc3[nH]ccc23)c(NCCC(=O)NO)n1]

The compound of Example 21 was prepared after removing SEM according to the step H of Example 1 and removing benzyl, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with N-(benzyloxy)-3-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-ylamino]propanamide.

m/z=409[M+1]$^+$.

Example 22: 3-[3-(2-cyanoethylamino)-4-(7H-pyrrolo[2,3-d]pyrimidin-4-yl)-1H-pyrazol-1-yl]-3-cyclopentylpropanenitrile

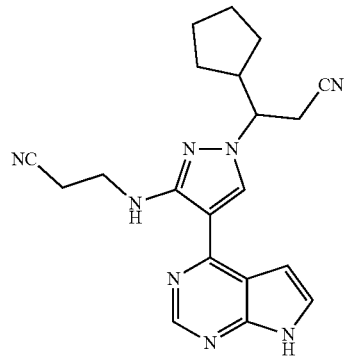 [SMILES: N#CCCNc1nn(C(CC#N)C2CCCC2)cc1-c1ncnc2[nH]ccc12]

Step A: 3-[1-(2-cyano-1-cyclopropylethyl)-4-(7-{[2-(trimethylsilyl)ethoxy]methyl}-7H-pyrrolo[2,3-d]pyrimidin-4-yl)-1H-pyrazol-3-ylamino]propanamide

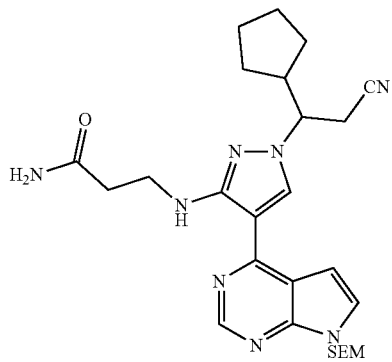 [SMILES: C[Si](C)(C)CCOCn1ccc2c(-c3cn(C(CC#N)C4CCCC4)nc3NCCC(N)=O)ncnc21]

To a solution of 3-[1-(2-cyano-1-cyclopropylethyl)-4-(7-{[2-(trimethylsilyl)ethoxy]methyl}-7H-pyrrolo[2,3-d]pyrimidin-4-yl)-1H-pyrazol-3-ylamino]propionic acid (1.0 eq., prepared from the step B of Example 21) in DMF was added carbonyldimidazole (1.5 eq.) under stirring in an ice bath. The resulting mixture was stirred for 0.5 hr at 0° C., then warmed to room temperature and stirred for 2 hrs. The ammonia gas was introduced into the reaction liquid and bubbled for 1 hr. The resulting mixture was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give the titled compound.

m/z=523 [M+1]$^+$.

Step B: 3-[3-(2-cyanoethylamino)-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile

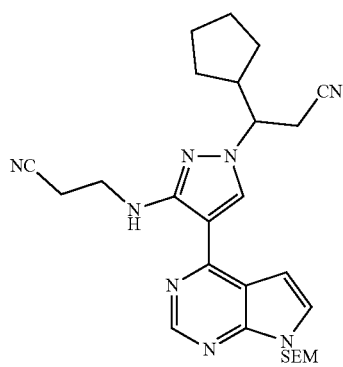 [SMILES: C[Si](C)(C)CCOCn1ccc2c(-c3cn(C(CC#N)C4CCCC4)nc3NCCC#N)ncnc21]

Under stirring in an ice bath, 3-[1-(2-cyano-1-cyclopropylethyl)-4-(7-{[2-(trimethylsilyl)ethoxy]methyl}-7H-pyrrolo[2,3-d]pyrimidin-4-yl)-1H-pyrazol-3-ylamino]propanamide (1.0 eq.) was dissolved in dichloromethane, and then triethylamine (5 eq.) and trifluoroacetic anhydride (2 eq.) were added. The reaction liquid was warmed to room temperature and stirred overnight. The resulting mixture was diluted with water and ethyl acetate, and extracted with ethyl acetate. The combined organic phase was dried over sodium sulfate, filtered and concentrated in vacuo. The resulting residue was separated by column chromatography on silica gel column to give the titled compound.

m/z=505[M+1]$^+$.

Step C: 3-[3-(2-cyanoethylamino)-4-(7H-pyrrolo[2,3-d]pyrimidin-4-yl)-1H-pyrazol-1-yl]-3-cyclopentyl-propanenitrile

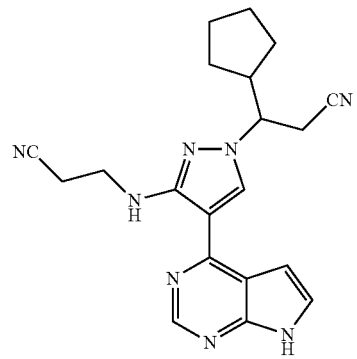 [SMILES: N#CCCNc1nn(C(CC#N)C2CCCC2)cc1-c1ncnc2[nH]ccc12]

The compound obtained from the above step was dissolved in acetonitrile (4 mL) and water (0.5 mL), and LiBF$_4$ (10 eq.) was added. The mixture was stirred overnight at 90° C. and cooled to room temperature. An ammonia solution was added, and the mixture was stirred for 1 hr. Brine and ethyl acetate were added, and the resulting mixture was extracted with ethyl acetate. The combined organic phase was dried over sodium sulfate, filtered and concentrated in vacuo. The resulting residue was separated by column chromatography on silica gel column to give the titled compound.

m/z=375[M+1]$^+$.

Example 23: 1-[1-(2-cyano-1-cyclopentylethyl)-4-(7H-pyrrolo[2,3-d]pyrimidin-4-yl)-1H-pyrazol-3-yl]-3-(5-methyl-1,2,4-oxadiazol-3-yl)urea

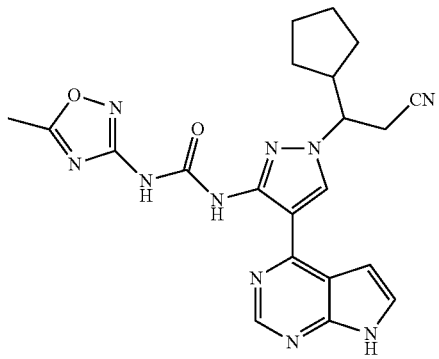 [SMILES: Cc1nc(NC(=O)Nc2nn(C(CC#N)C3CCCC3)cc2-c2ncnc3[nH]ccc23)no1]

Step A: 1-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-yl]-3-(5-methyl-1,2,4-oxadiazol-3-yl)urea

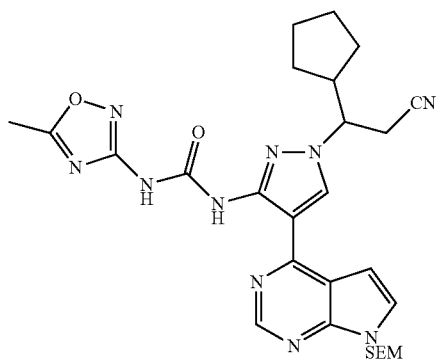 [SMILES: Cc1nc(NC(=O)Nc2nn(C(CC#N)C3CCCC3)cc2-c2ncnc3c2ccn3COCC[Si](C)(C)C)no1]

Under stirring in an ice bath, to a solution of 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile (1.0 eq., prepared from the step G of Example 1) in dichloromethane was added trichloromethyl chloroformate (0.6 eq.), followed by triethylamine (1.2 eq.). The reaction liquid was stirred for 0.5 hr at 0° C. Then, 5-methyl-1,2,4-oxadiazol-3-amine (2 eq.) and triethylamine (1.2 eq.) were respectively added thereto, and the resulting mixture was stirred for 3 hrs. The reaction was quenched by adding water and the resulting mixture was extracted with dichloromethane. The combined organic phase was successively washed with saturated ammonium chloride, saturated sodium bicarbonate and brine, dried over sodium sulfate, filtered and concentrated in vacuo. The resulting residue was separated by column chromatography on silica gel column to give the titled compound.

m/z=577[M+1]$^+$.

Step B: 1-[1-(2-cyano-1-cyclopentylethyl)-4-(7H-pyrrolo[2,3-d]pyrimidin-4-yl)-1H-pyrazol-3-yl]-3-(5-methyl-1,2,4-oxadiazol-3-yl)urea

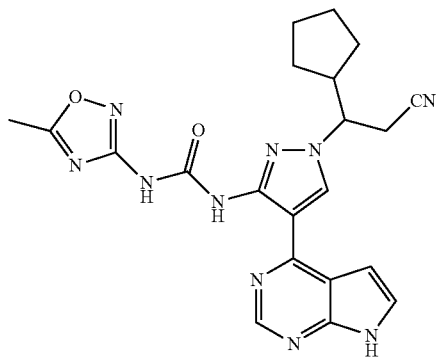 [SMILES: Cc1nc(NC(=O)Nc2nn(C(CC#N)C3CCCC3)cc2-c2ncnc3[nH]ccc23)no1]

The compound of Example 23 was prepared by removing SEM according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with 1-[1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-yl]-3-(5-methyl-1,2,4-oxadiazol-3-yl)urea.

m/z=447[M+1]$^+$.

Example 24: 1-(2-cyano-1-cyclopentylethyl)-4-(7H-pyrrolo[2,3-d]pyrimidin-4-yl)-1H-pyrazol-3-formamide

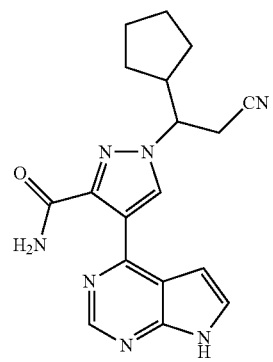 [SMILES: N#CCC(C1CCCC1)n1cc(-c2ncnc3[nH]ccc23)c(C(N)=O)n1]

Step A: ethyl 1H-pyrazol-3-formate

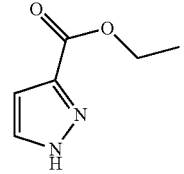

1H-pyrazol-3-formic acid (7.25 g, 64.7 mmol) was dissolved in absolute ethanol (100 mL), and concentrated sulfuric acid (0.7 mL) was added. The reaction liquid was heated and refluxed overnight. The reaction liquid was concentrated in vacuo, and the residue was diluted with ethyl acetate, washed with saturated sodium bicarbonate, and extracted with ethyl acetate. The combined organic phase was washed with brine, dried over sodium sulfate, filtered and concentrated in vacuo to give ethyl 1H-pyrazol-3-formate (8.35 g, 92% yield), as a off-white solid.

$^1$H NMR (400 MHz, CDCl$_3$) δ 12.4 (brs, 1H), 7.74 (d, J=2.4 Hz, 1H), 6.86 (d, J=2.4 Hz, 1H), 4.42 (q, J=7.2 Hz, 2H), 1.41 (t, J=7.2 Hz, 3H).

Step B: ethyl 4-iodo-1H-pyrazol-3-formate

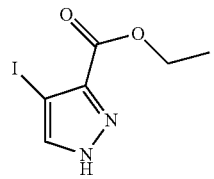

Under stirring at room temperature, to a solution of ethyl 1H-pyrazol-3-formate (8.35 g, 59.6 mmol, 1.0 eq.) in acetonitrile (150 mL) was added iodine (15.6 g, 61.5 mmol, 1.03 eq.), and then ceric ammonium nitrate (32.7 g, 59.6 mmol, 1.0 eq.) was added in batches. The reaction liquid was stirred overnight at room temperature. Then, the reaction was quenched by adding 5% NaHSO$_3$ solution, and insoluble substances were filtered. The filter cake was washed with water and ethyl acetate. The filtrate was extracted with ethyl acetate. The combined organic phase was washed with water and brine, dried over sodium sulfate, filtered and concentrated in vacuo to give ethyl 4-iodo-1H-pyrazol-3-formate (15.0 g, 95% yield).

$^1$H NMR (400 MHz, CDCl$_3$) δ 13.4 (brs, 1H), 7.89 (s, 1H), 4.46 (q, J=7.2 Hz, 2H), 1.46 (t, J=7.2 Hz, 3H).

Step C: ethyl 4-iodo-1-(4-methoxybenzyl)-1H-pyrazol-5-formate and ethyl 4-iodo-1-(4-methoxybenzyl)-1H-pyrazol-3-formate

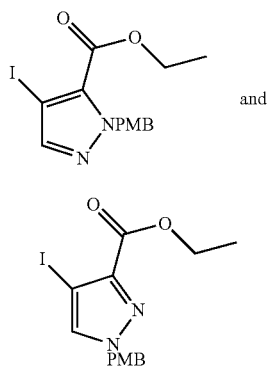

To a solution of ethyl 4-iodo-1H-pyrazol-3-formate (4.2 g, 15.8 mmol, 1.0 eq.) and potassium carbonate (4.37 g, 31.6 mmol, 2.0 eq.) in acetonitrile (45 mL) was added p-methoxybenzyl chloride (3.09 g, 19.7 mmol, 1.25 eq.) under stirring at room temperature. The reaction liquid was protected with nitrogen gas and stirred overnight at 60° C. The reaction liquid was cooled to room temperature and insoluble substances were filtered. The filter cake was washed with ethyl acetate. The filtrate was concentrated in vacuo and separated by column chromatography on silica gel column to give ethyl 4-iodo-1-(4-methoxybenzyl)-1H-pyrazol-5-formate (C1, 1.94 g, 32% yield) and ethyl 4-iodo-1-(4-methoxybenzyl)-1H-pyrazol-3-formate (C2, 2.90 g, 47% yield).

C1: $^1$H NMR (400 MHz, CDCl$_3$) δ 7.61 (s, 1H), 7.21 (d, J=8.4 Hz, 2H), 6.82 (d, J=8.4 Hz, 2H), 5.70 (s, 2H), 4.37 (q, J=7.2 Hz, 2H), 3.77 (s, 3H), 1.40 (t, J=7.2 Hz, 3H).

m/z=409[M+Na]$^+$.

C2: $^1$H NMR (400 MHz, CDCl$_3$) δ 7.36 (s, 1H), 7.22 (d, J=8.8 Hz, 2H), 6.90 (d, J=8.4 Hz, 2H), 5.31 (s, 2H), 4.44 (q, J=7.2 Hz, 2H), 3.81 (s, 3H), 1.43 (t, J=7.2 Hz, 3H).

m/z=409[M+Na]$^+$.

Step D: ethyl 1-(4-methoxybenzyl)-4-(7-{[2-(trimethylsilyl)ethoxy]methyl}-7H-pyrrolo[2,3-d]pyrimidin-4-yl)-1H-pyrazol-5-formate

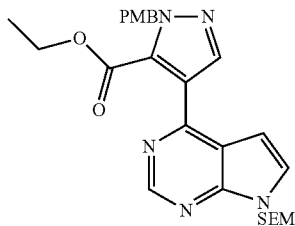

Under the protection of nitrogen gas, to a solution of ethyl 4-iodo-1-(4-methoxybenzyl)-1H-pyrazol-5-formate (1.54 g, 4.0 mmol, 1.0 eq.), diboronic acid pinacol ester (1.12 g, 4.4 mmol, 1.1 eq.) and potassium acetate (1.18 g, 12.0 mmol, 3.0 eq.) in DMSO (30 mL) was added Pd(dppf)Cl$_2$ (146 mg, 0.2 mmol, 0.05 eq.). The reactants were protected with nitrogen gas and stirred overnight at 80° C. The resulting mixture was cooled to room temperature, diluted with water and ethyl acetate, and extracted with ethyl acetate. The combined organic phase was washed with water and brine, dried over sodium sulfate, filtered and concentrated in vacuo to give 5-(ethoxycarbonyl)-1-(4-methoxybenzyl)-1H-pyrazol-4-yl boronic acid pinacol ester (1.8 g) as a crude product.

The crude product 5-(ethoxycarbonyl)-1-(4-methoxybenzyl)-1H-pyrazol-4-yl boronic acid pinacol ester (1.8 g, 4.0 mmol, 1.0 eq.) was dissolved in DMF (50 mL), and 4-chloro-7-{[2-(trimethylsilyl)ethoxy]methyl}-7H-pyrrolo[2,3-d]pyrimidine (1.25 g, 4.4 mmol, 1.1 eq.), potassium phosphate (1.7 g, 8.0 mmol, 2.0 eq.) and Pd(PPh$_3$)$_2$Cl$_2$ (140 mg, 0.2 mmol, 0.05 eq.) were added thereto. The reactants were protected with nitrogen gas and stirred overnight at 100° C. After the resulting mixture was cooled to room temperature, the mixture was diluted with water and ethyl acetate, and extracted with ethyl acetate. The combined organic phase was washed with water and brine, dried over sodium sulfate, filtered and concentrated in vacuo. The resulting residue was separated by column chromatography on silica gel column to give the titled compound (1.35 g, 67% yield), as a brown oily liquid.

$^1$H NMR (400 MHz, CDCl$_3$) δ 8.87 (s, 1H), 7.92 (s, 1H), 7.34 (d, J=4.0 Hz, 1H), 7.29 (d, J=8.8 Hz, 2H), 6.85 (d, J=8.8 Hz, 2H), 6.51 (d, J=4.0 Hz, 1H), 5.67 (s, 4H), 4.13 (q, J=7.2 Hz, 2H), 3.78 (s, 3H), 3.54 (t, J=8.4 Hz, 2H), 0.92 (m, 5H), −0.06 (s, 9H).

m/z=508[M+1]$^+$.

Step E: 1-(4-methoxybenzyl)-4-(7-{[2-(trimethylsilyl)ethoxy]methyl}-7H-pyrrolo[2,3-d]pyrimidin-4-yl)-1H-pyrazol-5-formic acid

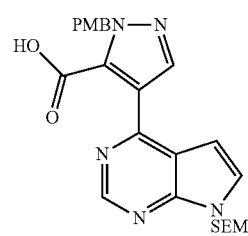

To a mixed solution of ethyl 1-(4-methoxybenzyl)-4-(7-{[2-(trimethylsilyl)ethoxy]methyl}-7H-pyrrolo[2,3-d]pyrimidin-4-yl)-1H-pyrazol-5-formate (204 mg, 0.40 mmol, 1.0 eq.) in methanol (5 mL) and water (1 mL) was added lithium hydroxide monohydrate (84 mg, 2.0 mmol, 5.0 eq.) under stirring at room temperature. The reaction liquid was stirred for 2 hrs at room temperature, and concentrated in vacuo. Ethyl acetate and 1N sodium hydroxide aqueous solution were added. The organic phase was extracted with 1N sodium hydroxide two times. 1N hydrochloric acid was added to the combined base liquid to make it acidic, and the resulting acidic liquid was extracted with ethyl acetate. The combined organic phase was washed with brine, dried over sodium sulfate, filtered and concentrated in vacuo to give the titled compound (171 mg, 89% yield).

$^1$H NMR (CDCl$_3$) δ 8.80 (1H, s), 8.40 (1H, s), 7.58 (1H, d, J=3.6 Hz), 7.43 (2H, d, J=8.8 Hz), 6.99 (1H, d, J=3.6 Hz), 6.84 (2H, d, J=8.4 Hz), 6.02 (2H, s), 5.72 (2H, s), 3.77 (3H, s), 3.56 (2H, t, J=8.4 Hz), 0.93 (2H, t, J=8.4 Hz), −0.05 (9H, s).

m/z=480[M+1]$^+$.

Step F: 1-(4-methoxybenzyl)-4-(7-{[2-(trimethylsilyl)ethoxy]methyl}-7H-pyrrolo[2,3-d]pyrimidin-4-yl)-1H-pyrazol-5-formamide

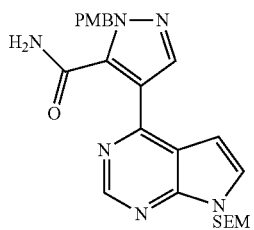

To a solution of 1-(4-methoxybenzyl)-4-(7-{[2-(trimethylsilyl)ethoxy]methyl}-7H-pyrrolo[2,3-d]pyrimidin-4-yl)-1H-pyrazol-5-formic acid (295 mg, 0.615 mmol, 1.0 eq.) in DMF was added carbonyldimidazole (150 mg, 0.923 mmol, 1.5 eq.) under stirring in an ice bath. The reaction liquid was stirred for 10 min at 0° C., and then warmed to room temperature and stirred for 1 hr. Ammonia gas was introduced into the reaction liquid and bubbled for 1 hr. Then the reaction liquid was protected with nitrogen gas and reacted overnight. The reaction liquid was diluted with water and ethyl acetate, and extracted with ethyl acetate. The combined organic phase was washed with brine, dried over sodium sulfate, filtered and concentrated in vacuo. The resulting residue was separated by column chromatography on silica gel column to give the titled compound (200 mg, 68% yield).

$^1$H NMR (CDCl$_3$) δ 11.29 (1H, s), 8.83 (1H, s), 8.09 (1H, s), 7.44 (1H, d, J=3.6 Hz), 7.38 (2H, d, J=8.4 Hz), 6.86 (2H, d, J=8.4 Hz), 6.79 (1H, d, J=3.6 Hz), 5.91 (2H, s), 5.72 (1H, s), 5.69 (2H, s), 3.78 (3H, s), 3.56 (2H, t, J=8.4 Hz), 0.93 (2H, t, J=8.4 Hz), −0.05 (9H, s).

m/z=479[M+1]$^+$.

Step G: 4-(7-{[2-(trimethylsilyl)ethoxy]methyl}-7H-pyrrolo[2,3-d]pyrimidin-4-yl)-1H-pyrazol-3-formamide

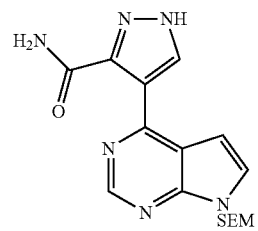 [SMILES: C[Si](C)(C)CCOCn1ccc2c(-c3c[nH]nc3C(N)=O)ncnc21]

To 1-(4-methoxybenzyl)-4-(7-{[2-(trimethylsilyl)ethoxy]methyl})-7H-pyrrolo[2,3-d]pyrimidin-4-yl)-1H-pyrazol-5-formamide (200 mg, 0.418 mmol, 1.0 eq.) in a mixed solvent of acetonitrile (1.5 mL) and water (1.5 mL) was added ceric ammonium nitrate (687 mg, 1.25 mmol, 3.0 eq.) under stirring in an ice bath. The reaction liquid was stirred for 1.5 hr at 0° C., diluted with brine and ethyl acetate, and extracted with ethyl acetate. The combined organic phase was dried over sodium sulfate, filtered and concentrated in vacuo. The resulting residue was separated by column chromatography on silica gel column to give the titled compound (79 mg, 53% yield).

$^1$H NMR (400 MHz, CDCl$_3$) δ 11.94 (brs, 1H), 11.40 (brs, 1H), 8.87 (s, 1H), 8.41 (s, 1H), 7.50 (d, J=3.6 Hz, 1H), 6.93 (d, J=3.6 Hz, 1H), 6.00 (brs, 1H), 5.71 (s, 2H), 3.57 (t, J=8.2 Hz, 2H), 0.94 (t, J=8.2 Hz, 2H), −0.04 (s, 9H).

m/z=359[M+1]$^+$.

Step H: 1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-formamide

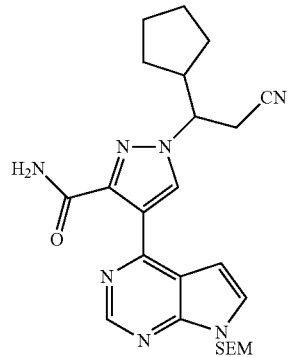 [SMILES: C[Si](C)(C)CCOCn1ccc2c(-c3cn(C(CC#N)C4CCCC4)nc3C(N)=O)ncnc21]

To a solution of 4-(7-{[2-(trimethylsilyl)ethoxy]methyl}-7H-pyrrolo[2,3-d]pyrimidin-4-yl)-1H-pyrazol-3-formamide (79 mg, 0.22 mmol, 1.0 eq.) and 3-cyclopentylacrylonitrile (67 mg, 0.55 mmol, 2.5 eq., prepared from the step A of Example 1) in acetonitrile was added 1,8-diazabicyclo[5.4.0]undec-7-ene (70 mg, 0.46 mmol, 2.1 eq.) at room temperature. The reaction liquid was stirred for 3 days at room temperature, diluted with brine and ethyl acetate, and extracted with ethyl acetate. The combined organic phase was dried over sodium sulfate, filtered and concentrated in vacuo. The resulting residue was separated by column chromatography on silica gel column to give the titled compound (76 mg, 72% yield).

¹H NMR (CDCl₃) δ 10.93 (1H, s), 8.90 (1H, s), 8.29 (1H, s), 7.47 (1H, d, J=3.6 Hz), 6.78 (1H, d, J=3.6 Hz), 5.93 (1H, s), 5.71 (2H, s), 4.40-4.45 (1H, m), 3.58 (2H, t, J=8.4 Hz), 3.17 (1H, dd, J=17.2 Hz, 7.2 Hz), 3.06 (1H, dd, J=17.2 Hz, 3.6 Hz), 2.75-2.82 (1H, m), 2.01-2.06 (1H, m), 1.54-1.82 (4H, m), 1.32-1.36 (3H, m), 0.95 (2H, t, J=8.4 Hz), −0.02 (9H, s).

m/z=480[M+1]⁺.

Step I: 1-(2-cyano-1-cyclopentylethyl)-4-(7H-pyrrolo[2,3-d]pyrimidin-4-yl)-1H-pyrazol-3-formamide

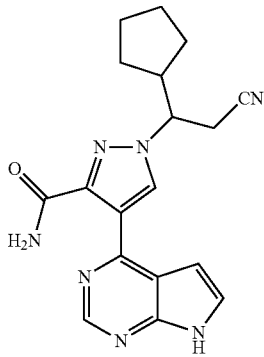 [SMILES: N#CCC(C1CCCC1)n1cc(-c2ncnc3[nH]ccc23)c(C(N)=O)n1]

The compound of Example 24 (14 mg, 96% yield), as a white solid, was prepared by removing SEM according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with 1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-formamide (20 mg, 0.042 mmol).

¹H NMR (CDCl₃) δ 11.21 (2H, s), 8.89 (1H, s), 8.34 (1H, s), 7.45 (1H, d, J=3.6 Hz), 7.12 (1H, s), 6.73 (1H, d, J=3.6 Hz), 4.43-4.47 (1H, m), 3.17 (1H, dd, J=17.2 Hz, 7.2 Hz), 3.05 (1H, dd, J=17.2 Hz, 4.0 Hz), 2.72-2.79 (1H, m), 1.95-2.04 (1H, m), 1.56-1.80 (4H, m), 1.29-1.34 (3H, m).

m/z=350[M+1]⁺.

Example 25: 1-(2-cyano-1-cyclopentylethyl)-N-methyl-4-(7H-pyrrolo[2,3-d]pyrimidin-4-yl)-1H-pyrazol-3-formamide

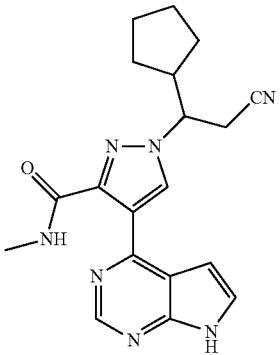 [SMILES: CNC(=O)c1nn(C(CC#N)C2CCCC2)cc1-c1ncnc2[nH]ccc12]

The compound of Example 25 was synthesized according to the process of Example 24, except that the ammonia solution in the step F was replaced with methylamine solution.

¹H NMR (CDCl₃) δ 10.67 (1H, s), 9.89 (1H, s), 8.90 (1H, s), 8.27 (1H, s), 7.44 (1H, d, J=3.6 Hz), 6.75 (1H, d, J=3.6 Hz), 4.42-4.47 (1H, m), 3.15 (1H, dd, J=17.2 Hz, 7.2 Hz), 3.01-3.08 (4H, m), 2.69-2.81 (1H, m), 1.99-2.06 (1H, m), 1.57-1.81 (4H, m), 1.32-1.35 (3H, m).

m/z=364[M+1]⁺.

Example 26: N-(2-aminoethyl)-1-(2-cyano-1-cyclopentylethyl)-4-(7H-pyrrolo[2,3-d]pyrimidin-4-yl)-1H-pyrazol-3-formamide

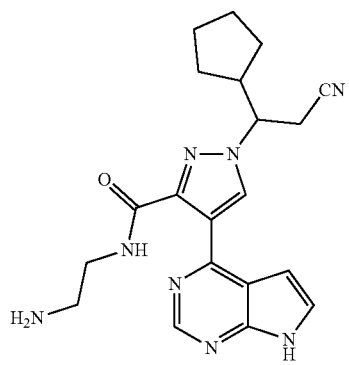 [SMILES: N#CCC(C1CCCC1)n1cc(-c2ncnc3[nH]ccc23)c(C(=O)NCCN)n1]

Step A: ethyl 1-(4-methoxybenzyl)-4-(7-{[2-(trimethylsilyl)ethoxy]methyl}-7H-pyrrolo[2,3-d]pyrimidin-4-yl)-1H-pyrazol-3-formate

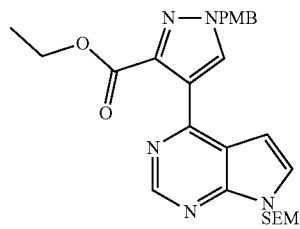

Under the protection of nitrogen gas, to a solution of ethyl 4-iodo-1-(4-methoxybenzyl)-1H-pyrazol-3-formate (1.0 g, 2.6 mmol, 1.0 eq., prepared from the step C of Example 26), diboronic acid pinacol ester (0.7 g, 2.8 mmol, 1.1 eq.) and potassium acetate (0.76 g, 7.8 mmol, 3.0 eq.) in DMSO (30 mL) was added Pd(dppf)Cl₂ (95 mg, 0.13 mmol, 0.05 eq.). The reactants were protected with nitrogen gas and stirred overnight at 80° C. After the resulting mixture was cooled to room temperature, the resulting mixture was diluted with water and ethyl acetate, and extracted with ethyl acetate. The combined organic phase was washed with water and brine, dried over sodium sulfate, filtered and concentrated in vacuo to give 3-(ethoxycarbonyl)-1-(4-methoxybenzyl)-1H-pyrazol-4-yl boronic acid pinacol ester (1.2 g) as a crude product.

The crude product 3-(ethoxycarbonyl)-1-(4-methoxybenzyl)-1H-pyrazol-4-yl boronic acid pinacol ester (1.2 g, 2.6 mmol, 1.0 eq.) was dissolved in DMF (50 mL), and 4-chloro-7-{[2-(trimethylsilyl)ethoxy]methyl}-7H-pyrrolo

[2,3-d]pyrimidine (0.8 g, 2.8 mmol, 1.1 eq.), potassium phosphate (1.1 g, 5.2 mmol, 2.0 eq.) and Pd(PPh$_3$)$_2$Cl$_2$ (91 mg, 0.13 mmol, 0.05 eq.) were added thereto. The reactants were protected with nitrogen gas and stirred overnight at 100° C. After the mixture was cooled to room temperature, the mixture was diluted with water and ethyl acetate, and extracted with ethyl acetate. The combined organic phase was washed with water and brine, dried over sodium sulfate, filtered and concentrated in vacuo. The resulting residue was separated by column chromatography on silica gel column to give the titled compound (960 mg, 73% yield), as a brown oily liquid.

$^1$H NMR (CDCl$_3$) δ 8.86 (1H, s), 8.02 (1H, s), 7.32 (1H, d, J=3.6 Hz), 7.30 (2H, d, J=8.4 Hz), 6.90 (2H, d, J=8.4 Hz), 6.39 (1H, d), 5.65 (2H, s), 5.39 (2H, s), 4.28 (2H, q, J=7.2 Hz), 3.81 (3H, s), 3.54 (2H, t, J=8.4 Hz), 1.15 (3H, t, J=7.2 Hz), 0.92 (2H, t, J=8.4 Hz), −0.06 (9H, s).

m/z=508[M+1]$^+$.

Step B: ethyl 4-(7-{[2-(trimethylsilyl)ethoxy]methyl}-7H-pyrrolo[2,3-d]pyrimidin-4-yl)-1H-pyrazol-3-formate

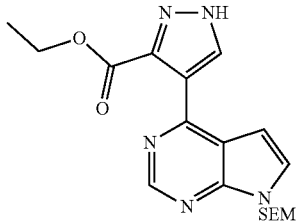 [SMILES: CCOC(=O)c1n[nH]cc1-c1ncnc2c1ccn2COCC[Si](C)(C)C]

To ethyl 1-(4-methoxybenzyl)-4-(7-{[2-(trimethylsilyl)ethoxy]methyl}-7H-pyrrolo[2,3-d]pyrimidin-4-yl)-1H-pyrazol-3-formate (336 mg, 0.66 mmol, 1.0 eq.) in a mixed solvent of acetonitrile (1.5 mL) and water (1.5 mL) was added ceric ammonium nitrate (1.1 g, 2.01 mmol, 3.0 eq.) under stirring in an ice bath. The reaction liquid was stirred for 1.5 hr at 0° C. The reaction liquid was diluted with brine and ethyl acetate, and extracted with ethyl acetate. The combined organic phase was dried over sodium sulfate, filtered and concentrated in vacuo. The resulting residue was separated by column chromatography on silica gel column to give the titled compound (175 mg, 63% yield).

$^1$H NMR (CDCl$_3$) δ 9.04 (1H, s), 8.26 (1H, s), 7.55 (1H, d, J=3.6 Hz), 6.73 (1H, d, J=3.6 Hz), 5.73 (2H, s), 4.34 (2H, q, J=7.2 Hz), 3.60 (2H, t, J=8.4 Hz), 1.24 (3H, t, J=7.2 Hz), 0.95 (2H, t, J=8.4 Hz), −0.03 (9H, s).

m/z=388[M+1]$^+$.

Step C: ethyl 1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-formate

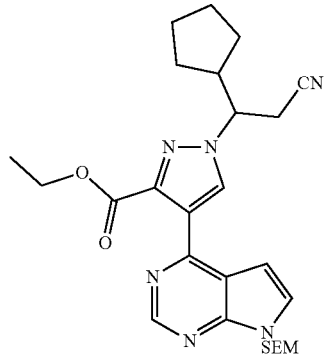 [SMILES: CCOC(=O)c1nn(C(CC#N)C2CCCC2)cc1-c1ncnc2c1ccn2COCC[Si](C)(C)C]

To a solution of ethyl 4-(7-{[2-(trimethylsilyl)ethoxy]methyl}-7H-pyrrolo[2,3-d]pyrimidin-4-yl)-1H-pyrazol-3-formate (173 mg, 0.446 mmol, 1.0 eq.) and 3-cyclopentylacrylonitrile (135 mg, 1.11 mmol, 2.5 eq., prepared from the step A of Example 1) in acetonitrile (10 mL) was added 1,8-diazabicyclo[5.4.0]undec-7-ene (142 mg, 0.94 mmol, 2.1 eq.) at room temperature. The reaction liquid was stirred overnight at room temperature, then heated to 60° C. and reacted for 5 hrs. After the mixture was cooled to room temperature, the mixture was diluted with brine and ethyl acetate, and extracted with ethyl acetate. The combined organic phase was dried over sodium sulfate, filtered and concentrated in vacuo. The resulting residue was separated by column chromatography on silica gel column to give the titled compound (79 mg, 35% yield), as a off-white solid.

$^1$H NMR (CDCl$_3$) δ 8.88 (1H, s), 7.98 (1H, s), 7.32 (1H, d, J=3.6 Hz), 6.46 (1H, d, J=3.6 Hz), 5.65 (2H, s), 4.27-4.35 (1H, m), 4.23 (2H, q, J=7.2 Hz), 3.53 (2H, t, J=8.4 Hz), 3.11 (1H, dd, J=17.2 Hz, 7.6 Hz), 2.97 (1H, dd, J=17.2 Hz, 4.0 Hz), 2.58-2.69 (1H, m), 1.88-1.99 (1H, m), 1.51-1.74 (4H, m), 1.22-1.30 (3H, m), 1.08 (3H, t, J=7.2 Hz), 0.90 (2H, t, J=8.4 Hz), −0.05 (9H, s).

m/z=509[M+1]$^+$.

Step D: N-(2-aminoethyl)-1-(2-cyano-1-cyclopentylethyl)-4-(7H-pyrrolo[2,3-d]pyrimidin-4-yl)-1H-pyrazol-3-formamide

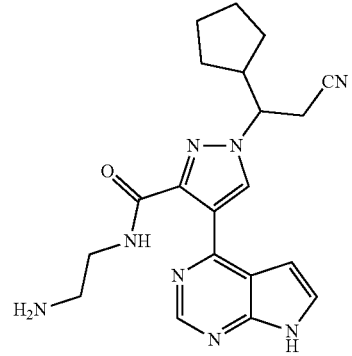 [SMILES: N#CCC(C1CCCC1)n1cc(-c2ncnc3[nH]ccc23)c(C(=O)NCCN)n1]

To a solution of ethyl 1-(2-cyano-1-cyclopentylethyl)-4-(7-{[2-(trimethylsilyl) ethoxy]methyl}-7H-pyrrolo[2,3-d]pyrimidin-4-yl)-1H-pyrazol-3-formate (79 mg, 0.16 mmol) in dichloromethane was added trifluoroacetic acid (0.5 mL) under stirring in an ice bath. The reaction liquid was protected with nitrogen gas and stirred overnight at room temperature. After the reaction liquid was concentrated in vacuo, the residue was dissolved in dichloromethane and again the resulting solution was concentrated in vacuo two times. The concentrate was dissolved in ethanol (5 mL), and ethylene diamine (0.5 mL) was added. The mixture was stirred for 0.5 hr at room temperature, and concentrated in vacuo at 60° C. The resulting residue was separated by column chromatography on silica gel column to give the titled compound of Example 26 (57 mg, 91% yield), as a beige solid.

$^1$H NMR (CDCl$_3$) δ 11.27 (1H, s), 10.20 (1H, brs), 8.79 (1H, s), 8.23 (1H, s), 7.32 (1H, d, J=3.6 Hz), 6.64 (1H, d, J=3.6 Hz), 4.36-4.42 (1H, m), 3.57-3.65 (2H, m), 3.17 (1H, dd, J=17.2 Hz, 7.2 Hz), 3.01-3.06 (3H, m), 2.69-2.74 (1H, m), 1.95-2.02 (1H, m), 1.61-1.78 (4H, m), 1.28-1.33 (3H, m).

m/z=393 [M+1]⁺.

Example 27: 1-(2-cyano-1-cyclopentylethyl)-4-(7H-pyrrolo[2,3-d]pyrimidin-4-yl)-1H-pyrazol-3-carbonitrile

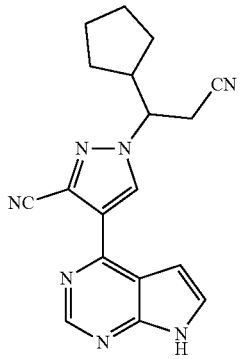 [SMILES: N#CCC(C1CCCC1)n1cc(-c2ncnc3[nH]ccc23)c(C#N)n1]

Step A: 1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-carbonitrile

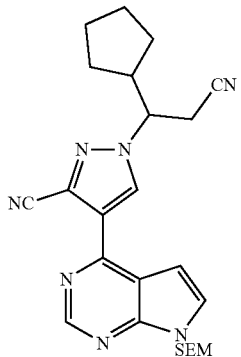 [SMILES: C[Si](C)(C)CCOCn1ccc2c(-c3cn(C(CC#N)C4CCCC4)nc3C#N)ncnc21]

Under stirring in an ice bath, 1-(2-cyano-1-cyclopentylethyl)-4-(7-{[2-(trimethylsilyl) ethoxy]methyl}-7H-pyrrolo[2,3-d]pyrimidin-4-yl)-1H-pyrazol-3-formamide (50 mg, 0.10 mmol, 1.0 eq., prepared from the step H of Example 24) is dissolved in dichloromethane (5 mL), and then triethylamine (95 mg, 0.94 mmol, 9 eq.) and trifluoroacetic anhydride (88 mg, 0.42 mmol, 4 eq.) were added. The reaction liquid was warmed to room temperature and stirred overnight. The reaction liquid was diluted with brine and ethyl acetate, and extracted with ethyl acetate. The combined organic phase was dried over sodium sulfate, filtered and concentrated in vacuo to give a crude product of the titled compound (64 mg).

¹H NMR (CDCl₃) δ 8.98 (1H, s), 8.25 (1H, s), 7.45 (1H, d, J=3.6 Hz), 6.81 (1H, d, J=3.6 Hz), 5.70 (2H, s), 4.33-4.37 (1H, m), 3.57 (2H, t, J=8.4 Hz), 3.11 (1H, dd, J=17.2 Hz, 8.0 Hz), 2.98 (1H, dd, J=17.2 Hz, 4.0 Hz), 2.60-2.63 (1H, m), 1.96-2.00 (1H, m), 1.54-1.71 (4H, m), 1.23-1.25 (3H, m), 0.93 (2H, t, J=8.4 Hz), −0.05 (9H, s).

m/z=462[M+1]⁺.

Step B: 1-(2-cyano-1-cyclopentylethyl)-4-(7H-pyrrolo[2,3-d]pyrimidin-4-yl)-1H-pyrazol-3-carbonitrile

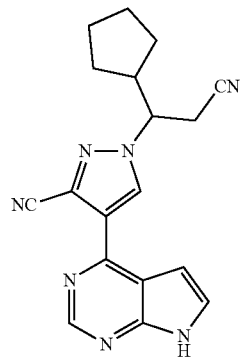 [SMILES: N#CCC(C1CCCC1)n1cc(-c2ncnc3[nH]ccc23)c(C#N)n1]

The compound of Example 27 (30 mg, 87% yield), as a white solid, was prepared by removing SEM according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with the crude product 1-(2-cyano-1-cyclopentylethyl)-4-(7-{[2-(trimethylsilyl)ethoxy]methyl}-7H-pyrrolo[2,3-d]pyrimidin-4-yl)-1H-pyrazol-3-carbonitrile (64 mg).

¹H NMR (CDCl₃) δ 9.40 (1H, s), 8.97 (1H, s), 8.25 (1H, s), 7.43 (1H, dd, J=3.6 Hz, 2.4 Hz), 6.80 (1H, dd, J=3.6 Hz, 2.0 Hz), 4.31-4.37 (1H, m), 3.15 (1H, dd, J=17.2 Hz, 8.4 Hz), 2.99 (1H, dd, J=17.2 Hz, 3.6 Hz), 2.60-2.66 (1H, m), 1.98-2.05 (1H, m), 1.59-1.78 (4H, m), 1.29-1.34 (3H, m).

m/z=332[M+1]⁺.

Example 28: 3-cyclopentyl-3-[3-(hydroxymethyl)-4-(7H-pyrrolo[2,3-d]pyrimidin-4-yl)-1H-pyrazol-1-yl]propionitrile

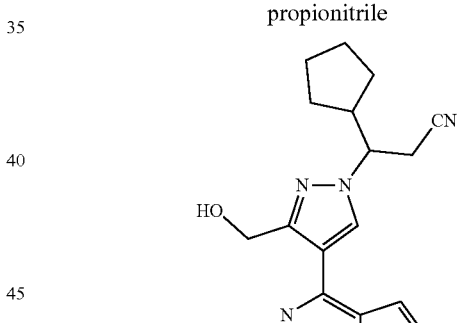

Step A: [1-(4-methoxybenzyl)-4-(7-{[2-(trimethylsilyl)ethoxy]methyl}-7H-pyrrolo[2,3-d]pyrimidin-4-yl)-1H-pyrazol-5-yl]methanol

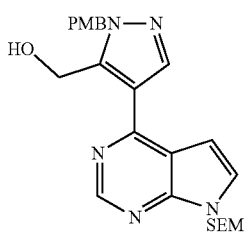

To a solution of ethyl 1-(4-methoxybenzyl)-4-(7-{[2-(trimethylsilyl)ethoxy]methyl}-7H-pyrrolo[2,3-d]pyrimidin-4-yl)-1H-pyrazol-5-formate (300 mg, 0.60 mmol, 1.0 eq., prepared from the step D of Example 24) in dry tetrahydrofuran (5 mL) was added lithium aluminum hydride (50 mg, 1.32 mmol, 2.2 eq.) in batches under the protection of nitrogen gas and in an ice bath. The reaction liquid was stirred for 3 hrs at room temperature. Under the cooling of an ice bath, water (0.05 mL) was added, followed by 1M NaOH solution (0.05 mL) and water (0.15 mL). The precipitate was filtered with diatomite, and the filter cake was washed with ethyl acetate. Saturated brine was added to the filtrate, and the resulting mixture was extracted with ethyl acetate. The combined organic phase was dried over sodium sulfate, filtered and concentrated in vacuo to give the titled compound (250 mg, 90% yield), as a yellow oily liquid.

$^1$H NMR (CDCl$_3$) δ 8.87 (1H, s), 8.18 (1H, s), 7.47 (1H, d, J=3.6 Hz), 7.20 (2H, d, J=8.4 Hz), 6.91 (1H, d, J=3.6 Hz), 6.87 (2H, d, J=8.4 Hz), 5.70 (2H, s), 5.47 (2H, s), 4.74-4.88 (2H, brs), 3.78 (3H, s), 3.55 (2H, t, J=8.4 Hz), 0.93 (2H, t, J=8.4 Hz), −0.05 (9H, s).

m/z=466[M+1]$^+$.

Step B: [4-(7-{[2-(trimethylsilyl)ethoxy]methyl}-7H-pyrrolo[2,3-d]pyrimidin-4-yl)-1H-pyrazol-3-yl]methanol

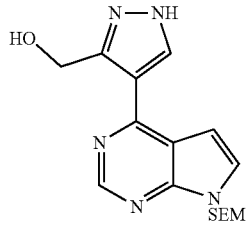 [SMILES: C[Si](C)(C)CCOCn1ccc2c(-c3c[nH]nc3CO)ncnc21]

To [1-(4-methoxybenzyl)-4-(7-{[2-(trimethylsilyl)ethoxy]methyl}-7H-pyrrolo[2,3-d]pyrimidin-4-yl)-1H-pyrazol-5-yl]methanol (250 mg, 0.537 mmol, 1.0 eq.) in a mixed solvent of acetonitrile (1.5 mL) and water (1.5 mL) was added ceric ammonium nitrate (883 mg, 1.61 mmol, 3.0 eq.) under stirring in an ice bath. The reaction liquid was stirred for 7 hrs at 0° C., diluted with brine and ethyl acetate, and extracted with ethyl acetate. The combined organic phase was dried over sodium sulfate, filtered and concentrated in vacuo. The resulting residue was separated by column chromatography on silica gel column to give the titled compound (41 mg, 22% yield).

m/z=346[M+1]$^+$.

Step C: 3-cyclopentyl-3-[3-(hydroxymethyl)-4-(7-{[2-(trimethylsilyl)ethoxy]methyl}-7H-pyrrolo[2,3-d]pyrimidin-4-yl)-1H-pyrazol-1-yl]propionitrile

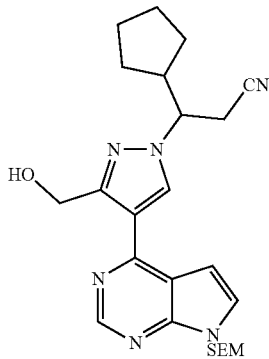 [SMILES: C[Si](C)(C)CCOCn1ccc2c(-c3cn(C(CC#N)C4CCCC4)nc3CO)ncnc21]

To a solution of [4-(7-{[2-(trimethylsilyl)ethoxy]methyl}-7H-pyrrolo[2,3-d]pyrimidin-4-yl)-1H-pyrazol-3-yl]methanol (40 mg, 0.12 mmol, 1.0 eq.) and 3-cyclopentylacrylonitrile (35 mg, 0.29 mmol, 2.5 eq., prepared from the step A of Example 1) in acetonitrile was added 1,8-diazabicyclo[5.4.0]undec-7-ene (35 mg, 0.23 mmol, 2.0 eq.) at room temperature. The reaction liquid was stirred for 5 hrs at room temperature, then warmed to 60° C. and stirred overnight. After the reaction liquid was cooled to room temperature, the reaction liquid was diluted with brine and ethyl acetate, and extracted with ethyl acetate. The combined organic phase was dried over sodium sulfate, filtered and concentrated in vacuo. The resulting residue was separated by column chromatography on silica gel column to give the titled compound (13 mg, 24% yield).

$^1$H NMR (CDCl$_3$) δ 8.86 (1H, s), 8.24 (1H, s), 7.42 (1H, d, J=3.6 Hz), 7.10-7.19 (1H, brs), 6.77 (1H, d, J=3.6 Hz), 5.69 (2H, s), 4.80 (2H, s), 4.20-4.28 (1H, m), 3.55 (2H, t, J=8.4 Hz), 3.11 (1H, dd, J=17.2 Hz, 8.0 Hz), 2.95 (1H, dd, J=17.2 Hz, 4.0 Hz), 2.61-2.69 (1H, m), 1.93-2.02 (1H, m), 1.58-1.79 (4H, m), 1.28-1.33 (3H, m), 0.93 (2H, t, J=8.4 Hz), −0.05 (9H, s).

m/z=467[M+1]$^+$.

Step D: 3-cyclopentyl-3-[3-(hydroxymethyl)-4-(7H-pyrrolo[2,3-d]pyrimidin-4-yl)-1H-pyrazol-1-yl]propionitrile

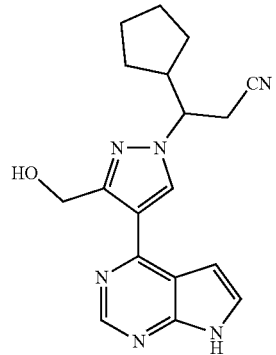 [SMILES: N#CCC(C1CCCC1)n1cc(-c2ncnc3[nH]ccc23)c(CO)n1]

3-cyclopentyl-3-[3-(hydroxymethyl)-4-(7-{[2-(trimethylsilyl)ethoxy]methyl}-7H-pyrrolo[2,3-d]pyrimidin-4-yl)-1H-pyrazol-1-yl]propionitrile (13 mg, 0.028 mmol) was dissolved in acetonitrile (1 mL) and water (1 mL), and LiBF$_4$ (54 mg, 0.58 mmol) was added. The mixture was stirred overnight at 90° C. and cooled to room temperature. An ammonia solution was added and the mixture was stirred for 2 hrs. The resulting mixture was diluted with brine and ethyl acetate, and extracted with ethyl acetate. The combined organic phase was dried over sodium sulfate, filtered and concentrated in vacuo. The resulting residue was separated by column chromatography on silica gel column to give the titled compound (6 mg, 64% yield), as a off-white solid.

$^1$H NMR (CDCl$_3$) δ 10.26 (1H, s), 8.85 (1H, s), 8.25 (1H, s), 7.41 (1H, d, J=3.2 Hz), 6.75 (1H, d, J=3.2 Hz), 4.81 (2H, s), 4.21-4.27 (1H, m), 3.11 (1H, dd, J=17.2 Hz, 8.0 Hz), 2.96 (1H, dd, J=17.2 Hz, 3.6 Hz), 2.61-2.67 (1H, m), 1.95-2.04 (1H, m), 1.57-1.78 (4H, m), 1.28-1.33 (3H, m).

m/z=337[M+1]$^+$.

Example 29: 3-cyclopentyl-3-[3-(fluoromethyl)-4-(7H-pyrrolo[2,3-d]pyrimidin-4-yl)-1H-pyrazol-1-yl]propionitrile

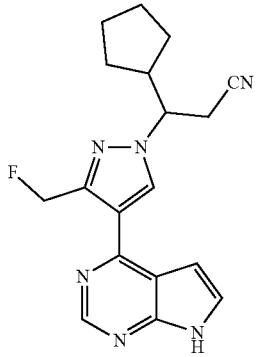 [SMILES: N#CCC(C1CCCC1)n1cc(-c2ncnc3[nH]ccc23)c(CF)n1]

Step A: 4-[5-(fluoromethyl)-1-(4-methoxybenzyl)-1H-pyrazol-4-yl]-7-{[2-(trimethylsilyl)ethoxy]methyl}-7H-pyrrolo[2,3-d]pyrimidine

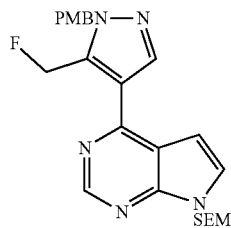

To a solution of [1-(4-methoxybenzyl)-4-(7-{[2-(trimethylsilyl)ethoxy]methyl}-7H-pyrrolo[2,3-d]pyrimidin-4-yl)-1H-pyrazol-5-yl]methanol (78 mg, 0.17 mmol, 1.0 eq., prepared from the step A of Example 28) in dry tetrahydrofuran (5 mL) was added diethylamino sulfur trifluoride (54 mg, 0.34 mmol, 2.0 eq.) under stirring in an ice bath. The reaction liquid was stirred for 3 hrs at room temperature. The reaction was quenched by adding saturated sodium bicarbonate, and the resulting mixture was extracted with ethyl acetate. The combined organic phase was washed with brine, dried over sodium sulfate, filtered and concentrated in vacuo. The resulting residue was separated by column chromatography on silica gel column to give the titled compound.

$^1$H NMR (CDCl$_3$): δ 8.86 (1H, s), 8.15 (1H, s), 7.39 (1H, d, J=3.6 Hz), 7.25 (2H, d, J=8.4 Hz), 6.88 (2H, d, J=8.4 Hz), 6.81 (1H, d, J=3.6 Hz), 6.02 (2H, d, J=48.4 Hz), 5.68 (2H, s), 5.48 (2H, s), 3.80 (3H, s), 3.55 (2H, t, J=8.4 Hz), 0.92 (2H, t, J=8.4 Hz), −0.05 (9H, s).

m/z=468[M+1]$^+$.

Step B: 4-[3-(fluoromethyl)-1H-pyrazol-4-yl]-7-{[2-(trimethylsilyl)ethoxy]methyl}-7H-pyrrolo[2,3-d]pyrimidine

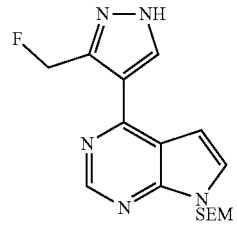 [SMILES: C[Si](C)(C)CCOCn1ccc2c(-c3c[nH]nc3CF)ncnc21]

To 4-[5-(fluoromethyl)-1-(4-methoxybenzyl)-1H-pyrazol-4-yl]-7-{[2-(trimethylsilyl) ethoxy]methyl}-7H-pyrrolo[2,3-d]pyrimidine (1.0 eq.) in a mixed solvent of acetonitrile (1.5 mL) and water (1.5 mL) was added ceric ammonium nitrate (3.0 eq.) under stirring in an ice bath. The reaction liquid was stirred for 7 hrs at 0° C., diluted with brine and ethyl acetate, and extracted with ethyl acetate. The combined organic phase was dried over sodium sulfate, filtered and concentrated in vacuo. The resulting residue was separated by column chromatography on silica gel column to give the titled compound.

m/z=348[M+1]$^+$.

Step C: 3-cyclopentyl-3-[3-(fluoromethyl)-4-(7-{[2-(trimethylsilyl)ethoxy]methyl}-7H-pyrrolo[2,3-d]pyrimidin-4-yl)-1H-pyrazol-1-yl]propionitrile

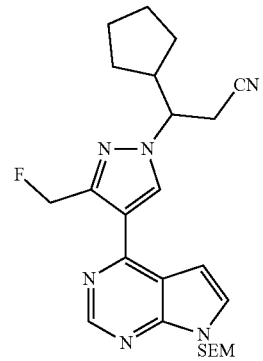 [SMILES: C[Si](C)(C)CCOCn1ccc2c(-c3cn(C(CC#N)C4CCCC4)nc3CF)ncnc21]

To a solution of 4-[3-(fluoromethyl)-1H-pyrazol-4-yl]-7-{[2-(trimethylsilyl) ethoxy]methyl}-7H-pyrrolo[2,3-d]pyrimidine (1.0 eq.) and 3-cyclopentylacrylonitrile (2.5 eq., prepared from the step A of Example 1) in acetonitrile was added 1,8-diazabicyclo[5.4.0]undec-7-ene (2.0 eq.) at room temperature. The reaction liquid was stirred for 5 hrs at room temperature, then warmed to 60° C. and stirred overnight. After the reaction liquid was cooled to room temperature, the reaction liquid was diluted with brine and ethyl acetate, and extracted with ethyl acetate. The combined organic phase was dried over sodium sulfate, filtered and concentrated in vacuo. The resulting residue was separated by column chromatography on silica gel column to give the titled compound.

m/z=469[M+1]$^+$.

Step D: 3-cyclopentyl-3-[3-(fluoromethyl)-4-(7H-pyrrolo[2,3-d]pyrimidin-4-yl)-1H-pyrazol-1-yl]propionitrile

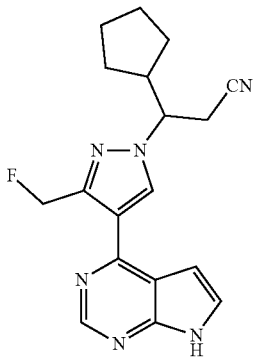 [SMILES: N#CCC(C1CCCC1)n1cc(-c2ncnc3[nH]ccc23)c(CF)n1]

3-cyclopentyl-3-[3-(fluoromethyl)-4-(7-{[2-(trimethylsilyl)ethoxy]methyl}-7H-pyrrolo[2,3-d]pyrimidin-4-yl)-1H-pyrazol-1-yl]propionitrile (1.0 eq.) was dissolved in acetonitrile (1 mL) and water (1 mL), and LiBF$_4$ (10.0 eq.) was added. The mixture was stirred overnight at 90° C. and cooled to room temperature. After an ammonia solution was added, the mixture was stirred for 2 hrs. Brine and ethyl acetate were added, and the resulting mixture was extracted with ethyl acetate. The combined organic phase was dried over sodium sulfate, filtered and concentrated in vacuo. The resulting residue was separated by column chromatography on silica gel column to give the compound of Example 29.

m/z=339[M+1]$^+$.

Example 30: 3-cyclopentyl-3-[3-(difluoromethyl)-4-(7H-pyrrolo[2,3-d]pyrimidin-4-yl)-1H-pyrazol-1-yl]propionitrile

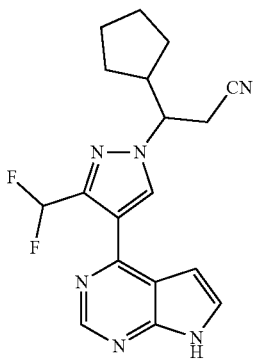 [SMILES: N#CCC(C1CCCC1)n1cc(-c2ncnc3[nH]ccc23)c(C(F)F)n1]

Step A: 1-(4-methoxybenzyl)-4-(7-{[2-(trimethylsilyl)ethoxy]methyl}-7H-pyrrolo[2,3-d]pyrimidin-4-yl)-1H-pyrazol-5-formaldehyde

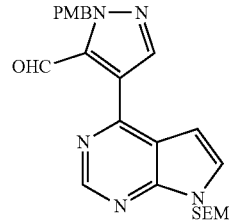

To a solution of ethyl 1-(4-methoxybenzyl)-4-(7-{[2-(trimethylsilyl)ethoxy]methyl}-7H-pyrrolo[2,3-d]pyrimidin-4-yl)-1H-pyrazol-5-formate (1.0 eq., prepared from the step D of Example 26) in dry toluene (5 mL) was added diisobutyl aluminum hydride (1.2 eq., 1 M in toluene) under the protection of nitrogen gas at −78° C. The reaction liquid was stirred for 1 hr at −78° C. The reaction was quenched by adding saturated potassium sodium tartrate solution, the resulting mixture was stirred for 15 min, and then extracted with ethyl ether. The combined organic phase was washed with water and brine, dried over sodium sulfate, filtered and concentrated in vacuo. The resulting residue was separated by column chromatography on silica gel column to give the titled compound.

m/z=464[M+1]$^+$.

Step B: 4-[5-(difluoromethyl)-1-(4-methoxybenzyl)-1H-pyrazol-4-yl)-7-{[2-(trimethylsilyl)ethoxy]methyl}-7H-pyrrolo[2,3-d]pyrimidine

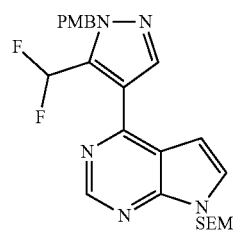

To a solution of 1-(4-methoxybenzyl)-4-(7-{[2-(trimethylsilyl)ethoxy]methyl}-7H-pyrrolo[2,3-d]pyrimidin-4-yl)-1H-pyrazol-5-formaldehyde (1.0 eq.) in dry tetrahydrofuran (5 mL) was added DAST reagent (diethylamino sulfur trifluoride, 4.0 eq.) under stirring in an ice bath. The reaction liquid was stirred for 3 hrs at room temperature. The reaction was quenched by adding saturated sodium bicarbonate, and the resulting mixture was extracted with ethyl acetate. The combined organic phase was washed with brine, dried over sodium sulfate, filtered and concentrated in vacuo. The resulting residue was separated by column chromatography on silica gel column to give the titled compound.

m/z=486[M+1]$^+$.

Step C: 4-[3-(difluoromethyl)-1H-pyrazol-4-yl]-7-{[2-(trimethylsilyl)ethoxy]methyl}-7H-pyrrolo[2,3-d]pyrimidine

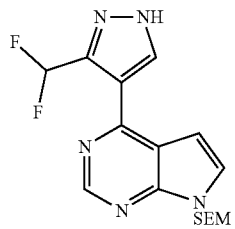 [SMILES: C[Si](C)(C)CCOCn1ccc2c(-c3c[nH]nc3C(F)F)ncnc21]

To 4-[5-(difluoromethyl)-1-(4-methoxybenzyl)-1H-pyrazol-4-yl]-7-{[2-(trimethylsilyl)ethoxy]methyl}-7H-pyrrolo[2,3-d]pyrimidine (1.0 eq.) in a mixed solvent of acetonitrile (1.5 mL) and water (1.5 mL) was added ceric ammonium nitrate (3.0 eq.) under stirring in an ice bath. The reaction liquid was stirred for 7 hrs at 0° C., diluted with brine and ethyl acetate, and extracted with ethyl acetate. The combined organic phase was dried over sodium sulfate, filtered and concentrated in vacuo. The resulting residue was separated by column chromatography on silica gel column to give the titled compound.

m/z=366[M+1]$^+$.

Step D: 3-cyclopentyl-3-[3-(difluoromethyl)-4-(7-{[2-(trimethylsilyl)ethoxy]methyl}-7H-pyrrolo[2,3-d]pyrimidin-4-yl)-1H-pyrazol-1-yl]propionitrile

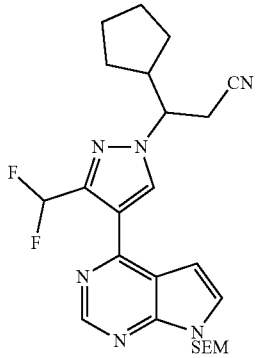 [SMILES: C[Si](C)(C)CCOCn1ccc2c(-c3cn(C(CC#N)C4CCCC4)nc3C(F)F)ncnc21]

To a solution of 4-[3-(difluoromethyl)-1H-pyrazol-4-yl]-7-{[2-(trimethylsilyl)ethoxy]methyl}-7H-pyrrolo[2,3-d]pyrimidine (1.0 eq.) and 3-cyclopentylacrylonitrile (2.5 eq., prepared from the step A of Example 1) in acetonitrile was added 1,8-diazabicyclo[5.4.0]undec-7-ene (2.0 eq.) at room temperature. The reaction liquid was stirred for 5 hrs at room temperature, then warmed to 60° C. and stirred overnight. After the reaction liquid was cooled to room temperature, the reaction liquid was diluted with brine and ethyl acetate, and extracted with ethyl acetate. The combined organic phase was dried over sodium sulfate, filtered and concentrated in vacuo. The resulting residue was separated by column chromatography on silica gel column to give the titled compound.

m/z=487[M+1]$^+$.

Step E: 3-cyclopentyl-3-[3-(difluoromethyl)-4-(7H-pyrrolo[2,3-d]pyrimidin-4-yl)-1H-pyrazol-1-yl]propionitrile

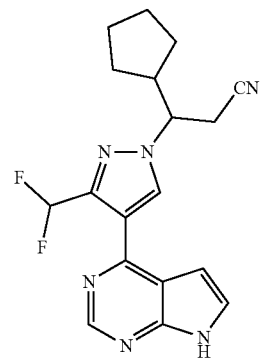 [SMILES: N#CCC(C1CCCC1)n1cc(-c2ncnc3[nH]ccc23)c(C(F)F)n1]

3-cyclopentyl-3-[3-(difluoromethyl)-4-(7-{[2-(trimethylsilyl)ethoxy]methyl}-7H-pyrrolo[2,3-d]pyrimidin-4-yl)-1H-pyrazol-1-yl]propionitrile (1.0 eq.) was dissolved in acetonitrile (1 mL) and water (1 mL), and LiBF$_4$ (10.0 eq.) was added. The mixture was stirred overnight at 90° C. and cooled to room temperature. After an ammonia solution was added, the mixture was stirred for 2 hrs. Brine and ethyl acetate were added, and the resulting mixture was extracted with ethyl acetate. The combined organic phase was dried over sodium sulfate, filtered and concentrated in vacuo. The resulting residue was separated by column chromatography on silica gel column to give the compound of Example 30.

m/z=357[M+1]$^+$.

Example 31: 3-cyclopentyl-3-{3-[(methylamino)methyl]-4-(7H-pyrrolo[2,3-d]pyrimidin-4-yl)-1H-pyrazol-1-yl}propionitrile

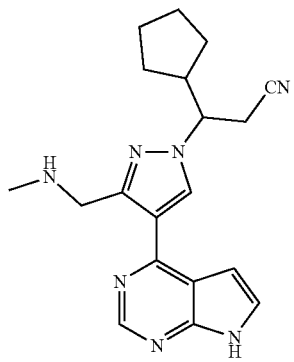

Step A: 1-[1-(4-methoxybenzyl)-4-(7-{[2-(trimethylsilyl)ethoxy]methyl}-7H-pyrrolo[2,3-d]pyrimidin-4-yl)-1H-pyrazol-5-yl]-N-methylmethylamine

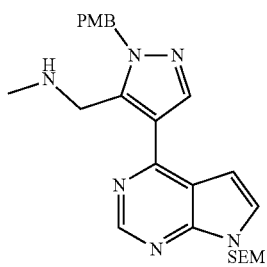

To a solution of 1-(4-methoxybenzyl)-4-(7-{[2-(trimethylsilyl)ethoxy]methyl}-7H-pyrrolo[2,3-d]pyrimidin-4-yl)-1H-pyrazol-5-formaldehyde (1.0 eq., prepared from the step A of Example 30), acetic acid (1 eq.) and acetaldehyde (40%, 1.0 eq.) in 1,2-dichloroethane was added sodium cyanoborohydride (2.0 eq.) at room temperature. The ice bath was removed, and the solution was stirred overnight at room temperature. The reaction was quenched by adding saturated ammonium chloride. The resulting mixture was extracted with ethyl acetate. The combined organic phase was washed with brine, dried over sodium sulfate, filtered and concentrated in vacuo. The resulting residue was separated by column chromatography on silica gel column to give the titled compound.

m/z=479[M+1]$^+$.

Step B: N-methyl-1-[4-(7-{[2-(trimethylsilyl)ethoxy]methyl}-7H-pyrrolo[2,3-d]pyrimidin-4-yl)-1H-pyrazol-3-yl]methylamine

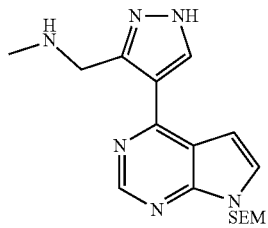 [SMILES: CNCc1n[nH]cc1-c1ncnc2c1ccn2COCC[Si](C)(C)C]

To 1-[1-(4-methoxybenzyl)-4-(7-{[2-(trimethylsilyl)ethoxy]methyl}-7H-pyrrolo[2,3-d]pyrimidin-4-yl)-1H-pyrazol-5-yl]-N-methylmethylamine (1.0 eq.) in a mixed solvent of acetonitrile (1.5 mL) and water (1.5 mL) was added ceric ammonium nitrate (3.0 eq.) under stirring in an ice bath. The reaction liquid was stirred for 7 hrs at 0° C., diluted with brine and ethyl acetate, and extracted with ethyl acetate. The combined organic phase was dried over sodium sulfate, filtered and concentrated in vacuo. The resulting residue was separated by column chromatography on silica gel column to give the titled compound.

m/z=359[M+1]$^+$.

Step C: 3-cyclopentyl-3-{3-[(methylamino)methyl]-4-(7-{[2-(trimethylsilyl)ethoxy]methyl}-7H-pyrrolo[2,3-d]pyrimidin-4-yl)-1H-pyrazol-1-yl}propionitrile

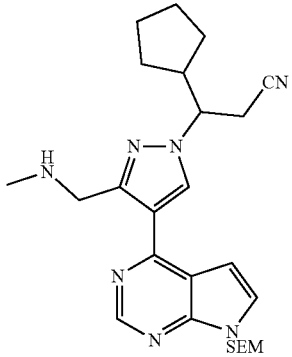 [SMILES: CNCc1nn(C(CC#N)C2CCCC2)cc1-c1ncnc2c1ccn2COCC[Si](C)(C)C]

To a solution of N-methyl-1-[4-(7-{[2-(trimethylsilyl)ethoxy]methyl}-7H-pyrrolo[2,3-d]pyrimidin-4-yl)-1H-pyrazol-3-yl]methylamine (1.0 eq.) and 3-cyclopentylacrylonitrile (2.5 eq., prepared from the step A of Example 1) in acetonitrile was added 1,8-diazabicyclo[5.4.0]undec-7-ene (2.0 eq.) at room temperature. The reaction liquid was stirred for 5 hrs at room temperature, then warmed to 60° C. and stirred overnight. After the reaction liquid was cooled to room temperature, the reaction liquid was diluted with brine and ethyl acetate, and extracted with ethyl acetate. The combined organic phase was dried over sodium sulfate, filtered and concentrated in vacuo. The resulting residue was separated by column chromatography on silica gel column to give the titled compound.

m/z=480[M+1]$^+$.

Step D: 3-cyclopentyl-3-{3-[(methylamino)methyl]-4-(7H-pyrrolo[2,3-d]pyrimidin-4-yl)-1H-pyrazol-1-yl}propionitrile

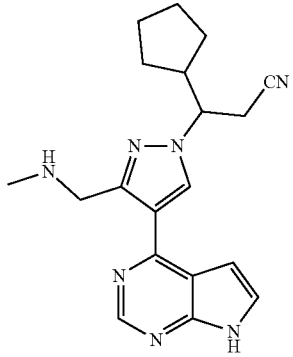 [SMILES: CNCc1nn(C(CC#N)C2CCCC2)cc1-c1ncnc2[nH]ccc12]

3-cyclopentyl-3-{3-[(methylamino)methyl]-4-(7-{[2-(trimethylsilyl)ethoxy]methyl}-7H-pyrrolo[2,3-d]pyrimidin-4-yl)-1H-pyrazol-1-yl}propionitrile (1.0 eq.) was dissolved in acetonitrile (1 mL) and water (1 mL), and LiBF$_4$ (1.0 eq.) was added. The mixture was stirred overnight at 90° C. and cooled to room temperature. After an ammonia solution was added, the mixture was stirred for 2 hrs. Brine and ethyl acetate were added, and the resulting mixture was extracted with ethyl acetate. The combined organic phase was dried over sodium sulfate, filtered and concentrated in vacuo. The resulting residue was separated by column chromatography on silica gel column to give the compound of Example 31.

m/z=350[M+1]$^+$.

Example 32: 3-[3-amino-4-(7H-pyrrolo[2,3-d]pyrimidin-4-yl)-1H-pyrazol-1-yl]-3-(3-hydroxylcyclopentyl)propionitrile

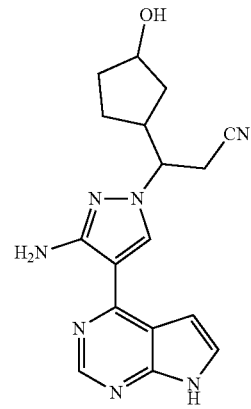 [SMILES: N#CCC(C1CCC(O)C1)n1cc(-c2ncnc3[nH]ccc23)c(N)n1]

Step A: 3-hydroxylcyclopentane carboxylic acid

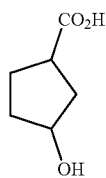

To a solution of 3-carbonylcyclopentane carboxylic acid (3.7 g, 28.9 mmol) in methanol was added sodium borohydride (1.64 g, 43.2 mmol) in batches in an ice bath. After the addition was completed, the reaction mixture was stirred at room temperature. After the reaction was completed, 1M hydrochloric acid solution was added to the reaction liquid to quench the reaction. The solvent was removed to give a crude product which was directly used in the next step.

Step B: ethyl 3-hydroxylcyclopentane formate

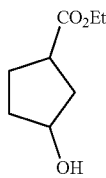

To a solution of the crude product obtained from the step A in ethanol was added concentrated sulfuric acid (1.5 mL), and the mixture was reacted overnight at 90° C. After the reaction was completed, the reaction was quenched by adding saturated sodium bicarbonate, and ethanol was removed. Water was added to the concentrate, and the resulting mixture was extracted with ethyl acetate, and column chromatographed (ethyl acetate/petroleum ether=1/5) to give racemic ethyl 3-hydroxylcyclopentane formate (2.27 g, 50% yield).

$^1$HNMR (400 MHz, CDCl$_3$) δ 4.30-4.34 (m, 1H), 4.10-4.18 (m, 2H), 2.82-2.90 (m,
$^1$H), 1.60-2.20 (m, 7H), 1.20-1.29 (m, 3H).

Step C: ethyl 3-tert-butyldimethylsiloxycyclopentane formate

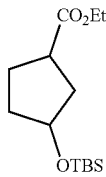

To a solution of 1H-imidazole (1.96 g, 28.73 mmol) and tert-butyldimethylsilyl chloride (2.17 g, 14.37 mmol) in DMF was added ethyl 3-hydroxylcyclopentane formate (2.27 g, 14.37 mmol). The mixture was stirred overnight until the reaction of starting materials was completed. The reaction liquid was extracted with n-hexane and the extractant was washed with water three times, and dried over sodium sulfate. The solvent was removed to give racemic ethyl 3-tert-butyldimethylsiloxycyclopentane formate (3.92 g, 100%).

$^1$HNMR (400 MHz, CDCl$_3$) δ 4.10-4.19 (m, 1H), 4.05-4.09 (m, 2H), 2.64-2.68 (m, 1H), 2.00-2.07 (m, 2H), 1.62-1.86 (m, 4H), 1.19-1.23 (m, 3H), 0.82-0.87 (m, 10H), −0.02-0.06 (m, 6H).

Step D: 3-tert-butyldimethylsiloxycyclopentane formaldehyde

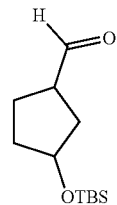

At −78° C., to a solution of racemic ethyl 3-tert-butyldimethylsiloxycyclopentane formate (3.92 g) in n-hexane was added dropwise a solution of 1.2M diisobutyl aluminum hydride in toluene, and the resulting solution was reacted for 1 hr. After the reaction was completed, the reaction was quenched by adding methanol. The mixture was washed with saturated sodium bicarbonate and dried over sodium sulfate. The resultant was column chromatographyed (ethyl acetate/petroleum ether=1:30) to give the target product (2.34 g, 65% yield).

$^1$HNMR (400 MHz, CDCl$_3$) δ 9.64 (s, 1H), 4.29-4.31 (m, 1H), 2.64-2.68 (m, 1H), 1.56-2.13 (m, 6H), 0.82-0.87 (m, 10H), 0.00-0.15 (m, 6H).

Step E: 3-[3-(tert-butyldimethylsiloxy)cyclopentyl] acrylonitrile

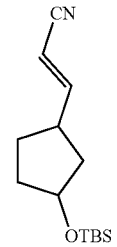 [SMILES: CC(C)(C)[Si](C)(C)OC1CCC(/C=C/C#N)C1]

To a solution of potassium tert-butoxide (246.8 mg, 2.2 mmol) in tetrahydrofuran was added diethyl cyanomethyl phosphate (426.0 mg, 2.4 mmol) in an ice bath. The ice bath was removed, and the solution was stirred for 15 min at room temperature, and again cooled to 0° C. 3-tert-butyldimethylsiloxycyclopentane formaldehyde (458.0 mg, 2.0 mmol) was added dropwise to the solution, and the resulting solution was reacted for 1 hr at room temperature until the reaction was completed. The resultant was column chromatographed (ethyl acetate/petroleum ether=1/60) to give the target product (435 mg, 87% yield).

$^1$HNMR (400 MHz, CDCl$_3$) δ 6.50-6.80 (m, 1H), 5.16-5.29 (m, 1H), 4.27-4.33 (m,
$^1$H), 2.64-2.68 (m, 1H), 1.40-2.13 (m, 6H), 0.85-0.89 (m, 10H), 0.00-0.07 (m, 6H).

Step F: 3-[3-amino-4-(7H-pyrrolo[2,3-d]pyrimidin-4-yl)-1H-pyrazol-1-yl]-3-(3-hydroxylcyclopentyl)propionitrile

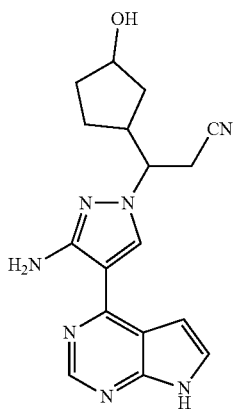 [SMILES: N#CCC(C1CCC(O)C1)n1cc(-c2ncnc3[nH]ccc23)c(N)n1]

To a solution of 3-[3-(tert-butyldimethylsiloxy)cyclopentanyl]acrylonitrile in acetonitrile were added 4-(7-{[2-(trimethylsilyl)ethoxy]methyl}-7H-pyrrolo[2,3-d]pyrimidin-4-yl)-3-amino-1H-pyrazole (prepared from the step F of Example 1) and 1,8-dizazbicyclo[5.4.0]undec-7-ene, and the mixture was stirred for 3 days at room temperature. After the reaction of starting materials was completed, the resulting mixture was concentrated, column chromatographed (ethyl acetate/n-hexane=1/15), and then treated with 20% trifluoroacetic acid in dichloromethane for 3 hrs. The resulting liquid was evaporated and treated with excessive amount of a solution of ethylene diamine in methanol overnight. The resulting mixture was stirred with ethanol/water/concentrated hydrochloric acid (10:4:3 volume ratio) for 3 hrs to remove the remaining TBS groups. The resultant was separated by column chromatography on silica gel column to give the compound of Example 32.

m/z=338[M+1]⁺.

Example 33: 3-[3-amino-4-(7H-pyrrolo[2,3-d]pyrimidin-4-yl)-1H-pyrazol-1-yl]-3-(3-fluorocyclopentyl)propionitrile

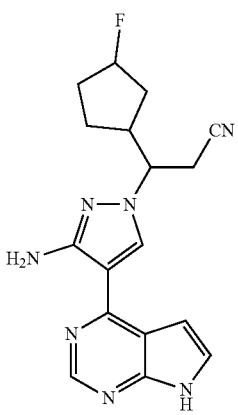 [SMILES: N#CCC(C1CCC(F)C1)n1cc(-c2ncnc3[nH]ccc23)c(N)n1]

Step A: ethyl 3-fluorocyclopentane formate

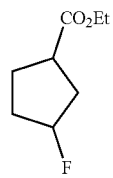

To a solution of ethyl 3-hydroxylcyclopentane formate (1.0 eq., prepared from the step B of Example 32) in dry tetrahydrofuran (5 mL) was added diethylamino sulfur trifluoride (2.0 eq.) under stirring in an ice bath. The reaction liquid was stirred for 3 hrs at room temperature. The reaction was quenched by adding saturated sodium bicarbonate, and extracted with ethyl acetate. The combined organic phase was washed with brine, dried over sodium sulfate, filtered and concentrated in vacuo. The resulting residue was separated by column chromatography on silica gel column to give the titled compound.

Step B: 3-[3-amino-4-(7H-pyrrolo[2,3-d]pyrimidin-4-yl)-1H-pyrazol-1-yl]-3-(3-fluorocyclopentyl)propionitrile

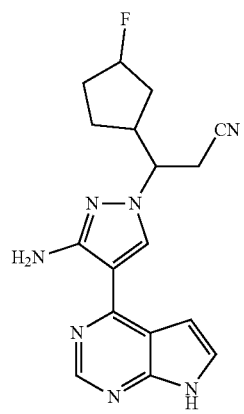 [SMILES: N#CCC(C1CCC(F)C1)n1cc(-c2ncnc3[nH]ccc23)c(N)n1]

The compound of Example 33 was prepared according to the procedures in the steps D-F of Example 32, except that ethyl 3-tert-butyldimethylsiloxycyclopentane formate was replaced with ethyl 3-fluorocyclopentane formate.

m/z=340[M+1]⁺.

Example 34: 3-[3-amino-4-(7H-pyrrolo[2,3-d]pyrimidin-4-yl)-1H-pyrazol-1-yl]-3-(3,3-difluorocyclopentyl)propionitrile

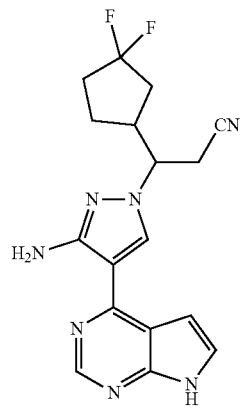 [SMILES: N#CCC(C1CCC(F)(F)C1)n1cc(-c2ncnc3[nH]ccc23)c(N)n1]

Step A: ethyl 3,3-difluorocyclopentane formate

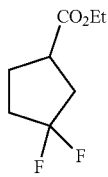

To a solution of ethyl 3-carbonylcyclopentane formate (1.0 eq.) in dry tetrahydrofuran (5 mL) was added diethylamino sulfur trifluoride (4.0 eq.) under stirring in an ice bath. The reaction liquid was stirred for 3 hrs at room temperature. The reaction was quenched by adding saturated sodium bicarbonate, and the resulting mixture was extracted with ethyl acetate. The combined organic phase was washed with brine, dried over sodium sulfate, filtered and concentrated in vacuo. The resulting residue was separated by column chromatography on silica gel column to give the titled compound.

Step B: 3,3-difluorocyclopentane formaldehyde

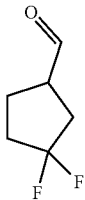

To a solution of ethyl 3,3-difluorocyclopentane formate (1.0 eq.) in dry toluene (5 mL) was added diisobutyl aluminum hydride (1.2 eq., 1 M in toluene) under the protection of nitrogen gas at −78° C. The reaction liquid was stirred for 1 hr at −78° C. The reaction was quenched by adding saturated potassium sodium tartrate solution, and the resulting mixture was stirred for 15 min, and then extracted with ethyl ether. The combined organic phase was washed with water and brine, dried over sodium sulfate, filtered and concentrated in vacuo. The resulting residue was separated by column chromatography on silica gel column to give the titled compound.

Step C: 3-(3,3-difluorocyclopentyl)acrylonitrile

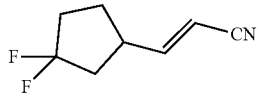 [SMILES: N#C/C=C/C1CCC(F)(F)C1]

To a solution of 1.0 M potassium tert-butoxide (1.2 eq.) in freshly distilled tetrahydrofuran was added dropwise a solution of diethyl cyanomethylphosphonate (1.2 eq.) in tetrahydrofuran under stirring in an ice bath. The ice bath was removed, and the reactants were stirred for 0.5 hr at room temperature. Then, 3,3-difluorocyclopentane formaldehyde (1.0 eq.) was added dropwise under the cooling of an ice bath. After the addition was completed, the reactants were stirred overnight at room temperature, then quenched by adding water, and extracted with ethyl acetate two times. The combined organic phase was washed with brine, dried over sodium sulfate, filtered and concentrated in vacuo. The resulting residue was separated by column chromatography on silica gel column to give 3-(3,3-difluorocyclopentyl)acrylonitrile.

Step D: 3-[3-amino-4-(7-{[2-(trimethylsilyl)ethoxy]methyl}-7H-pyrrolo[2,3-d]pyrimidin-4-yl)-1H-pyrazol-1-yl]-3-(3,3-difluorocyclopentyl)propionitrile

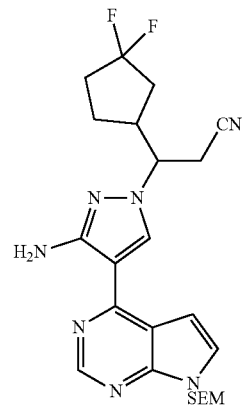 [SMILES: C[Si](C)(C)CCOCn1ccc2c(-c3cn(C(CC#N)C4CCC(F)(F)C4)nc3N)ncnc21]

Under stirring at room temperature, to a solution of 4-(7-{[2-(trimethylsilyl)ethoxy]methyl}-7H-pyrrolo[2,3-d]pyrimidin-4-yl)-3-amino-1H-pyrazole (1.0 eq., prepared from the step F of Example 1) in acetonitrile was added 3-(3,3-difluorocyclopentyl)acrylonitrile (2.52 eq.), and then DBU (2.1 eq.) was added. The reaction liquid was protected with nitrogen gas and stirred overnight at 70° C. After the reaction liquid was cooled to room temperature, the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give the titled compound.

m/z=488[M+1]⁺.

Step E: 3-[3-amino-4-(7H-pyrrolo[2,3-d]pyrimidin-4-yl)-1H-pyrazol-1-yl]-3-(3,3-difluorocyclopentyl)propionitrile

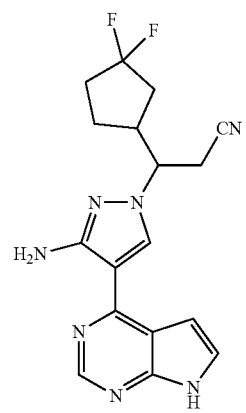 [SMILES: N#CCC(C1CCC(F)(F)C1)n1cc(-c2ncnc3[nH]ccc23)c(N)n1]

The compound of Example 34 was prepared by removing SEM according to the step H of Example 1, except that 3-[3-amino-4-(7-{[2-(trimethylsilyl)ethoxy]methyl}-7H-pyrrolo[2,3-d]pyrimidin-4-yl)-1H-pyrazol-1-yl]-3-cyclopentylpropanenitrile was replaced with 3-[3-amino-4-(7-{[2-(trimethylsilyl)ethoxy]methyl}-7H-pyrrolo[2,3-d]pyrimidin-4-yl)-1H-pyrazol-1-yl]-3-(3,3-difluorocyclopentyl)propionitrile.

m/z=358[M+1]$^+$.

Biological Activity Assays

1. Assay for Enzymatic Activity (IC$_{50}$) of Compounds

A testing platform for kinase activity of JAK2 (wild type and V617F mutant type) was established based on Homogeneous Time-Resolved Fluorescence (HTRF) assay, and the activities of the compounds were tested using the platform. The compounds were subjected to three-fold gradient dilutions with 100% DMSO with a starting concentration of 1 mM (11 dilutions in total). 4 μL of each dilution was added to 96 μL of reaction buffer (50 mM HEPES, pH 7.4, 10 mM MgCl$_2$, 1 mM EGTA, 0.01% Tween-20, 0.005% BAS, 2 mM DTT) and mixed homogeneously. 2.5 μL of the resulting liquid was then added to a 384-well plate (OptiPlate-384, available from PerkinElmer), and then 5 μL of JAK2 kinase (available from Carna) was added. The mixture was mixed homogeneously by centrifugation. Then 2.5 μL of a mixture of ATP (the final concentration is the corresponding K$_m$ value) and TK peptide (HTRF® KinEASE™-TK, available from Cisbio) was added to initiate the reaction (the total reaction volumn is 10 μL). The 384-well plate was placed in an incubator and the reaction was allowed to conduct for 120 min at 23° C. Then the reaction was terminated by adding 5 μL of Eu3+ cryptate-labled anti-phosphotyrosine antibody (available from Cisbio), and 5 μL of Streptavidin-XL-665 (HTRF® KinEASE™-TK, available from Cisbio). The plate was incubated in the incubator for 1 hr, and then the fluorescence values were read on Envision (available from PerkinElmer). The excitation wavelength was 320 nm, and the emission wavelengths for detecton were 665 nm and 620 nm. The enzymatic activity was representd by a ratio of the two readout at the two emission wavelengths. The enzymatic activity for each compound was tested at 11 concentrations, and IC$_{50}$ values of the compounds were obtained by calculating the data using GraFit6.0 software (Erithacus Software). 2. Assay for cell proliferation activity (IC$_{50}$) of compounds Human leukemia cell line HEL (available from Beijing Cuizhu Biotechnology LLC) was incubated with 1640 culture medium supplemented with 10% FBS (fetal calf serum) and 1% P/S (penicillin/streptomycin) in an incubator (37° C., 5% CO$_2$). In the tests of compounds, HEL cells were plated in a 96-well plate (Corning) at a density of 3000 cells/195 μL per well. The compounds were subjected to three-fold gradient dilutions with a starting concentration of 10 mM (11 dilutions in total). 4 μL of each dilution was added to 96 μL of 1640 culture medium to yield a 25× dilution of compounds. 5 μL of the resulting liquid was then added to 195 μL of the cell culture medium (the final concentration in DMSO is 0.1%, v/v). After 72 hrs of treatment, 35 μL of CellTiter-Blue® (available from Promega) was added. The fluorescent signals were detected on Flex Station3 (Molecular Devices) in accordance with the protocols described in the instructions. The IC$_{50}$ values of the compounds in inhibiting cell proliferation were calculated using GraphPad Prism 5.0.

The compounds prepared above were assayed according to the biological assays described herein, and the results thereof are shown below.

1. Inhibitory Activity (IC$_{50}$) of Compounds Against Wide Type (WT) and Mutant Type (V617F) of JAK2 Kinase

| Example No. | JAK2$^{WT}$ IC$_{50}$ (nM) | JAK2$^{V617F}$ IC$_{50}$ (nM) |
|---|---|---|
| Ruxolitinib | <20 | <20 |
| 1 | <20 | <20 |
| 2 | <100 | — |
| 3 | <20 | — |
| 5 | <20 | — |
| 6 | <20 | — |
| 7 | <20 | <20 |
| 9 | <20 | — |
| 10 | <20 | — |
| 11 | <20 | — |
| 12 | <20 | — |
| 13 | <20 | — |
| 14 | <20 | — |
| 15 | <20 | — |
| 16 | <100 | — |
| 17 | <20 | — |
| 18 | <1000 | — |
| 19 | <20 | — |
| 24 | <20 | — |
| 25 | <20 | — |
| 26 | <20 | — |
| 27 | <20 | — |
| 28 | <20 | — |

2. Activity of a Part of Compounds in Inhibiting Proliferation of Human Lymphoma Cell Line HEL (JAK2$^{V617F}$) (IC$_{50}$)

| Example No. | Ruxolitinib | 7 |
|---|---|---|
| IC$_{50}$ (nM) for HEL (JAK2$^{V617F}$) cells | <200 | <200 |

It can be seen from the data in the above tables that the enzymologic and cytologic inhibitory activity of the compounds of the examples of the present application are comparable to those of Ruxolitinib.

3. Assay for Efficacy in Mouse Subcutaneous Xenograft Tumor Model

SPF grade Balb/c nude mice are female and 5-6 weeks old. 0.1 mL of the suspension of Ba/F3-JAK2V617F cells in serum-free culture medium (containing 1×10$^7$ cells, 50% MatriGel) was subcutaneously injected into right flank of each mouse. When the average tumor volume reached about 500 mm$^3$, the tumor-bearing mice were sacrificed. The tumor tissues were aseptically picked up, and cut into small pieces, which were subcutaneously implanted into both flanks of Balb/c nude mice. When the average tumor volume reached about 100 mm$^3$, each mouse was marked according to serial numbers, and their tumor sizes and body weights were measured, respectively. These mice were randomly allocated from small to large in terms of tumor volume, and each group of animals was appropriately adjusted to make the average body weights of the groups in a same level. Five groups were negative control group, positive control group, low dose group, moderate dose group, and high dose group, respectively, and each group has five mice. The administration was started on the day of allocation, twice per day for 14 days. During the administration, the tumor volumes and body weights were measured twice per week. The mice were sacrificed at the end of the experiment, and the spleen was isolated and weighted.

During the experiment, the maximum long diameter (L) and the maximum transverse diameter in the vertical direction (W) of the tumor were measured to calculate the tumor volume (V) according to V (mm³)=L×W²/2. Tumor growth inhibition ratio TGI (%)=100%×(1−($T_t$−$T_0$)/($V_t$−$V_0$)), wherein $T_t$ represents the average tumor volume measured every time in the treatment group; $T_0$ represents the average tumor volume of the treatment group when being allocated; $V_t$ represents the average tumor volume measured every time in the control group; $V_0$ represents the average tumor volume of the control group when being allocated.

The results are shown in the table below.

| Compound | Dose (mg/kg) | Administration Route | Administration Frequency | TGI (%) 3 d | 7 d | 10 d | 14 d |
|---|---|---|---|---|---|---|---|
| Ruxolitinib | 100 | PO | BID | 47.96 | 47.23 | 77.72 | 64.45 |
| Hydrochloride | 25 | PO | BID | 45.45 | 16.85 | 54.49 | 40.74 |
| of the | 50 | PO | BID | 41.77 | 43.60 | 65.19 | 68.40 |
| compound of Example 5 | 100 | PO | BID | 91.62 | 79.76 | 89.37 | 85.76 |

It can be seen from the data shown in the table that the hydrochloride of the compound of Example 5 was tested for in vivo tumor inhibitory effect in Ba/F3-JAK2V617F tumor-bearing mice model, and it is found to exhibit dose-dependent inhibitory effect on Ba/F3-JAK2V617F tumor growth, and the tumor suppression effect is very remarkable. After the hydrochloride of the compound of Example 5 (100 mg/kg) was orally administered twice per day for 14 days, the tumor growth inhibition ratio (TGI) reached 85.8%, while as for the positive control Ruxolitinib (100 mg/kg) under the equivalent condition, the tumor growth inhibition ratio (TGI) was only 64.5%. The hydrochloride of the compound of Example 5 (50 mg/kg) also exhibits remarkable tumor suppression effect, and the TGI reached 68.4%, which is comparative to the tumor suppression effect of the positive control Ruxolitinib (100 mg/kg). It means that the hydrochloride of the compound of Example 5 has very significant tumor suppression effect and is much superior to Ruxolitinib.

Pharmacokinetic Assay

Pharmacokinetic Assay in Adult Male/Female SD Rats

Male/female SD rats were available from Beijing Vital River Laboratory Animal Technology Co., Ltd., and Ruxolitinib phosphate was home-made. The rats were allocated with three rats per group, and separately orally administered the suspension of a sample to be tested (5 mg/kg or 15 mg/kg) by single intragastric administration. Before the experiment, the animals were fasted overnight, and the fasting time was from 10 hrs before the administration to 4 hrs after the administration. After the administration, blood sampling was conducted at 0.25 hr, 0.5 hr, 1 hr, 2 hrs, 4 hrs, 6 hrs, 8 hrs and 24 hrs. After the animals were narcotized with isoflurane using an anaesthesia machine for small animals, 0.3 mL of whole blood was drawn from fundus venous plexus, and placed in a heparin anticoagulant tube. At 4° C., the sample was centrifuged at 4000 rpm for 5 min, and plasma was transferred to a centrifuge tube and preserved at −80° C. until the analysis was started. The sample in plasma was extracted by the protein precipitation method, and the extract liquid was analyzed by LC/MS/MS.

| | Compound of Example 7 | Ruxolitinib Phosphate[b] |
|---|---|---|
| Gender of rats | male | male |
| Oral dose (mg/kg) | 5 | 5 |
| $T_{1/2}$ (hr) | 0.5 | NC |
| Tmax (hr) | 0.33 | 0.500 |
| Cmax (ng/mL) | 13.5 | 4.69 |
| $AUC_{INF\_obs}$ (hr*ng/mL) | 20 | 3.33 |
| Formulation | 20% SBE | 0.5% MC |

Note:
[b]the data are obtained from the pharmacology review published by FDA (U.S. Food & Drug Administration).

| | Compound of Example 1 | Ruxolitinib Phosphate[a] | Ruxolitinib Phosphate[b] |
|---|---|---|---|
| Gender of rats | female | female | female |
| Oral dose (mg/kg) | 15 | 15 | 15 |
| $T_{1/2}$ (hr) | 1.56 | 1.97 | 1.98 |
| Tmax (hr) | 0.58 | 0.25 | 0.500 |
| Cmax (ng/mL) | 1903 | 107 | 267 |
| $AUC_{INF\_obs}$ (hr*ng/mL) | 3088 | 94 | 336 |
| Formulation | 10% EtOH + 40% PEG400 + 50% H$_2$O | 0.5% MC | 0.5% MC |

Note:
[a]the data are self-tested;
[b]the data are obtained from the pharmacology review published by FDA (U.S. Food & Drug Administration).

It can be seen from the PK data that at the equivalent dose, the compound of Example 1 and the compound of Example 7 have AUC and $C_{max}$ much higher than those of Ruxolitinib, and their pharmacokinetic properties are significantly superior to that of Ruxolitinib.

Healthy adult female SD rats were available from Beijing Vital River Laboratory Animal Technology Co., Ltd. The rats were allocated into two groups with three rats per group, and separately orally administered the suspension of a sample to be tested (30 mg/kg) by single intragastric administration. Before the experiment, the animals were fasted overnight, and the fasting time was from 10 hrs before the administration to 4 hrs after the administration. After the administration, blood sampling was conducted at 0.25 hr, 0.5 hr, 1 hr, 2 hrs, 4 hrs, 6 hrs, 8 hrs and 24 hrs. After the animals were narcotized with isoflurane using an anaesthesia machine for small animals, 0.4 mL of whole blood was drawn from fundus venous plexus, and placed in a heparin anticoagulant tube. At 4° C., the sample was centrifuged at 4200 rpm for 5 min, and plasma was transferred to a centrifuge tube and preserved at −80° C. until the analysis was started. The sample in plasma was extracted by the protein precipitation method, and the extract liquid was analyzed by LC/MS/MS.

| Parameter | Unit | Hydrochloride of compound of Example 5 | Compound of Example 5 | Ruxolitinib[a] |
|---|---|---|---|---|
| $t_{1/2}$ | hr | 1.95 | 2.20 | 1.22 |
| Tmax | hr | 0.33 | 0.58 | 0.50 |
| Cmax | ng/mL | 2347 | 2204 | 1143 |
| $AUC_{INFobs}$ | hr*ng/mL | 5757 | 6316 | 1345 |

Note:
[a] the data are obtained from the pharmacology review published by FDA (U.S. Food & Drug Administration).

The PK data of rats (30 mg/kg PO) exhibit that the data of the free base and hydrochloride of the compound of Example 5 are superior to those of Ruxolitinib.

Pharmacokinetic Assay in Adult Beagles

Four healthy adult beagles, available from Beijing Marshall Biotechnology Co., Ltd., were used in this study. The study was conducted two times: in the first time, the animals (two males and two females) were administered by single intravenous injection at a dose of 5 mg/kg; in the second time, the same group of animals (two males and two females) was administered by single intragastric administration at a dose of 10 mg/kg a week later. Before the experiment, the animals which will be subjected to the intragastric administration were fasted overnight, and the fasting time was from 10 hrs before the administration to 4 hrs after the administration. The group of animals which were subjected to the intravenous administration was free to get food. After the administration, blood sampling was conducted at 0.083 hr, 0.25 hr, 0.5 hr, 1 hr, 2 hrs, 4 hrs, 6 hrs, 8 hrs and 24 hrs in the group of intravenous administration. After the administration, blood sampling was conducted at 0.25 hr, 0.5 hr, 1 hr, 2 hrs, 4 hrs, 6 hrs, 8 hrs and 24 hrs in the group of intragastric administration. After the animals were lightly narcotized with isoflurane, 0.4 mL of whole blood was drawn from orbital venous plexus with a glass blood-collecting tube, and placed in a heparin anticoagulant tube. At 4° C., the sample was centrifuged at 4200 rpm for 5 min, and plasma was transferred to a centrifuge tube and preserved at −80° C. until the analysis was started. The sample in plasma was extracted by the protein precipitation method, and the extract liquid was analyzed by LC/MS/MS.

|  |  | IV 5 mg/kg | | | | PO 10 mg/kg | | | |
|---|---|---|---|---|---|---|---|---|---|
|  |  | Compound of Example 5 | | | Ruxolitinib[a] | Compound of Example 5 | | | Ruxolitinib[a] |
| Parameter | Unit | female | male | average | male | female | male | average | male |
| $t_{1/2}$ | hr | 3.65 | 3.64 | 3.64 | 2.5 | 3.03 | 3.04 | 3.03 | 2.2 |
| $AUC_{INF\_obs}$ | hr * ng/mL | 11507 | 8192 | 9849 | 13776 | 27445 | 17517 | 22481 | 15716 |
| Cl_obs | mL/hr/kg | 442 | 616 | 529 | 480 | — | — | — | — |
| Vss_obs | mL/kg | 1860 | 2089 | 1974 | 1100 | — | — | — | — |
| $T_{max}$ | hr | — | — | — | — | 1.13 | 0.25 | 0.69 | 2.0 |
| $C_{max}$ | ng/mL | — | — | — | — | 3975 | 3830 | 3903 | 3519 |
| F | % | — | — | — | — | 119 | 107 | 114 | 57 |

Note:
[a] the data are obtained from the pharmacology review published by FDA (U.S. Food & Drug Administration).

The PK data of dogs (10 mg/kg PO, 5 mg/kg IV) exhibit that the Auc of the compound of Example 5 via IV administration is comparative to that of the positive control Ruxolitinib, but the bioavailability of the compound of Example 5 via oral administration is more superior to that of the positive control Ruxolitinib (114% vs 57%).

What is claimed is:

1. A compound represented by Formula (I), a stereoisomer thereof, or a pharmaceutically acceptable salt thereof:

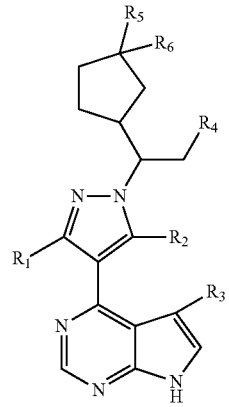

wherein, $R_1$ and $R_2$ are each independently selected from the group consisting of H, Br, I cyano, $C_{1\sim8}$alkyl, —$NR_7R_8$, —NH—$C_{1\sim6}$alkylene-$NR_9R_{10}$, —NHCO—$C_{1\sim6}$alkylene-$NR_9R_{10}$, —NH—$C_{1\sim6}$alkylene-CO—$NR_9R_{10}$, —NHCO—$C_{1\sim6}$alkylene-COO—$C_{1\sim6}$alkyl, —NH—$C_{3\sim6}$cycloalkylene —CO—$NR_9R_{10}$, —NH—$C_{2\sim6}$alkenylene-$CONR_9R_{10}$, —NH—$C_{1\sim6}$alkylene-cyano, —NHCO—NH—$R_{11}$, —$CONR_{12}R_{13}$, and —CONH—$C_{1\sim6}$alkylene-$NR_{12}R_{13}$, wherein the $C_{1\sim8}$alkyl is substituted with hydroxyl, halo, —$NH_2$, —$NH(C_{1\text{-}6}$ alkyl or $N(C_{1\sim6}$alkyl$)_2$, provided that $R_1$ and $R_2$ are not both H;

$R_7$ and $R_8$ are each independently selected from the group consisting of H, $C_{1\sim6}$alkyl, $C_{1\sim6}$alkylacyl, and $C_{1\sim6}$alkylsulfonyl; or $R_7$ and $R_8$ together with N atom to which they attach form a 5- or 6-membered heterocyclyl, and the 5- or 6-membered heterocyclyl is optionally substituted with oxo;

$R_9$ and $R_{10}$ are each independently selected from the group consisting of H, hydroxyl, and $C_{1\sim6}$alkyl; or $R_9$ and $R_{10}$ together with N atom to which they attach form a 5- or 6-membered heterocyclyl;

R₁₁ is selected from the group consisting of a 5- or 6-membered heteroaryl optionally substituted with C₁₋₄alkyl;

R₁₂ and R₁₃ are each independently selected from the group consisting of H, C₁₋₆alkyl, C₁₋₆alkylacyl, and C₁₋₆alkylsulfonyl; or R₁₂ and R₁₃ together with N atom to which they attach form a 5- or 6-membered heterocyclyl, and the 5- or 6-membered heterocyclyl is optionally substituted with oxo;

R₃ is selected from the group consisting of H and halo;

R₄ is selected from the group consisting of cyano and —CONH₂; and

R₅ and R₆ are each independently selected from the group consisting of H, hydroxyl, and halo.

2. The compound represented by Formula (I) according to claim 1, a stereoisomer thereof, or a pharmaceutically acceptable salt thereof, wherein R₁ and R₂ are each independently selected from the group consisting of H, Br, I cyano, C₁₋₆alkyl, —NR₇R₈, —NH—C₁₋₄alkylene-NR₉R₁₀, —NHCO—C₁₋₄alkylene-NR₉R₁₀, —NH—C₁₋₄alkylene-CO—NR₉R₁₀, —NHCO—C₁₋₄alkylene-COO—C₁₋₄alkyl, —NH—C₃₋₅cycloalkylene—CO—NR₉R₁₀, —NH—C₂₋₄alkenylene-CONR₉R₁₀, —NH—C₁₋₄alkylene-cyano, —NHCO—NH—R₁₁, —CONR₁₂R₁₃, and —CONH—C₁₋₄alkylene-NR₁₂R₁₃, wherein the C₁₋₆alkyl is substituted with hydroxyl, halo, —NH₂, —NH(C₁₋₆ alkyl or N(C₁₋₆alkyl)₂, provided that R₁ and R₂ are not both H;

R₇ and R₈ are each independently selected from the group consisting of H, C₁₋₄alkyl, C₁₋₄alkylacyl, and C₁₋₄alkylsulfonyl; or R₇ and R₈ together with N atom to which they attach form a heterocyclyl selected from the group consisting of:

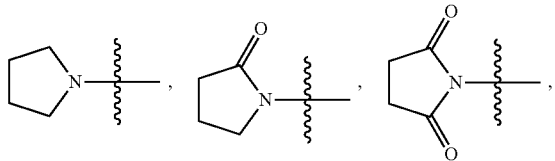

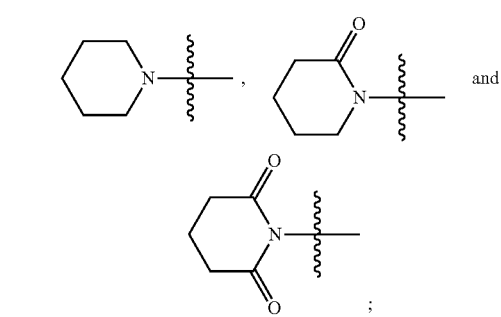

R₉ and R₁₀ are each independently selected from the group consisting of H, hydroxyl, and C₁₋₄alkyl; or R₉ and R₁₀ together with N atom to which they attach form pyrrolidinyl, piperidinyl, morpholinyl, piperazinyl or oxazolidinyl;

R₁₁ is a heteroaryl selected from the group consisting of:

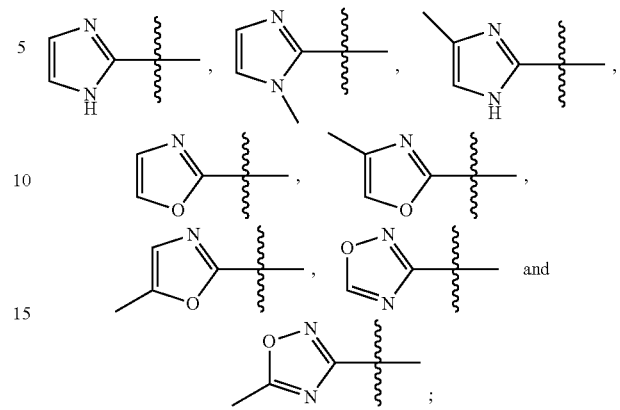

and

R₁₂ and R₁₃ are each independently selected from the group consisting of H, C₁₋₄alkyl, C₁₋₄alkylacyl, and C₁₋₄alkylsulfonyl; or R₁₂ and R₁₃ together with N atom to which they attach form a heterocyclyl selected from the group consisting of:

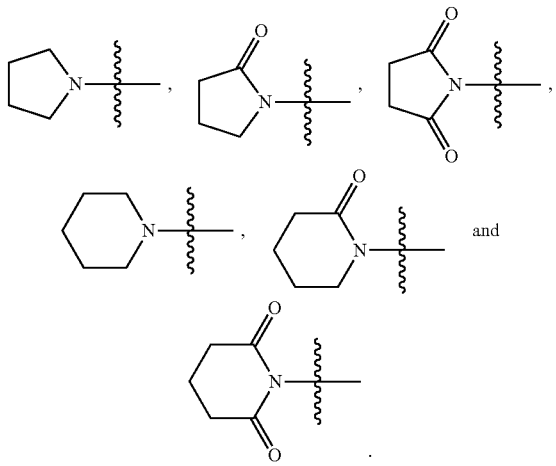

3. The compound represented by Formula (I) according to claim 2, a stereoisomer thereof, or a pharmaceutically acceptable salt thereof, wherein R₁ and R₂ are each independently selected from the group consisting of H, Br, I, cyano, methyl, ethyl, propyl, butyl, —NR₇R₈, —NH-methylene-NR₉R₁₀, —NH-ethylene-NR₉R₁₀, —NH-propylene-NR₉R₁₀, —NHCO-methylene-NR₉R₁₀, —NHCO-ethylene-NR₉R₁₀, —NHCO— propylene-NR₉R₁₀, —NH-methylene-CO—NR₉R₁₀, —NH-ethylene-CO—NR₉R₁₀, —NH-propylene-CO—NR₉R₁₀, —NHCO-methylene-COO-methyl, —NHCO-methylene-COO-ethyl, —NHCO— methylene-COO-propyl, —NHCO-ethylene-COO-methyl, —NHCO-ethylene-COO-ethyl, —NHCO— ethylene-COO-propyl, —NHCO-propylene-COO-methyl, —NHCO-propylene-COO-ethyl, —NHCO-propylene-COO-propyl, —NH-cyclopropylene-CO—NR₉R₁₀, —NH-cyclobutylene-CO—NR₉R₁₀, —NH-cyclopentylene-CO—NR₉R₁₀, —NH-vinylene-CONR₉R₁₀, —NH-propenylene-CONR₉R₁₀, —NH-allylene-CONR₉R₁₀, —NH-methylene-cyano, —NH-ethylene-cyano, —NH— propylene-cyano, —NHCO—NH—$R_{11}$, —CONR$_{12}R_{13}$, —CONH-methylene-NR$_{12}R_{13}$, —CONH—ethylene-NR$_{12}R_{13}$, and —CONH-propylene-NR$_{12}R_{13}$, wherein the methyl, ethyl, propyl or butyl is substituted with one or more groups selected from the group consisting of hydroxyl, F, Cl, Br, I, methyl-NH—, ethyl-NH—, propyl-NH—, (dimethyl)N—, (diethyl)N—, (dipropyl)N—, and (methylethyl)N—, provided that $R_1$ and $R_2$ are not both H;

$R_7$ and $R_8$ are each independently selected from the group consisting of H, methyl, ethyl, propyl, acetyl, propionyl, methylsulfonyl, ethylsulfonyl, and propylsulfonyl; or $R_7$ and $R_8$ together with N atom to which they attach form a heterocyclyl selected from the group consisting of:

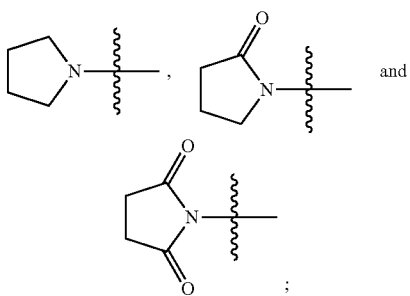

$R_9$ and $R_{10}$ are each independently selected from the group consisting of H, hydroxyl, methyl, ethyl, and propyl; or $R_9$ and $R_{10}$ together with N atom to which they attach form piperidinyl, morpholinyl or piperazinyl;

$R_{11}$ is a heteroaryl selected from the group consisting of:

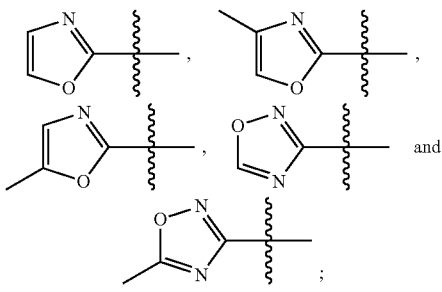

and $R_{12}$ and $R_{13}$ are each independently selected from the group consisting of H, methyl, ethyl, propyl, acetyl, propionyl, methylsulfonyl, ethylsulfonyl, and propylsulfonyl; or $R_{12}$ and $R_{13}$ together with N atom to which they attach form a heterocyclyl selected from the group consisting of:

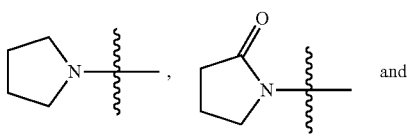

-continued

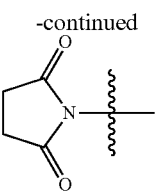

4. The compound represented by Formula (I) according to claim 3, a stereoisomer thereof, or a pharmaceutically acceptable salt thereof, wherein $R_1$ and $R_2$ are each independently selected from the group consisting of H, Br, cyano, methyl, —NR$_7R_8$, —NH-ethylene-NR$_9R_{10}$, —NHCO-methylene-NR$_9R_{10}$, —NH-methylene-CO—NR$_9R_{10}$, —NH-ethylene-CO—NR$_9R_{10}$, —NHCO-ethylene-COO-ethyl, —NH-cyclobutylene-CO—NR$_9R_{10}$, —NH-propenylene-CONR$_9R_{10}$, —NH-ethylene-cyano, —NHCO—NH—$R_{11}$, —CONR$_{12}R_{13}$, and —CONH-ethylene-NR$_{12}R_{13}$, wherein the methyl is substituted with hydroxyl, F or methyl-NH—, provided that $R_1$ and $R_2$ are not both H;

$R_7$ and $R_8$ are each independently selected from the group consisting of H, ethyl, acetyl, and methylsulfonyl; or $R_7$ and $R_8$ together with N atom to which they attach form

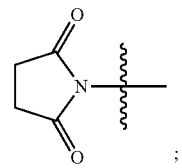 [SMILES: *N1C(=O)CCC1=O]

$R_9$ and $R_{10}$ are each independently selected from the group consisting of H and hydroxyl; or $R_9$ and $R_{10}$ together with N atom to which they attach form morpholinyl;

$R_{11}$ is

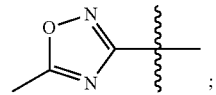

and $R_{12}$ and $R_{13}$ are each independently selected from the group consisting of H and methyl.

5. The compound represented by Formula (I) according to claim 4, a stereoisomer thereof, or a pharmaceutically acceptable salt thereof, wherein $R_1$ is selected from the group consisting of H, Br, cyano, methyl, —NR$_7R_8$, —NH—ethylene-NR$_9R_{10}$, —NHCO-methylene-NR$_9R_{10}$, —NH-methylene-CO—NR$_9R_{10}$, —NH-ethylene-CO—NR$_9R_{10}$, —NHCO-ethylene-COO-ethyl, —NH-cyclobutylene-CO—NR$_9R_{10}$, —NH-propenylene-CONR$_9R_{10}$, —NH-ethylene-cyano, —NHCO—NH—$R_{11}$, —CONR$_{12}R_{13}$, and —CONH-ethylene-NR$_{12}R_{13}$, wherein the methyl is substituted with hydroxyl, F or methyl-NH—;

$R_7$ and $R_8$ are each independently selected from the group consisting of H, ethyl, acetyl, and methylsulfonyl; or $R_7$ and $R_8$ together with N atom to which they attach form

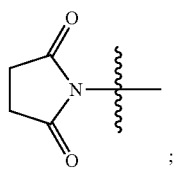

R$_9$ and R$_{10}$ are each independently selected from the group consisting of H and hydroxyl; or R$_9$ and R$_{10}$ together with N atom to which they attach form morpholinyl;

R$_{11}$ is

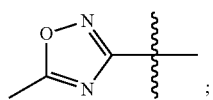 [SMILES: *c1noc(C)n1]

R$_{12}$ and R$_{13}$ are each independently selected from the group consisting of H and methyl; and R$_2$ is selected from the group consisting of H and —NH$_2$, provided that R$_1$ and R$_2$ are not both H.

6. The compound represented by Formula (I) according to claim 1, a stereoisomer thereof, or a pharmaceutically acceptable salt thereof, wherein R$_1$ is selected from the group consisting of H, Br, —CN, —NH$_2$, —NHC$_2$H$_5$, —N(C$_2$H$_5$)$_2$, —NHC(=O)CH$_3$, —NHSO$_2$CH$_3$, —NHCH$_2$CH$_2$-morpholinyl, —NHC(=O)CH$_2$-morpholinyl, —NHCH$_2$CH$_2$C(=O)-morpholinyl, —NHCH$_2$C(=O)-morpholinyl, —NHC(=O)CH$_2$CH$_2$C(=O)OC$_2$H$_5$, succinimido, —NH-cyclobutyl-C(=O)-morpholinyl, —NHCH$_2$CH=CHC(=O)NHOH, —NHCH$_2$CH$_2$C(=O)NHOH, —NHCH$_2$CH$_2$CN, —NHC(=O)NH-(5-methyl-1,2,4-oxadiazolyl), —C(=O)NH$_2$, —C(=O)NHCH$_3$, —C(=O)NHCH$_2$CH$_2$NH$_2$, —CH$_2$OH, —CH$_2$F, —CHF$_2$, and —CH$_2$NHCH$_3$; and R$_2$ is selected from the group consisting of H and —NH$_2$; provided that R$_1$ and R$_2$ are not both H.

7. The compound represented by Formula (I) according to claim 1, a stereoisomer thereof, or a pharmaceutically acceptable salt thereof, wherein R$_3$ is selected from the group consisting of H and Br.

8. The compound represented by Formula (I) according to claim 1, a stereoisomer thereof, or a pharmaceutically acceptable salt thereof, wherein R$_5$ and R$_6$ are each independently selected from the group consisting of H, hydroxyl, and F.

9. A compound selected from the group consisting of:

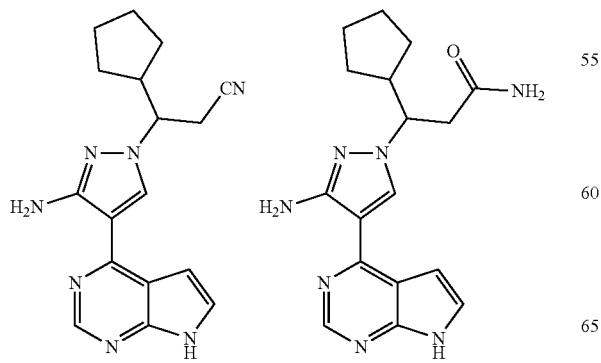

-continued

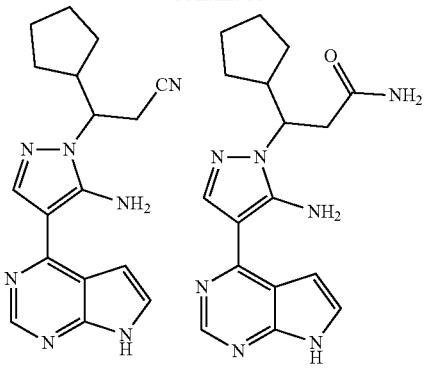

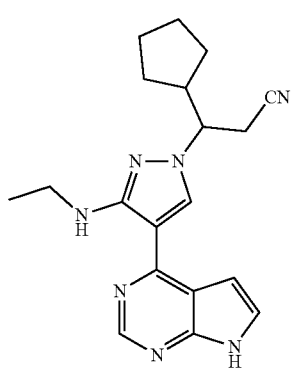

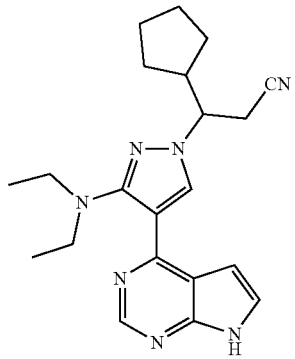

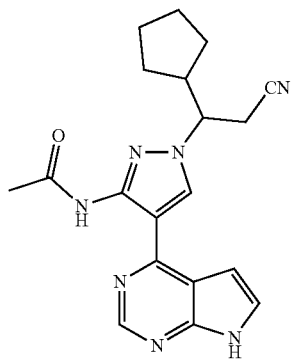

127
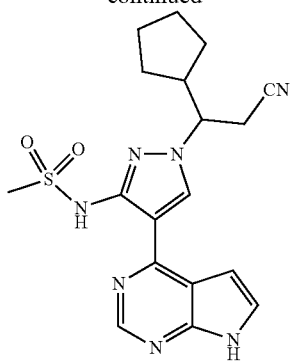
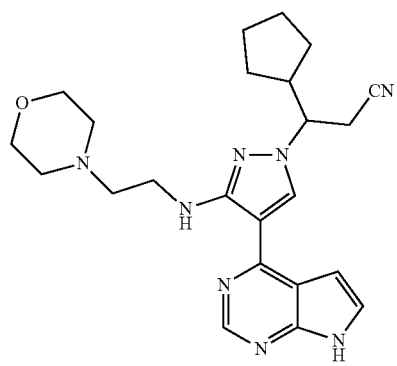
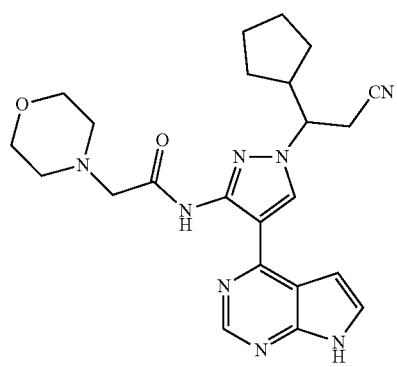
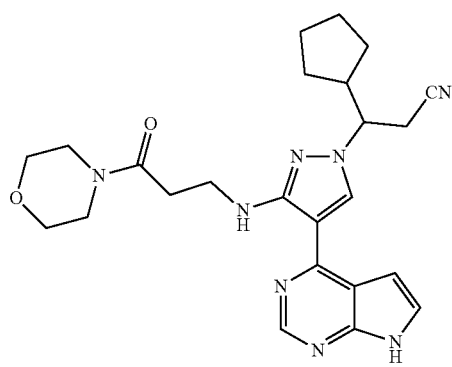
128
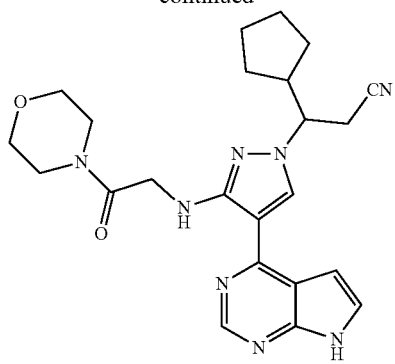
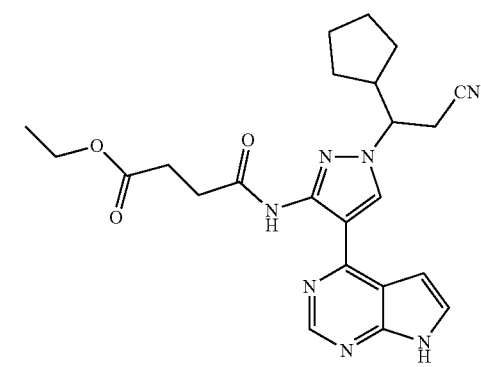
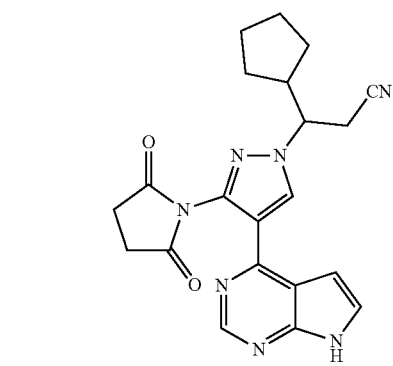
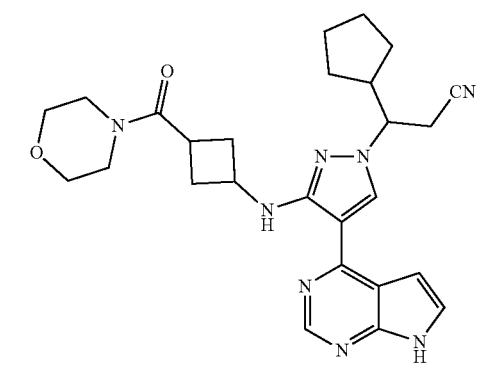 [SMILES: N#CCC(C1CCCC1)n1cc(-c2ncnc3[nH]ccc23)c(NC2CC(C(=O)N3CCOCC3)C2)n1]

129
-continued
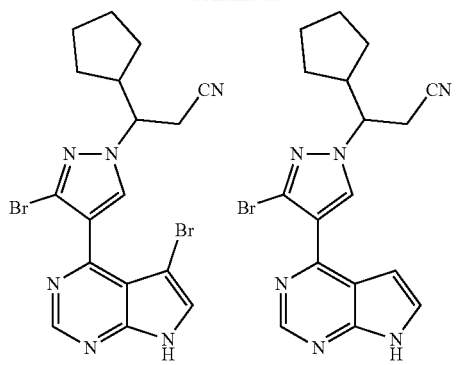
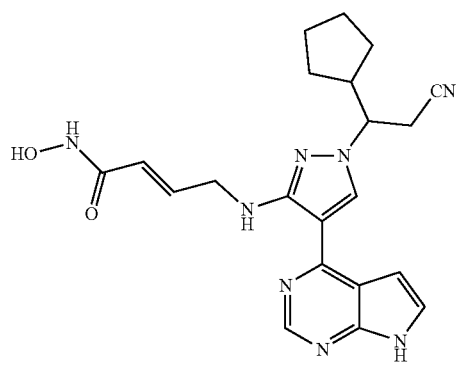
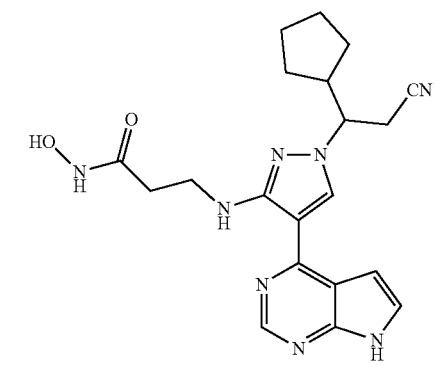
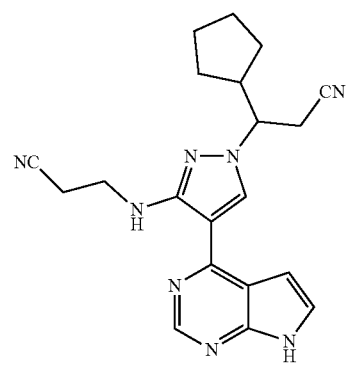
130
-continued
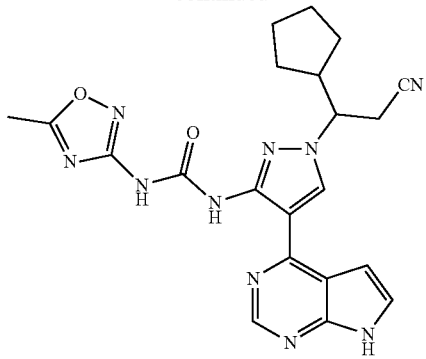
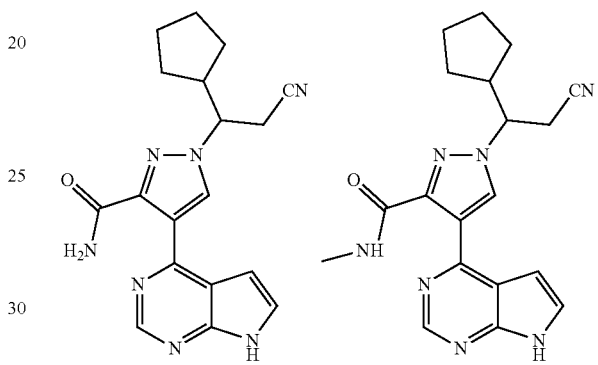
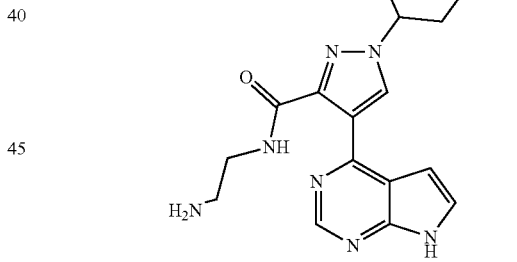
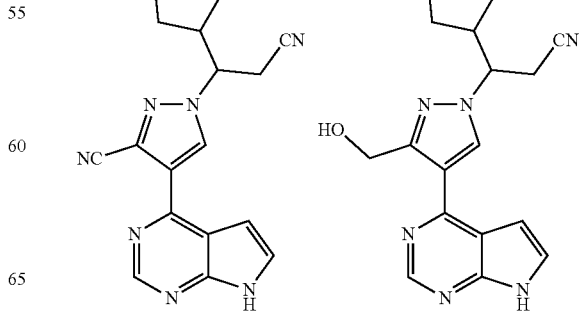

131
-continued
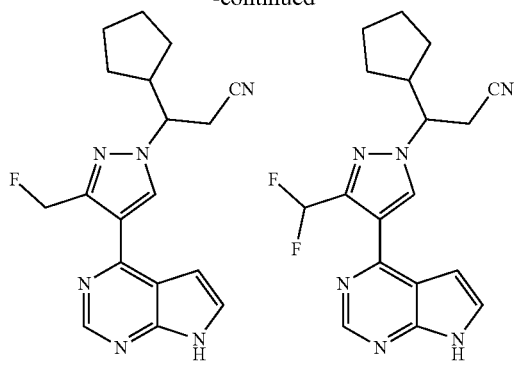
132
-continued
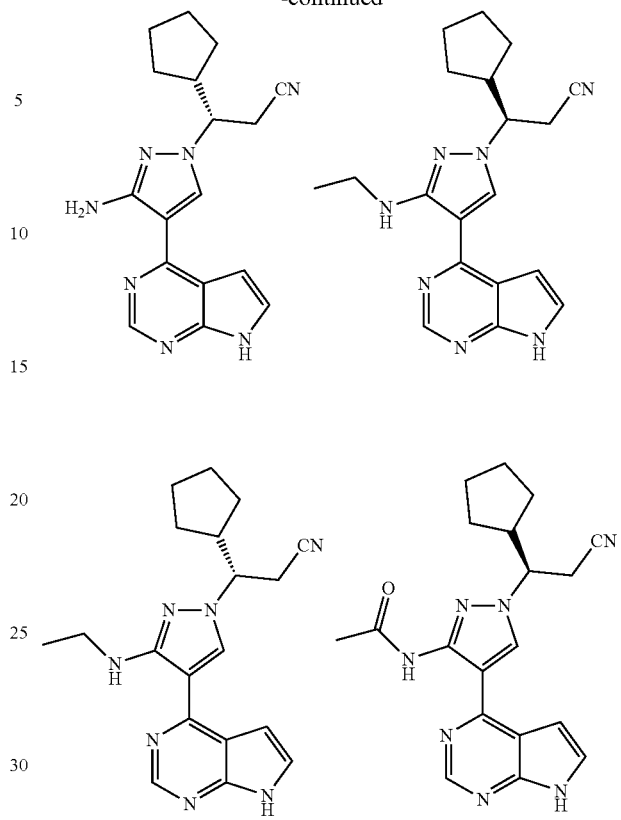
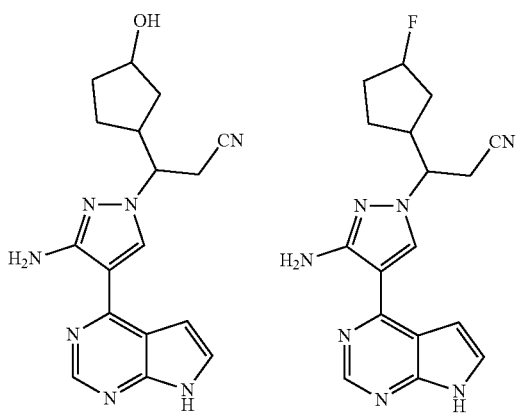
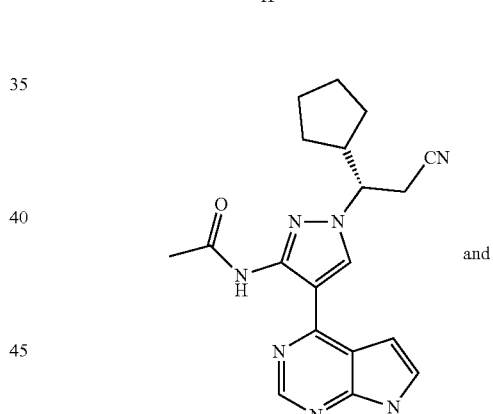
and
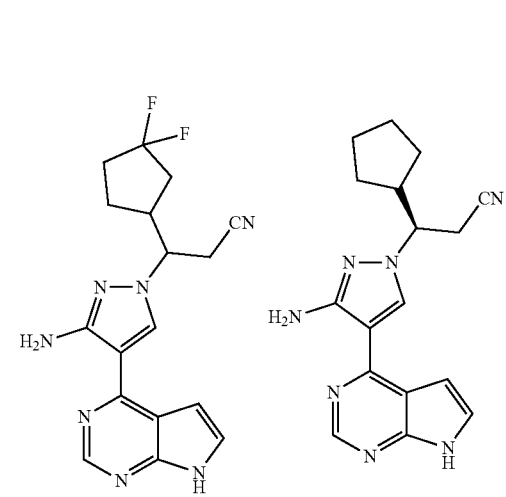
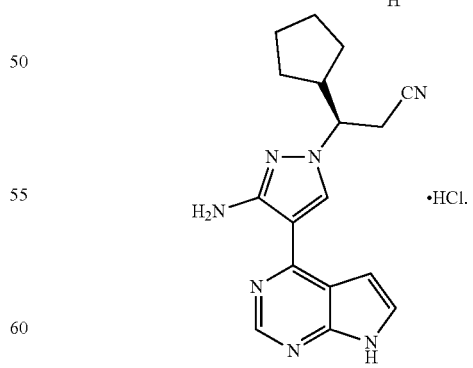
10. The compound represented by Formula (I) according to claim 1, a stereoisomer thereof, or a pharmaceutically acceptable salt thereof, wherein the compound is represented by Formula (Ia):

133

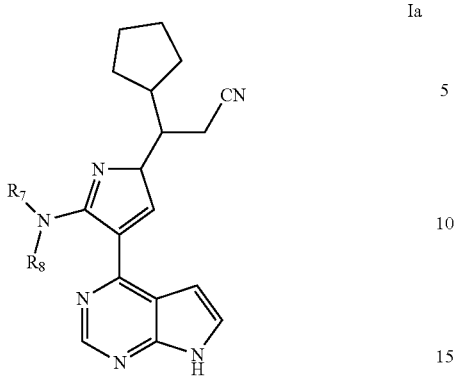

Ia wherein, $R_7$ and $R_8$ are each independently selected from the group consisting of H, $C_{1-6}$alkyl, $C_{1-6}$alkylacyl, and $C_{1-6}$alkylsulfonyl.

11. The compound represented by Formula (Ia) according to claim 10, a stereoisomer thereof, or a pharmaceutically acceptable salt thereof, wherein $R_7$ and $R_8$ are each independently selected from the group consisting of H, methyl, ethyl, propyl, butyl, pentyl, hexyl, acetyl, propionyl, butyryl, valeryl, hexanoyl, methylsulfonyl, ethylsulfonyl, propyl sulfonyl, butyl sulfonyl, pentyl sulfonyl, and hexylsulfonyl.

12. The compound represented by Formula (Ia) according to claim 10, a stereoisomer thereof, or a pharmaceutically acceptable salt thereof, wherein $R_7$ is H; and $R_8$ is selected from the group consisting of methyl, ethyl, propyl, butyl, pentyl, hexyl, acetyl, propionyl, butyryl, valeryl, hexanoyl, methyl sulfonyl, ethyl sulfonyl, propyl sulfonyl, butylsulfonyl, pentyl sulfonyl, and hexylsulfonyl.

13. The compound according to claim 10, a stereoisomer thereof, or a pharmaceutically acceptable salt thereof, which is selected from the group consisting of:

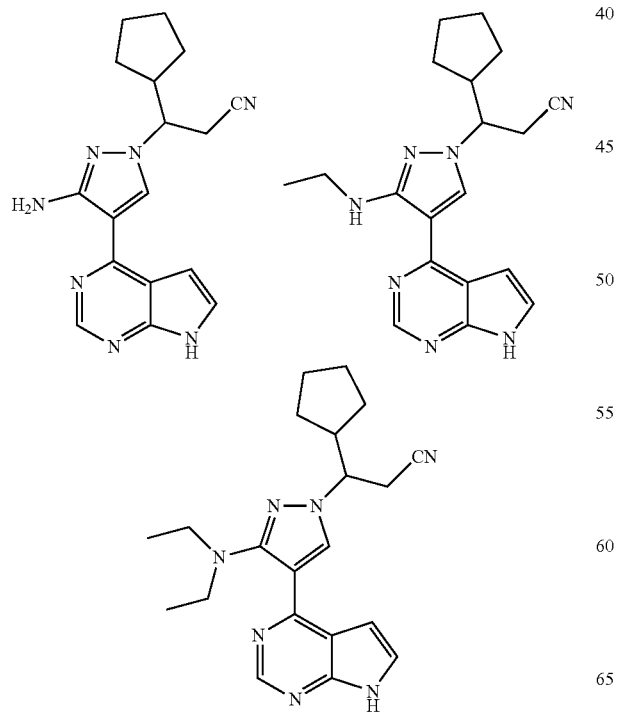

134

-continued

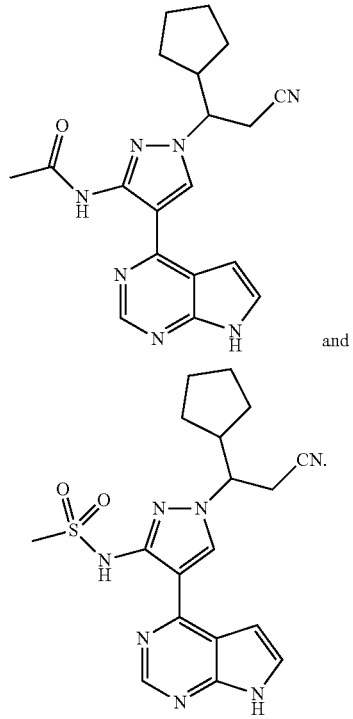

and

14. The compound according to claim 10, a stereoisomer thereof, or a pharmaceutically acceptable salt thereof, which is selected from the group consisting of:

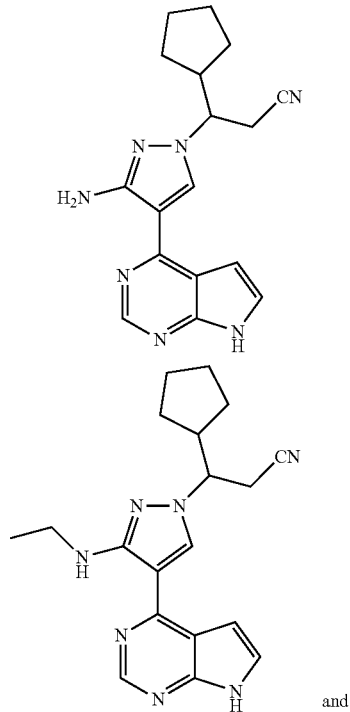

and

-continued

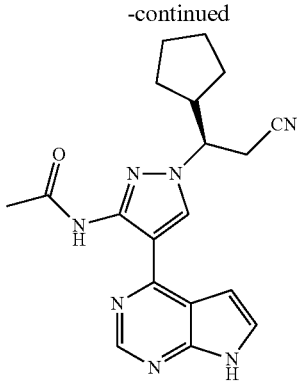

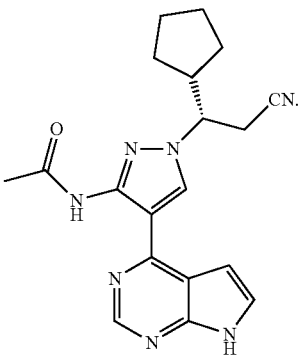
and

15. The compound according to claim 10, a stereoisomer thereof, or a pharmaceutically acceptable salt thereof, which is selected from the group consisting of:

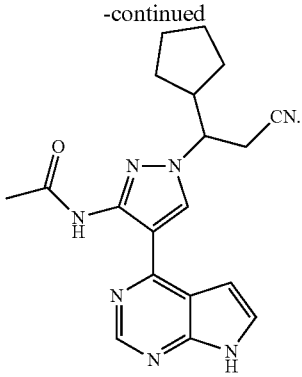

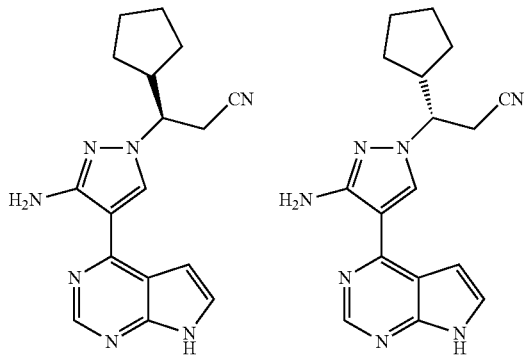

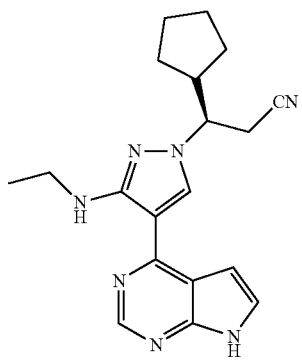

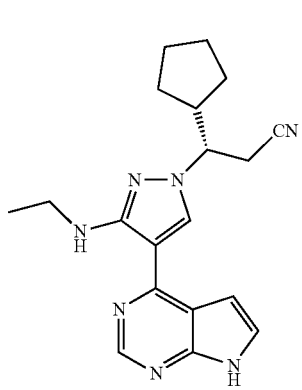

16. A pharmaceutical composition comprising the compound according to claim 1, a stereoisomer thereof, or a pharmaceutically acceptable salt thereof, and one or more pharmaceutically acceptable carriers or excipients.

17. A method for treating a disease mediated by Janus kinase, comprising administering to a patient a therapeutically effective amount of the compound according to claim 1, a stereoisomer thereof, or a pharmaceutically acceptable salt thereof, or the pharmaceutical composition according to claim 16, wherein the disease mediated by Janus kinase is lymphoma or leukemia.

18. A compound having the following structure:

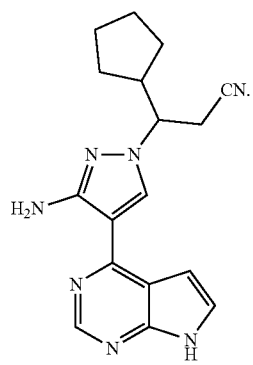 [SMILES: N#CCC(C1CCCC1)n1cc(-c2ncnc3[nH]ccc23)c(N)n1]

19. A compound having the following structure:
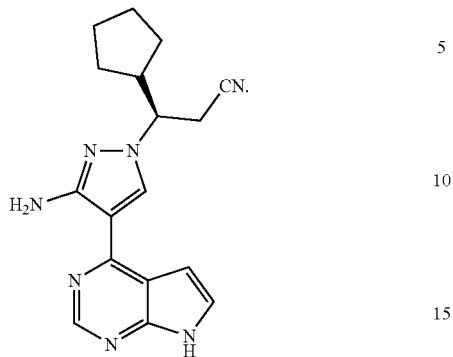
* * * * *